US007427490B2

(12) United States Patent
Valkirs et al.

(10) Patent No.: US 7,427,490 B2
(45) Date of Patent: Sep. 23, 2008

(54) DIAGNOSTIC MARKERS OF STROKE AND CEREBRAL INJURY AND METHODS OF USE THEREOF

(75) Inventors: Gunars E. Valkirs, Escondido, CA (US); Jeffrey R. Dahlen, San Diego, CA (US); Howard J. Kirchick, San Diego, CA (US); Kenneth F. Buechler, San Diego, CA (US)

(73) Assignee: Biosite Incorporated, San Diego, CA (US)

( * ) Notice: Subject to any disclaimer, the term of this patent is extended or adjusted under 35 U.S.C. 154(b) by 769 days.

(21) Appl. No.: 10/225,082

(22) Filed: Aug. 20, 2002

(65) Prior Publication Data

US 2003/0119064 A1    Jun. 26, 2003

Related U.S. Application Data

(60) Provisional application No. 60/346,485, filed on Jan. 2, 2002, provisional application No. 60/334,964, filed on Nov. 30, 2001, provisional application No. 60/313,775, filed on Aug. 20, 2001.

(51) Int. Cl.
G01N 33/00 (2006.01)
(52) U.S. Cl. .................. 435/7.92; 435/7.1; 436/501; 436/811
(58) Field of Classification Search ............... 435/6, 435/7.1, 7.92–7.95, 7.9, 973; 436/518, 524, 436/501, 164, 811
See application file for complete search history.

(56) References Cited

U.S. PATENT DOCUMENTS

| | | | |
|---|---|---|---|
| 4,447,545 A | 5/1984 | DeFazio et al. |
| 5,114,923 A | 5/1992 | Seilhamer et al. |
| 5,290,678 A | 3/1994 | Jackowski |
| 5,294,537 A | 3/1994 | Batt |
| 5,350,842 A | 9/1994 | Norgard |
| 5,352,587 A | 10/1994 | Chang et al. |
| 5,422,393 A | 6/1995 | Bricker et al. |
| 5,480,792 A | 1/1996 | Buechler et al. |
| 5,482,935 A | 1/1996 | Adelman et al. |
| 5,525,524 A | 6/1996 | Buechler et al. |
| 5,631,171 A | 5/1997 | Sandstrom et al. |
| 5,679,526 A | 10/1997 | Buechler et al. |
| 5,683,885 A | 11/1997 | Kieback |
| 5,690,103 A | 11/1997 | Groth et al. |
| 5,786,163 A | 7/1998 | Hall |
| 5,824,799 A | 10/1998 | Buechler et al. |
| 5,851,776 A | 12/1998 | Valkirs |
| 5,885,527 A | 3/1999 | Buechler |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,057,098 A | 5/2000 | Buechler et al. |
| 6,099,469 A | 8/2000 | Armstrong et al. |
| 6,113,855 A | 9/2000 | Buechler et al. |
| 6,117,644 A | 9/2000 | DeBold |
| 6,124,430 A | 9/2000 | Mischak et al. |
| 6,143,576 A | 11/2000 | Buechler |
| 6,235,489 B1 | 5/2001 | Jackowski |
| 6,268,223 B1 | 7/2001 | Cornell-Bell et al. |
| 6,309,888 B1 | 10/2001 | Holvoet et al. |
| 6,443,889 B1 | 9/2002 | Groth et al. |
| 6,495,519 B1 | 12/2002 | He et al. |
| 6,586,244 B2 | 7/2003 | Reinhard |
| 6,627,457 B2 * | 9/2003 | Pandian et al. ............... 436/501 |
| 6,670,138 B2 * | 12/2003 | Gonzalez-Zulueta et al. . 435/7.1 |
| 6,828,107 B2 | 12/2004 | Asada et al. |
| 2002/0052000 A1 | 5/2002 | Parthasarathy et al. |
| 2002/0106708 A1 | 8/2002 | Thomas et al. |
| 2003/0022235 A1 | 1/2003 | Dahlen et al. |
| 2004/0072805 A1 | 4/2004 | Warren et al. |
| 2004/0167341 A1 | 8/2004 | Haffner et al. |
| 2005/0181386 A1 | 8/2005 | Diamond et al. |
| 2005/0244902 A1 | 11/2005 | Gotze et al. |

(Continued)

FOREIGN PATENT DOCUMENTS

WO    WO 00/18801    4/2000

(Continued)

OTHER PUBLICATIONS

Yakoviev et al., Activation of CPP32-Like Caspases Contributes to Neuronal Apoptosis and Neurological Dysfunction after Traumatic Brain Injury, The Journal of Neuroscience, Oct. 1, 1997, 17 (19): 7415-7424.*

(Continued)

Primary Examiner—Long V. Le
Assistant Examiner—Gary W Counts
(74) Attorney, Agent, or Firm—Wilson Sonsini; Goodrich and Rosati

(57) ABSTRACT

The present invention relates to methods for the diagnosis and evaluation of stroke and transient ischemic attacks. In a particular aspect, patient samples are analyzed for the presence or amount of a panel of markers comprising one or more specific markers for cerebral injury and one or more non-specific markers for cerebral injury. In an alternative aspect, samples are analyzed for B-type natriuretic peptide. A variety of markers are disclosed for assembling a panel for such diagnosis and evaluation. In various aspects, the invention provides methods for early detection and differentiation of stroke types and transient ischemic attacks, for determining the prognosis of a patient presenting with stroke symptoms, and identifying a patient at risk for cerebral vasospasm. Invention methods provide rapid, sensitive and specific assays to greatly increase the number of patients that can receive beneficial stroke treatment and therapy, and reduce the costs associated with incorrect stroke diagnosis.

34 Claims, No Drawings

FOREIGN PATENT DOCUMENTS

| WO | WO 01/18801 | 4/2000 |
|---|---|---|
| WO | WO 00/52476 | 9/2000 |
| WO | WO 00/52476 A1 | 9/2000 |
| WO | WO 01/14885 | 3/2001 |
| WO | WO 01/16599 | 3/2001 |
| WO | WO 01/42793 | 6/2001 |
| WO | WO 02/083913 | 10/2002 |
| WO | WO 02/089657 | 11/2002 |
| WO | WO 03/002553 | 1/2003 |

OTHER PUBLICATIONS

Huttunen et al., Coregulation of Neurite Outgrowth and Cell Survival by Amphoterin and S100 Proteins through Receptor for Advanced glycation End Products (RAGE) Activation., Journ. of Biological Chem. vol. 275, Dec. 22, 2000, pp. 40096-40105.*

Mussack et al., early cellular brain damage and systemic inflammatory response after cardiopulmonary resuscitation or isolated severehad trauma, Resuscitation, (May 2001) vol. 49, No. 2, pp. 193-199.*

Harter et al., Caspase-3 activity is present in cerebrospinal fluid from patients with traumatic brain injury, Journal of Neuroimmunology 121 (2001) 76-78.*

Webster's II New Riverside University Dictionary, 1994, by Houghton Mifflin Company, p. 1212.*

Vander et al., Human Physiology by McGraw-Hill, Sixth Edition, 1994, pp. 214, 215 and 230.*

Mussack et al., Early cellular brain damage and systemic inflammatory response after cardiopulmonary resuscitation or isolated severe head trauma, Resuscitation, vol. 40, Issue 2, May 2001, pp. 193-199.*

Tarkowski et al., Intrathecel release an pro-and anti-inflammatory cytokines during stroke, Clin Exp Immunol 1997; 110: pp. 492-499.*

Feinberg et al., "Guidelines for the Management of Transient Ischemic Attacks." Stroke, 25(6): 1320-1335, Jun. 1994.

Herrmann et al., "Release of Glial tissue-specific proteins after acute stroke: A comparison analysis of serum concentrations of protein S-100B and Glial fibrillary acidic protein." Stroke, 31:2670-2677, 2000.

Napoli et al., "C-reactive protein in ischemic stroke: An independent prognostic factor." Stroke, 32:917-924, 2001.

Strand et al., "Brains and plasma proteins in spinal fluid as markers for brain damage and severity of stroke." Stroke: 15(1): 138-144, 1994.

Aggarwal et al., "Evaluation of serum lipid protein and cardiac enzyme changes in cerebrovascular accidents," JIMA, 93:331-332, 1995.

Akiyama et al., "Changes in serum concentrations of matrix metalloproteins, tissue inhibitors of metallo proteinases and Type IV collagen in patients with various types of glomerulonephritis," Res. Commun. In Mol. Path. and Pharm., 95(2): 115-128, 1997.

Albrecht et al., "Detection of circulating tissue factor VII in a normal population," Thrombosis and Haemostasis, 75(5): 772-7, 1996.

Albrechtsen and Bock, "Quantification of glial fibrillary acidic protein (GFAP) in human body fluids by means of Elisa employing a monoclonal antibody." Journal of Neuroimmunology, 8:301-309, 1985.

Austgulen et al., "Increased maternal plasma levels of soluble adhesion in molecules (ICAM-1, VCAM-1, E-selectin) in preeclampsia," Eur. J. Obstet. Gynecol. Reprod. Biol., 71:53-58, 1997.

Banks et al., "Circulating intercellular adhesion molecule-1 (ICAM-1), E-selectin and vascular cell adhesion molecule-1 (VCAM-1) in human malignancies," Br. J. Cancer, 68:122-124, 1993.

Bates et al., "Neurotrophin-3 promotes cell death induced in cerebral ischemia, oxygen-glucose deprivation, and oxidative stress: possible involvement of oxygen free radicals," Neurobiology of Disease, :24-37, 2002.

Benamer et al., "Comparison of the prognostic value of C-reactive protein and troponin I in patients with unstable angina pectoris," Am. J. Cardiol., 82:845-850, 1998.

Berendes et al., "Secretion of brain natriuretic peptide in patients with aneurysmal subarachnoid haemorrhage," Lancet, 349:245-249, 1997.

Bialik et al., "Myocyte apoptosis during acute myocardinal infarction in the mouse localized to hypoxic regions but occurs independently of p53," J.Clin.Invest., 100(6): 1363-1372, 1997.

Biasucci et al., "Elevated levels of interleukin-6 in unstable angina," Circulation, 94:874-877, 1996.

Biasucci et al., "Episodic activation of the coagulation system in unstable angina does not elicit an acute phase reaction," Am. J. of Cardiol., 77:85-87, 1996.

Biasucci et al., "Increasing levels of interleukin (IL)-1Ra and IL-6 during the first 2 days of hospitalization in unstable angina are associated with increased risk of in-hospital coronary events," Circulation, 90:2079-2084, 1999.

Bitsch et al., "A longitudinal prospective study of soluble adhesion molecules in acute stroke," Stroke, 29:2129-2135, 198.

Blankaert et al., "Constitutive release of metalloproteinase-9 (92-kd Type IV collagenase) by Kaposi's sarcoma cells," J. Acquir. Immune Defic. Syndr. Hum. Retrovirol., 18:203-209, 1998.

Blann et al., "Soluble intercellular adhesion molecule-1, E-selectin, vascular cell adhesion molecule-1 and von Willebrand factor in stroke," Blood Coagul. Fibrinolysis, 10:277-284, 1999.

Bollensen et al., "Adenylate kinase enzyme activity in cases of brain infarction," Acta Neurol. Scand., 79:53-58, 1989.

Bonfrer et al., "The luminescence immunoassay S-100: a sensitive test to measure circulating S-100B: its prognostic value in malignant melanoma," Brit. Jour. Of Cancer, 77(12): 2210-2214, 1998.

Bonow, "New insights into the cardiac natriuretic peptides," Circulation, 93:1946-1950, 1996.

Bossink et al., "Plasma levels of the chemokines monocyte chemotactic proteins-1 and -2 are elevated in human sepsis," Blood, 86(10): 3841-3847, 1995.

Caligiuri et al., "Immune system activation follows inflammation in unstable angina: pathogenetic implications," J.Am. Coll. Cardiol., 32:1295-1304, 1998.

Carlstedt et al., "Proinflammatory cytokines, measured in a mixed population on arrival in the emergency department, are related to mortality and severity of disease," Journal of Internal Medicine, 242:361-365, 1997.

Carter et al., "Platelet GP IIIa P1A and GP lb variable number tandem repeat polymorphisms and markers of platelet activation in acute stroke," Arterioscler Thromb. Vasc. 18:1124-1131, 1998.

Carter et al., "Purification, cloning, expression and biological characterization of an interleukin-1 receptor antagonist protein," Nature, 344:633-638, 1990.

Catto et al., "von Willebrand factor and factor VIII: C in acute cerebrovascular disease," Thromb. Haemost., 77:1104-8, 1997.

Curzen et al., "Can C reactive protein or troponins T and I predict outcome in patients with intractable unstable angina?"Heart, 80:23-27, 1998.

Dangas et al., "Correlation of serum lipoprotein(a) with the angiographic and clinical presentation of coronary artery disease," Am. J. Cardiol., 83:583-585, 1999.

Davie et al., "The coagulation cascade: initiation, maintenance and regulation," Biochemistry, 30(43): 10363-10370, 1991.

DeRose et al., "Circulating adhesion molecules in cystic fibrosis," Am. J. Respir. Crit. Care Med., 157: 1234-1239, 1998.

Eisenberg et al., "Interleukin 1 receptor antagonist is a member of the interleukin 1 gene family: evolution of a cytokine control mechanism," Proc. Natl. Acad. Sci. USA, 88: 5232-5236, 1991.

Emsley et al., "Crystal structure of the von Willebrand factor A1 domain and implications for the binding of platelet glycoprotein lb," Journal of Biological Chemistry, 273(17): 10396-10401, 1998.

Endo et al., "Elevated levels of serum and plasma metalloproteinases in patients with gastric center," Anticancer Research, 17:2253-2258, 1997.

Estrada et al., "High plasma levels of endothelin-1 and atrial natriuretic peptide in patients with acute ischemic stroke," Am. J. of Hypertension, 7(12): 1085-1089, 1994.

Fassbender et al., "Proinflammatory cytokines in serum of patients with acute cerebral ischemia: kinetics of secretion and relation to the extent of brain damage and outcome of disease," Journal of the Neurological Sciences, 122:135-139, 1994.

Feinberg et al., "Hemostatic markers in acute ischemic stroke," Stroke, 27:1296-1300, 1996.

Fernandes-Alnemri et al., "CPP32, a novel human apoptotic protein with homology to Caenorhabditis elegans cell death protein Ced-3 and mammalian interleukin-1 β-converting enzyme," Journal of Biological Chemistry, 269(49): 30761-30764, 1994.

Fisher et al., "Serum concentrations and peripheral secretion of the beta chemokines monocyte chemoattractant protein 1 and macrophage inflammatory protein 1α in alcoholic liver disease," Gut, 45(3): 416-420, 1999.

Fon et al., "Hemostatic markers in acute transient ischemic attacks," Stroke, 25(2): 282-286, 1994.

Fujii et al., "Hemostasis in spontaneous subarachnoid hemorrhage," Neurosurgery, 37(2): 226-234, 1995.

Fujii et al., "Serial changes of hemostasis in aneurysmal subarachnoid hemorrhage with special reference to delayed ischemic neurological deficits," J.Neurosurg., 86:594-602, 1997.

Fujii et al., "Hemostasis in spontaneous subarachnoid hemorrhage." Neurosurgery, 37(2):226-234, 1995.

Gabay et al., "Interleukin 1 receptor antagonist (IL-1Ra) is an acute-phase protein," J.Clin. Invest., 99(12): 2930-2940, 1997.

George et al., "Evidence for altered hepatic matrix degradation in genetic haemochromatosis," Gut, 42: 715-720, 1998.

Gohji et al., "Elevation of serum levels of matrix metalloproteinase-2 and -3 as new predictors of recurrence in patients with urothelial carcinoma," Circulation, 99:608-613, 1999.

Goto et al., "Enhanced shear-induced platelet aggregation in acute myocardial infarction," Circulation, 99:608-613, 1999.

Guimaraes et al., "Potent constrictor actions of endothelin-1, endothelin-2, and endothelin-3 in rat isolated portal vein," Hypertension, 19(supp. 11): 1179-1186, 1992.

Hanley and McNeil, "The meaning and use of the area under a receiver operating characteristic (ROC) curve," Radiology, 143:29-36, 1982.

Hasegawa et al., "Increased levels of calbindin-D in serum and urine from patients treated by extracorporeal shock wave lithotripsy," Journal of Urology, 149:1414-1418, 1993.

Hayasake et al., "Elevated plasma levels of matrix metalloproteinase-9 (92-kd type IV collagenase/gelatinase B) in hepatocellular carcinoma," Hepatology, 24:1058-1062, 1996.

Heinrich et al., "Association of variables of coagulation, fibrinolysis and acute-phase with atherosclerosis in coronary and peripheral arteries and those arteries supplying the brain," Thrombosis and Haemostasis, 73(3): 374-379, 1995.

Hirashima et al., "Evolution of patelet activating factor, inflammatory cytokines, and coagulation factors in the internal jugular vein of patients with subarachnoid hemorrhage," Neurochem. Res., 22: 1249-1255, 1997.

Hirashima et al., "Cerebrospinal fluid tissue factor and thrombin-antithrombin III complex as indicators of tissue injury after subarachnoid hemorrhage," Stroke, 28:1666-1670, 1997.

Hunt et al., "The amino-terminal portion of Pro-brain natriuretic peptide (pro-BNP) circulates in human plasma," Biochem. Biophys. Res. Commun., 214:1175-1183, 1995.

Hwang et al., Circulating adhesion molecules VCAM-1, ICAM-1 and E-selectin in carotid atherosclerosis Circulation, 96:4219-4225, 1997.

Isgro et al., "A predictive parameter in patients with brain related complications after cardiac surgery," Eur. J. Cardiothorac. Surg., 11: 640-644, 1997.

Jacque et al., "Myelin basic protein in CSF and blood," Arch. Neurol., 39: 557-560, 1982.

James, T., "The variable morphological coexistence of apoptosis and necrosis in human myocardial infarction: significance for understanding its pathogenesis, clinical course, diagnosis and prognosis," Coron. Artery DIs., 9:291-307, 1998.

Jensen et al., Characterization of human brain S100 protein fraction: amino acid sequence of S100β, J. Neurochem., 45:700-705, 1985.

Johnson et al., "Activation of matrix-degrading metalloproteinases by mast cell proteases in atherosclerotic plaques," Arterioscler. Thromb. Vasc. Biol., 18:1707-1715, 1998.

Johnsson, "Markers of cerebral ischemia after cardiac surgery," J. Cardiothorac. Vasc. Anesth., 10: 120-126, 1996.

Jougasaki et al., "Adrenomedullin: potential in physiology and pathophysiology," Life Sciences, 66(10):855-872, 2000.

Kaneko et al., "Circulating levels of β-chemokines in systemis lupus erythematosus," J. Rheumatol., 26: 568-573, 1999.

Kario et al., "'Silent' cerebral infarction is associated with hypercoagulability, endothelial cell damage, and high Lp(a) levels in elderly Japanese," Arterioscler. Thromb. Vasc. Biol., 16: 734-741, 1996.

Keyszer et al., "Circulating levels of matrix metalloproteinases MMP-3 and MMP-1, tissue inhibitor of metalloproteinases 1 (TIMP-1), and MMP-1/TIMP-1 complex in rheumatic disease. Correlation with clinical activity of rheumatoid arthritis versus other surrogate markers," J.Rheumatol., 26:251-258, 1999.

Keyszer et al., "Matrix metalloproteinases, but not cathepsins B, H, and L or their inhibitors in peripheral blood of patients with rheumatoid arthritis are potentially useful markers of disease activity," J.Rheumatol., 57:392-398, 1998.

Kim et al., "Involvement of oxidative stress and caspase-3 in cortical infarction after photothrombotic ischemia in mice,". Cereb. Blood Flow Metab., 20:1690-1701, 2000.

Kim, "Cytokines and adhesion molecules in stroke and related diseases," J.Neurol. Sci., 137:69-78, 1996.

Kim et al., "Kidney as a major clearance oran for recombinant human interleukin-1 receptor antagonist," J.Pharm. Sci., 84:575-580, 1995.

Kim et al., "Serial measurement of interleukin-6, transforming growth factor-β, and S-100 protein in patients with acute stroke," Stroke, 27:1553-1557, 1996.

Koyama et al., "Determination of plasma tissue factor antigen and its clinical significance," Br. J. Haematol., 87:343-347, 1994.

Krupinski et al., "Protein kinase expression and activity in the human brain after ischaemic stroke," Acta Neurobiol. Exp. 58:13-21, 1998.

Kudo et al., "Clearance and tissue distribution of recombinaant human interleukin 1β in rats," Cancer Res., 50:5751-5755, 1990.

Kuwasako et al., "Increased plasma proadrenomedullin N-terminal 20 peptide in patients with essential hypertension," Ann. Clin. Biochem., 36:622-628, 1999.

Landi et al., "Hypercoagulability in acute stroke: prognostic significance." Neurol., 37: 1667-1671, 1987.

Laskowitz et al., "Serum markers of cerebral ischemia," J.Stroke Cerebrovasc. Dis., 7:234-241, 1998.

Latini et al., "Cytokines in acute myocardial infarction: selective increase in circulating tumor necrosis factor, its soluble receptor, and interleukin-1 receptor antagonist," J.Cardiovasc. Pharmacol., 23:1-6, 1994.

Lee and Bondy, "Insulin-like growth factors and cerebral ischemia," Ann. N.Y. Acad. Sci., 679:418-422, 1993.

Lee et al., "Proteolytic processing of big endothelin-3 by the kell blood group protein," Blood, 94:1440-50, 1999.

Legos et al., "Quantitative changes in interleukin proteins following focal stroke in the rat," Neurosci. Letter, 282:189-192, 2000.

Lein et al., "Metalloproteinasen (MMP-1, MMP-3) and ihre inhibitoren (TIMP) im blutplasma bei patienten mit prostatakarzinom," Urologe [A], 37:377-381, 1998.

Li et al., "The expression of monocyte chemotactic protein (MCP-1) in human vascular endothelium in vitro and in vivo," Mol. Cell. Biochem., 126:61-68, 1993.

Liu et al., "Purification and characterization of an interleukin-1β-converting enzyme family protease that activates cysteine protease P32 (CPP32)," J. Biol. Chem., 271:13371-13376, 1996.

Liuzzo et al., "Plasma protein acute-phase response in unstable angina is not induced by ischemic injury," Circulation, 94:2373-2380, 1996.

Long et al., "p53 and the hypoxia-induced apoptosis of cultured neonatal rat cardiac myocytes," J. Clin. Invest., 99:2635-2643, 1997.

Love et al., "Activation of caspase-3 in permanent and transient brain ischaemia in man," Neuroreport, 11:2495-2499, 2000.

Maiuri et al., "Serum and cerebrospinal fluid enzymes in subarachnoid haemorrhage," Neurol. Res., 11:6-8, 1989.

Manicourt et al., "Serum levels of collagenase, stromelysin-1, and TIMP-1," Arthritis Rheum., 37:1774-1783, 1994.

Martens et al., "Serum S-100 and neuron-specific enolase for prediction of regaining consciousness after global cerebral ischemia," Stroke, 29: 2363-2366, 1998.

Mateo and deArtinano, "Highlights of endothelins: A review," Pharm. Res., 36(5): 339-351, 1997.

Mathiesen et al., "Cerebrospinal fluid interleukin-1 receptor antagonist and tumor necrosis factor-α following subarachnoid," J.Neurosurg., 87:215-220, 1997.

Matsumori et al., "Plasma levels of the monocyte cnemotactic and activating factor/monocyte chemoattractant protein-1 are elevated in patients with acute myocardial infarction," J. Mol. Cell. Cardiol., 29:419-423, 1997.

McKeating et al., "Leukocyte adhesion molecule profiles and outcome after traumatic brain injury," Acta Neurochir. Suppl., 71:200-202, 1998.

McKeating et al., "Transcranial cytokine gradients in patients requiring intensive care after acute brain injury," Br. J. Anaesth., 78:520-523, 1997.

Missler et al., "S-100 protein and neuron-specific enolase concentrations in blood as indicators of infarction volume and prognosis in acute ischemic stroke," Stroke, 28, 1956-1960, 1997.

Miyata et al., "Conformational Changes in the A1 domain on von Willebrand factor modulating the interaction with platelet glycoprotein, Ibα," Biol. Chem., 271:9046-9053, 1996.

Montalescot et al., "Early increase of von WIllebrand factor predicts adverse outcome in unstable coronary artery disease," Circulation, 98:294-299.

Moore et al., "Collagenase expression in ovarian cancer cell lines," Gynecol. Oncol., 65:78-82, 1997.

Mori et al., "Vasodilator effects of C-type natriuretic peptide on cerebral arterioles in rats," Eur. J. Pharmacol., 320:183-186, 1997.

Mowla et al., "Biosynthesis and post-translational processing of the precursor to brain-derived neurotrophic factor," J.Biol. Chem., 276: 12660-12666, 2001.

Mun-Bryce and Rosenberg, "Matric metalloproteinases in cerebrovascular disease," J.Cereb. Blood Flow Metab., 18:1163-1172, 1998.

Niebroj-Dobosz et al., "Immunochemical analysis of some proteins in cerebrospinal fluid and serum of patients with ischemic strokes." Folia Neuropathol., 32: 129-137, 1994.

Nishiyama et al., "Simultaneous elevation of the levels of circulating monocyte chemoattractant protein-1 and tissue factor in acute coronary syndromes," Jpn. Circ. J., 62:710-712, 1998.

Nishizawa et al., "Protein kinase Cδ and α are invloved in the development of vasospasm after subarachnoid hemorrhage," Eur. J. Pharmacol., 398: 113-119, 2000.

Ohtsuka et al., "Clinical implications of circulating soluble Fas and Fas ligand in patients with acute myocardial infaction," Coron. Artery Dis., 10:221-225, 1999.

Oltrona et al., "C-Reactive protein elevation and early outcome in patients with unstable angina pectoris," Am. J. Cardiol., 80:1002-1006, 1997.

Otsuki et al., "Circulating vascular cell adhesion molecule-1 (VCAM-1) in atherosclerotic NIDDM patients," Diabetes, 46:2096-2101, 1997.

Persson et al., "S-100 protein and neuron-specific enolase in cerebrospinal fluid and serum: markers of cell damage in human central nervous system" Stroke, 18:911-918, 1987.

Phanithi et al., "Mild hypothermia post-ischemic neuronal death following focal cerebral ischemia in rat brain: Immunohistochemical study of Fas, caspase-3 and Tunel," Neuropathol., 20:273-282, 2000.

Polin et al., "Detection of soluble E-selectin, ICAM-1, VCAM-1, and L-selectin in the cerebrospinal fluid of patients after subarachnoid hemorrhage," J. Neurosurg,., 89:559-567, 1998.

Prickett et al., "Identification of amino-terminal pro-C-type natriuretic peptide in human plasma," Biochem. Biophys. Res. Commun., 286:513-517, 2001.

Quinn et al., "Mapping of antigenic sites in human neuron-specific enolase by expression subcloning," Clin. Chem., 40: 790-795, 1994.

Ray et al., "Predictive factors of tumor esponse and prognostic factors of survival during lung cancer chemotherapy," Cancer Detect. Prev., 22: 293-304, 1998.

Rebuzzi et al., "Incremental prognostic value of serum levels of troponin T and C-reactive protein on admission in patients with unstable angina pectoris," Am. J. Cardiol., 82:715-719, 1998.

Robey et al., "Binding of C-reactive protein to chromatin and nucleosome core particles," J. Biol. Chem., 259:7311-7316, 1984.

Romanic et al., "Matrix metalloproteinase expression increases after cerebral focal ischemia in rats," Stroke, 29:1020-1030, 1998.

Rosenberg, "Matrix metalloproteinases in brain injury," J.Neurotrauma, 12:833-842, 1995.

Rubattu et al., "The gene encoding atrial natriuretic peptide and the risk of human stroke," Circulation, 100:1722-1726, 1999.

Rucinski et al., "Clearance of human platelet factor 4 by liver and kidney: its alteration by heparin," Am. J. Ohysiol., 251: H800-H807, 1986.

Saraste A., "Morphologic criteria and detection of apoptosis," Herz., 24:189-195, 1999.

Schabiltz et al., "Intraventricular brain-derived neurotropic factor reduces infarct size after focal cerebral ischemia in rats," J.Cereb. Blood Flow Metab., 14: 500-506, 1997.

Schaller et al., "Elevated levels of head activator in human brain tumors and in serum of patients with brain and other neurally derived tumors," J.Neuro-Oncol., 6:251-258, 1988.

Schwab et al., "Plasma insulin-like growth facor I and IGF binding protein 3 levels in patients with acute cerebral ischemic injury," Stroke, 28:1744-1748, 1997.

Seki et al., "Sustained activation of blood coagulation in patients with cerebral thrombosis," A. J. Hematol., 50: 155-160, 1995.

Seki et al., "Plasma levels of thrombomodulin and lipoprotein (a) in patients with cerebral thrombosis," Blood Coagul. Fibrinolysis, 8:391-396, 1997.

Shyu et al., "Serum levels of intercellular adhesion molecule-1 and E-selectin in patients with acute ischaemic stroke," J. Neurol., 244:90-93, 1997.

Sixma et al., "Von Willebrand factor and the blood vessel wall," Mayo Clin. Proc., 66:628-633, 1991.

Skogseid et al., "Increased serum creatine kinase BB and neuron specific enolase following head injury indicates brain damage," Acta Neurochir (Wein), 115: 106-111, 1992.

Sorbi et al., "Elevated levels of 92-kd type IV collagenase (Matrix metalloproteinase 9) in giant cell arteritis," Arthritis Rheum., 39:1747-1753, 1996.

Steiner et al., "Increased levels of soluble adhesion molecules in Type 2 (Non-insulin dependent) diabetes mellitus are independent of glycaemic control," Thromb. Haemost., 72:979-984, 1994.

Stockman et al., "Secondary structure and topology of interleukin-1 receptor antagonist protein determined by heteronuclear three-dimensional NMR spectroscopy," Biohcemistry, 31:5237-5245, 1992.

Stroemer et al., "Cortical protection by localized striatal injection of IL-1ra following cerebral ischemia in the rat," J.Cereb. Blood Flow Metab., 17:597-604, 1997.

Suga et al., "Clinical significance of MCP-1 levels in BALF and serum in patients with interstitial lung diseases," Eur. Respir. J., 14:376-382, 1999.

Sviri et al., "Brain natriuretic peptide and cerebral vasospasm in subarachnoid hemorrhage: Clinical and TCD correlations," Stroke, 31:118-122, 2000.

Switalska et al., "Radioimmunoassay of human platelet thrombospondin: different patterns of thrombospondin and β-thromboglobulin antigen secretion and clearance from the circulation," J. Lab. Clin. Med., 106: 690-700, 1985.

Takahashi et al., "Tissue factor in plasma of patients with disseminated intravascular coagulation," Am. J. Hematol., 46:333-337, 1994.

Takano et al., "Markers of a hypercoagulable state following acute ischemic stroke," Stroke, 23:194-198, 1992.

Tateyama et al., "Concentrations and molecular forms of human brain natriuretic peptide in plasma," Biochem. Biophys. Res. Commun., 185:760-7, 1992.

Teitz Textbook of Clinical Chemistry, 2$^{nd}$ edition, Carl Burtis and Edward Ashwood eds. Philadelphia: W.B.Saunders and Company, p. 496.

Thomas et al., "Serum myelin basic protein, clinical responsiveness, and outcome of severe head injury," Acta Neurochir. Suppl., 28: 93-95, 1979.

Tohgi et al., "Coagulation-fibrinolysis abnormalities in acute and chronic phase of cerebral thrombosis and embolism," Stroke, 21: 1663-1667, 1990.

Tomida et al., "Plasma concentrations of brain natriuretic peptide in patients with subarachnoid hemmorrhage," Stroke, 29:1584-1587, 1998.

Tousoulis et al., "Von Willebrand factor in patients evolving Q-wave versus non-Q-wave acute myocardial infarction," Int. J. Cardiol., 56:259-262, 1996.

Trotter et al., "Immunoreactive myelin proteolipid protein-like activity in cerebrospinal fluid and serum of neurologically impaired patients," Ann. Neurol., 14: 554-558, 1983.

Uchiyama et al., "Alterations of platelet, coagulation, and fibrinolysis markers in patients with acute ischemic stroke," Semin. Thromb. Hemost., 23: 535-541, 1997.

Usui et al., "β-enolase in blood plasma during open heart surgery." J.Neurol., 123:134-139, 1994.

Wada et al., "Poor outcome in disseminated intravascular coagulation or thrombotic thrombocytopenic purpura patients with severe vascular endothelial cell injuries," Am. J. Hematol., 58:189-194, 1998.

Wang et al., "Monocyte chemoattractant protein-1 messenger RNA expression in rat ischemic cortex," Stroke, 26:661-665, 1995.

Wijdicks et al., "Natriuretic peptide system and endothelin in aneurysmal subarachnoid hemorrhage," J. Neurosurg., 87:275-280, 1997.

Wilkins et al., "The natriuretic-peptide family," Lancet, 349:1307-1310, 1997.

Winnikes et al., "Head activator as a potential serum marker for brain tumor analysis," Eur. J. Cancer, 28:421-424, 1992.

Woertgen et al., "Comparison of serial S-100 and NSE serum measurements after severe head injury," Acta Neurochir (Wien), 139: 1161-1165, 1997.

Yamagami et al., "Differential production of MCP-1 and cytokine-induced neutrophil chemoattractant in the ischemic brain after transient focal ischemia in rats," J. Leukoc. Biol., 65:744-749, 1999.

Yamazaki et al., "Alterations of haemostatic markers in various subtypes and phases of stroke," Blood Coagul., Fibrinolysis, 4:707-712, 1993.

Yang et al., "Overexpressing of interleukin-1 receptor antagonist in themouse brain reduces ischemic brain injury," Brain Res. 751: 181-188, 1997.

Yap et al., "Contraction to big endothelin-1, big endothelin-2 and big endothelin-3, and endothelin-converting enzyme inhibition in human isolated bronchi," Br. J. Pharmacol., 129:170-7, 2000.

Yazdani et al., "Percutaneous interventions after the hemostatic profile of patients with unstable versus stable angina," J. Am. Coll. Cardiol., 30:1284-1287, 1997.

Yoneda et al., "Identification of a novel adenylate kinase system in the brain: Cloning of the fourth adenylate kinase," Mol. Brain Res., 62: 187-195, 1998.

Yoshimura et al., "Human monocyte chemoattractant protein-1 (MCP-1)," FEBS Lett., 244:487-493, 1989.

Yoshitomi et al., "Plasma levels of adrenomedullin in patients with acute myocardial infarction," Clin. Sci. 94:135-9, 1998.

Zucker et al., "Increased serum stromelysin-1 levels in systemic lupus erythemalosus: lack of correlation with disease activity," J.Rheumatol., 26:78-80, 1999.

International Search Report and the Written Opinion of the International Searching Authority from PCT Application No. PCT/US04/12024.

Choudhri et al., "Targeted inhibition of intrinsic coagulation limits cerebral injury in stroke without increasing intracerebral hemorrhage." J.Exp.Med., 190:91-99, 1999.

Christenson et al., "Standardization of cardiac troponin I assays: Round robin of ten candidate reference materials." Clinical Chemistry, 47:431-437, 2001.

Zweig and Campbell, "Receiver-operating characteristic (ROC) plots: A Fundamental evaluation tool in clinical medicine." Clin. Chem., 39: 561-577, 1993.

Management of the Patient with stroke, Chapter One-Trends in stroke prevention and management http://69.3.158.146/nurse/courses/nurseweek/NW0200c1/c01.htm.

Allwords.com., Definition of "Appreciable".

Greenberg "Drug News and Perspectives", 1998, vol. 11, No. 5, pp. 265-270 Abstract Only.

Hunter et al., "Analysis of Peptides Derived from Pro Atrial Natriuretic Peptide That Circulate in Man an Increase in Heart Disease", Scand J. Clin Lab Invest 56, 205-216 (1998).

Mills et al., "Sustained Hemodynamic Effects of an Infusion of Nesiritide (Human b-Type Natriuretic Peptide) in Heart Failure", Journal of the American College of Cardiology, vol. 34, No. 1, pp. 155-162 (1999).

Venugopal, "Cardiac Natriuretic Peptides—Hope or Hype?", Journal of Clinical Pharmacy and therapeutics, vol. 26, No. 1, 15-31 (2001).

Vesley et al., "Negative Feedback of Atrial Natriuretic Peptides", Journal of Clinical Endocrinology and Metabolism, vol. 78, No. 5, 1128-1134 (1994).

Norman et al., "Degradation of Brain Natriuretic Peptide by Neutral Endopeptidase: Species Specific Sites of Proteolysis Determined by Mass Spectrometry", Biochemical & Biophysical Research Communications, vol. 175, No. 1, (1991).

Bidzseranova et al., "Structure-activity Studies on the Effects of Atrial Natriuretic Peptide, Brain Natriuretic Peptide and Their Analogs on Fear-motivated Learning Behavoir in Rats", Neuropeptides, 23, 61-65, (1992).

Baker, "In Biomarkes We Trust?", Nature Biotechnology, vol. 23, pp. 297-304, 2005.

Bast, Jr. et al., "Translational Crossroads For Biomarkers", Clin. Cancer Res., vol. 11, pp. 6103-6108, 2005.

Cala, Computerized axial tomography in the detection of brain damage. Medical Journal of Australia, 2(11): 616-620, 1980.

Carville et al., "thrombus Precursor Protein (TpP): Marker of Thrombosis Early in the Pathogenesis of Myocardial Infarction", Clinical Chemistry, vol. 42, pp. 1537-1541, 1996.

Corti et al., Vasopeptidase inhibitors: A New therapeutic concept in cardiovascular disease?, Circulation, 104:1856-1862, 2001.

Cuzzocrea et al., Effects of tempol, a membrane-permeable radical scavenger, in a gerbil model of brain injury. Brain Research, 875:96-106, 2000.

Duffus et al., "Glossary of Chemists of Terms used in Toxicology", Pure App. Chem., vol. 65, pp. 2003-2122, 1993.

European Search Report for EP Application No. 04781634.3-2401.

Futterman et al., Novel markers in the acute coronary syndrome: BNP, IL-6, PAPP-A, American Journal of Critical care, 11(2): 168-172 (2002).

Griffin et al., The inhibition of myeloperoxidase by ceruloplasmin can be reversed by anti-myeloperoxidase antibodies. Kidney International, 55:917-925, 1999.

Harrington, "The Role of MCP-1 in Atherosclerosis", Stem Cells, vol. 18, pp. 65-66, 2000.

Hayasaka et al., "Elevated Plasma Levels of Matrix Metalloproteinase-9 (92-kd type IV collagenase/gelatinase B) in Hepatocellular Carcinoma", Biochemical and Biophysical Research Communications, vol. 214, No., pp. 1058-1062, 1995.

Heeschen et al., "Troponin concentrations for Stratification of Patients with Acute Coronary Syndromes in Relation to Therapeutic Efficacy of Tirofiban", The Lancet, vol. 354, pp. 261-272, 2000.

Indik et al, "Detection of Pulmonary Embolism by D-Dimer Assays, Spiral Computed Tomography, and Magnetic Resonance Imaging", Process in Cardiovascular Diseases, vol. 42, pp. 261-272, 2000.

Jones et al., Hematopoietic stimulation by a dipeptidyl peptidase inhibitor reveals a novel regulatory mechanism and therapeutic treatment for blood cell deficiencies. Blood, 102(5): 1641-1648, 2003.

Kline et al., "New Diagnostic Test for Pulmonary embolism", Annals of Emergency Medicine, vol. 35, pp. 168-180, 2000.

Labaer et al., So, You Want To Look For Biomarkers:, J. Proteome Res., vol. 4, pp. 1053-1059, 2005.

Lindon, "Biomarkers: Present Concepts and Future Promise", Preclinica, vol. 1, pp. 221, 2003.

Minota et al., Circulating myeloperoxidase and anti-myeloperoxidase antibody in patients with vasculitis. Scand J Rheumatol, 28:94-99, 1999.

Montaner et al., "Matrix Metalloproteinase Expression after Human Cardioembolic Stroke", *Stroke*, pp. 1759-1766, Aug. 3, 2001.

Takebayashi et al., "Association Between Circulating Monocyte Chemoattractant Protein-1 and Urinary Albumin Excretion in Nonobese Type 2 Diabetic Patients", *J. Diabetes and Its Complications*, vol. 20, pp. 98-104, 2006.

Tervaert, The value of serial ANCA testing during follow-up studies in patients with ANCA-associated vasculitides: A review. Journal of Nephrology, 9(5): 232-240, 1996.

Vasan, "Biomarkers of Cardiovascular Disease: Molecular Basis and Practical Considerations", *Circulation*, vol. 113, pp. 2335-2362, 2006.

Walther et al., Biochemical analysis of neutral endopeptidase activity reveals independent catabolism of atrial and brain natriuretic peptide. Biol. Chem., 385: 179-184, Feb. 2004.

Zweig et al., "Receiver-Operating Characteristic (ROC) Plots: A Fundamental Evaluation Tool in Clinical Medicine", vol. 39, pp. 561-577, 1993.

International Search Report from International Application No. PCT/US04/26984.

* cited by examiner

```
                           SEQUENCE LISTING

<160> NUMBER OF SEQ ID NOS: 4

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 1
aggtgtcgta agcttgaatt cagacacctc tgccgccacc atgag              45

<210> SEQ ID NO 2
<211> LENGTH: 63
<212> TYPE: DNA
<213> ORGANISM: Artificial Sequence
<220> FEATURE:
<223> OTHER INFORMATION: Description of Artificial Sequence: Primer

<400> SEQUENCE: 2
gggctggctt acctgcggcc ttagtgatgg tgatggtgat ggtcctcagg gcactgcagg     60
atg                                                                  63

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
ttctcaagcc tcagacagtg                                                20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer
```

```
<400> SEQUENCE: 4
cctggatgca ggctactcta g                                                    21
```

DIAGNOSTIC MARKERS OF STROKE AND CEREBRAL INJURY AND METHODS OF USE THEREOF

RELATED APPLICATIONS

This application claims the benefit of U.S. Provisional Applications 60/313,775, filed Aug. 20, 2001, 60/334,964 filed Nov. 30, 2001, and 60/346,485, filed Jan. 2, 2002, the contents of each of which are hereby incorporated herein in their entirety.

FIELD OF THE INVENTION

The present invention relates to the identification and use of diagnostic markers for stroke and cerebral injury. In a various aspects, the invention relates to methods for the early detection and differentiation of stroke and transient ischemic attacks and the identification of individuals at risk for delayed neurological deficits upon presentation with stroke symptoms.

BACKGROUND OF THE INVENTION

The following discussion of the background of the invention is merely provided to aid the reader in understanding the invention and is not admitted to describe or constitute prior art to the present invention.

Stroke is a manifestation of vascular injury to the brain which is commonly secondary to atherosclerosis or hypertension, and is the third leading cause of death (and the second most common cause of neurologic disability) in the United States. Stroke can be categorized into two broad types, "ischemic stroke" and "hemorrhagic stroke." Additionally, a patient may experience transient ischemic attacks, which are in turn a high risk factor for the future development of a more severe episode.

Ischemic stroke encompasses thrombotic, embolic, lacunar and hypoperfusion types of strokes. Thrombi are occlusions of arteries created in situ within the brain, while emboli are occlusions caused by material from a distant source, such as the heart and major vessels, often dislodged due to myocardial infarct or atrial fibrillation. Less frequently, thrombi may also result from vascular inflammation due to disorders such as meningitis. Thrombi or emboli can result from atherosclerosis or other disorders, for example, arteritis, and lead to physical obstruction of arterial blood supply to the brain. Lacunar stroke refers to an infarct within non-cortical regions of the brain. Hypoperfusion embodies diffuse injury caused by non-localized cerebral ischemia, typically caused by myocardial infarction and arrhythmia.

The onset of ischemic stroke is often abrupt, and can become an "evolving stroke" manifested by neurologic deficits that worsen over a 24-48 hour period. In evolving stroke, symptoms commonly include unilateral neurologic dysfunction which extends progressively, without producing headache or fever. Evolving stroke may also become a "completed stroke," in which symptoms develop rapidly and are maximal within a few minutes.

Hemorrhagic stroke is caused by intracerebral or subarachnoid hemorrhage, i.e., bleeding into brain tissue, following blood vessel rupture within the brain. Intracerebral and subarachnoid hemorrhage are subsets of a broader category of hemorrhage referred to as intracranial hemorrhage. Intracerebral hemorrhage is typically due to chronic hypertension, and a resulting rupture of an arteriosclerotic vessel. Symptoms of intracerebral hemorrhage are abrupt, with the onset of headache and steadily increasing neurological deficits. Nausea, vomiting, delirium, seizures and loss of consciousness are common.

In contrast, most subarachnoid hemorrhage is caused by head trauma or aneurysm rupture which is accompanied by high pressure blood release which also causes direct cellular trauma. Prior to rupture, aneurysms may be asymptomatic, or occasionally associated with tension or migraine headaches. However, headache typically becomes acute and severe upon rupture, and may be accompanied by varying degrees of neurological deficit, vomiting, dizziness, and altered pulse and respiratory rates.

Transient ischemic attacks (TIAs) have a sudden onset and brief duration, typically 2-30 minutes. Most TIAs are due to emboli from atherosclerotic plaques, often originating in the arteries of the neck, and can result from brief interruptions of blood flow. The symptoms of TIAs are identical to those of stroke, but are only transient. Concomitant with underlying risk factors, patients experiencing TIAs are at a markedly increased risk for stroke.

Current diagnostic methods for stroke include costly and time-consuming procedures such as noncontrast computed tomography (CT) scan, electrocardiogram, magnetic resonance imaging (MRI), and angiography. Determining the immediate cause of stroke and differentiating ischemic from hemorrhagic stroke is difficult. CT scans can detect parenchymal bleeding greater than 1 cm and 95% of all subarachnoid hemorrhages. CT scan often cannot detect ischemic strokes until 6 hours from onset, depending on the infarct size. MRI may be more effective than CT scan in early detection of ischemic stroke, but it is less accurate at differentiating ischemic from hemorrhagic stroke, and is not widely available. An electrocardiogram (ECG) can be used in certain circumstances to identify a cardiac cause of stroke. Angiography is a definitive test to identify stenosis or occlusion of large and small cranial blood vessels, and can locate the cause of subarachnoid hemorrhages, define aneurysms, and detect cerebral vasospasm. It is, however, an invasive procedure that is also limited by cost and availability. Coagulation studies can also be used to rule out a coagulation disorder (coagulopathy) as a cause of hemorrhagic stroke.

Immediate diagnosis and care of a patient experiencing stroke can be critical. For example, tissue plasminogen activator (TPA) given within three hours of symptom onset in ischemic stroke is beneficial for selected acute stroke patients. Alternatively, patients may benefit from anticoagulants (e.g., heparin) if they are not candidates for TPA therapy. In contrast, thrombolytics and anticoagulants are strongly contraindicated in hemorrhagic strokes. Thus, early differentiation of ischemic events from hemorrhagic events is imperative. Moreover, delays in the confirmation of stroke diagnosis and the identification of stroke type limit the number of patients that may benefit from early intervention therapy. Finally, there are currently no diagnostic methods that can identify a TIA, or predict delayed neurological deficits which are often detected at a time after onset concurrent with the presentation of symptoms.

Accordingly, there is a present need in the art for a rapid, sensitive and specific diagnostic assay for stroke and TIA that can also differentiate the stroke type and identify those individuals at risk for delayed neurological deficits. Such a diagnostic assay would greatly increase the number of patients that can receive beneficial stroke treatment and therapy, and reduce the costs associated with incorrect stroke diagnosis.

BRIEF SUMMARY OF THE INVENTION

The present invention relates to the identification and use of diagnostic markers for stroke and cerebral injury. The methods and compositions described herein can meet the need in the art for rapid, sensitive and specific diagnostic assay to be used in the diagnosis and differentiation of various forms of stroke and TIAs. Moreover, the methods and compositions of the present invention can also be used to facilitate the treatment of stroke patients and the development of additional diagnostic and/or prognostic indicators.

In various aspects, the invention relates to materials and procedures for identifying markers that are associated with the diagnosis, prognosis, or differentiation of stroke and/or TIA in a patient; to using such markers in diagnosing and treating a patient and/or to monitor the course of a treatment regimen; to using such markers to identify subjects at risk for one or more adverse outcomes related to stroke and/or TIA; and for screening compounds and pharmaceutical compositions that might provide a benefit in treating or preventing such conditions.

In a first aspect, the invention discloses methods for determining a diagnosis or prognosis related to stroke, or for differentiating between types of strokes and/or TIA. These methods comprise analyzing a test sample obtained from a subject for the presence or amount of one or more markers for cerebral injury. These methods can comprise identifying one or more markers, the presence or amount of which is associated with the diagnosis, prognosis, or differentiation of stroke and/or TIA. Once such marker(s) are identified, the level of such marker(s) in a sample obtained from a subject of interest can be measured. In certain embodiments, these markers can be compared to a level that is associated with the diagnosis, prognosis, or differentiation of stroke and/or TIA. By correlating the subject's marker level(s) to the diagnostic marker level(s), the presence or absence of stroke, the probability of future adverse outcomes, etc., in a patient may be rapidly and accurately determined.

For purposes of the following discussion, the methods described as applicable to the diagnosis and prognosis of stroke generally may be considered applicable to the diagnosis and prognosis of TIAs.

In certain embodiments, a plurality of markers are combined to increase the predictive value of the analysis in comparison to that obtained from the markers individually or in smaller groups. Preferably, one or more non-specific markers for cerebral injury can be combined with one or more non-specific markers for cerebral injury to enhance the predictive value of the described methods.

The term "marker" as used herein refers to proteins or polypeptides to be used as targets for screening test samples obtained from subjects. "Proteins or polypeptides" used as markers in the present invention are contemplated to include any fragments thereof, in particular, immunologically detectable fragments. One of skill in the art would recognize that proteins which are released by cells of the central nervous system which become damaged during a cerebral attack could become degraded or cleaved into such fragments. Additionally, certain markers are synthesized in an inactive form, which may be subsequently activated by proteolysis. Examples of such markers are described hereinafter. The term "related marker" as used herein refers to one or more fragments of a particular marker that may be detected as a surrogate for the marker itself.

Preferred markers of the invention can differentiate between ischemic stroke, hemorrhagic stroke, and TIA. Particularly preferred are markers that differentiate between thrombotic, embolic, lacunar, hypoperfusion, intracerebral hemorrhage, and subarachnoid hemorrhage types of strokes.

Still other preferred markers of the invention can identify those subjects at risk for a subsequent adverse outcome. For example, a subset of subjects presenting with intracerebral hemorrhage or subarachnoid hemorrhage types of strokes may be susceptible to later vascular injury caused by cerebral vasospasm. In another example, a clinically normal subject may be screened in order to identify a risk of an adverse outcome. Preferred markers include caspase, NCAM, MCP-1, S100b, MMP-9, vWF, BNP, CRP, NT-3, VEGF, CKBB, MCP-1 Calbindin, thrombin-antithrombin III complex, IL-6, IL-8, myelin basic protein, tissue factor, GFAP, and CNP. Each of these terms are defined hereinafter. Particularly preferred markers are those predictive of a subsequent cerebral vasospasm in patients presenting with subarachnoid hemorrhage, such as von Willebrand factor, vascular endothelial growth factor, matrix metalloprotein-9, or combinations of these markers. Other particularly preferred markers are those that distinguish ischemic stroke from hemorrhagic stroke.

Such markers may be used individually, or as members of a marker "panel" comprising a plurality of markers that are measured in a sample, and used for determining a diagnosis or prognosis related to stroke, or for differentiating between types of strokes and/or TIA. Such a panel may be analyzed in a number of fashions well known to those of skill in the art. For example, each member of a panel may be compared to a "normal" value, or a value indicating a particular outcome. A particular diagnosis/prognosis may depend upon the comparison of each marker to this value; alternatively, if only a subset of markers are outside of a normal range, this subset may be indicative of a particular diagnosis/prognosis.

The sensitivity and specificity of a diagnostic test depends on more than just the "quality" of the test—they also depend on the definition of what constitutes an abnormal test. In practice, Receiver Operating Characteristic curves, or "ROC" curves, are typically calculated by plotting the value of a variable versus its relative frequency in "normal" and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker moves with the disease) the test is considered to be abnormal and below which the test is considered to be normal. The area under the ROC curve is a measure of the probability that the perceived measurement will allow correct identification of a condition. ROC curves can be used even when test results don't necessarily give an accurate numeric value for a marker level; that is, as long as one can rank results, one can create an appropriate ROC curve. Such methods are well known in the art. See, e.g., Hanley et al., Radiology 143: 29-36 (1982).

In preferred embodiments, particular thresholds for one or more markers in a panel are not relied upon to determine if a profile of marker levels obtained from a subject are indicative of a particular diagnosis/prognosis. Rather, the present invention may utilize an evaluation of the entire profile by plotting ROC curves for the sensitivity of a particular panel of markers versus 1-(specificity) for the panel at various cutoffs. In these methods, a profile of marker measurements from a subject is considered together to provide a global probability (expressed either as a numeric score or as a percentage risk) that an individual has had a stroke, is at risk for a stroke, the type of stroke (ischemic or hemorrhagic) which the individual has had or is at risk for, has had a TIA and not a stroke, etc. In such embodiments, an increase in a certain subset of markers may be sufficient to indicate a particular diagnosis/prognosis in one patient, while an increase in a different subset of markers may be sufficient to indicate the same or a different diagnosis/prognosis in another patient.

One or more markers may lack predictive value when considered alone, but when used as part of a panel, such markers may be of great value in determining a particular diagnosis/prognosis. Weighting factors may also be applied to one or more markers in a panel, for example, when a marker is of particularly high utility in identifying a particular diagnosis/prognosis. While the exemplary panels described herein can provide the ability to determine a diagnosis or prognosis related to stroke, or for differentiating between types of strokes and/or TIA, one or more markers may be replaced, added, or subtracted from these exemplary panels while still providing clinically useful results.

The term "test sample" as used herein refers to a sample of bodily fluid obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine and saliva. In addition, one of skill in the art would realize that some test samples would be more readily analyzed following a fractionation or purification procedure, for example, separation of whole blood into serum or plasma components.

The term "specific marker of cerebral injury" as used herein refers to proteins or polypeptides that are associated with brain tissue and neural cells, and which can be correlated with a cerebral injury, but are not correlated with other types of injury. Such specific markers of cerebral injury include adenylate kinase, brain-derived neurotrophic factor, calbindin-D, creatine kinase-BB, glial fibrillary acidic protein, lactate dehydrogenase, myelin basic protein, neural cell adhesion molecule, neuron-specific enolase, neurotrophin-3, proteolipid protein, S-100β, thrombomodulin, protein kinase C gamma, and the like. These specific markers are described in detail hereinafter.

The term "non-specific marker of cerebral injury" as used herein refers to proteins or polypeptides that are elevated in the event of cerebral injury, but may also be elevated due to non-cerebral events. Such markers may be typically be proteins related to coagulation and hemostasis or acute phase reactants. Factors in the activation of platelets and the mechanisms of coagulation include β-thromboglobulin, D-dimer, fibrinopeptide A, plasmin-α-2-antiplasmin complex, platelet factor 4, prothrombin fragment 1+2, thrombin-antithrombin III complex, tissue factor, and von Willebrand factor. Other non-specific markers include adrenomedullin, cardiac troponin I, head activator, hemoglobin $\alpha_2$ chain, caspase-3, vascular endothelial growth factor (VEGF), one or more endothelins (e.g., endothelin-1, endothelin-2, and endothelin-3), interleukin-8, A-type natriuretic peptide, B-type natriuretic peptide, and C-type natriuretic peptide. These non-specific markers are described in detail hereinafter.

The term "acute phase reactants" as used herein refers to proteins whose concentrations are elevated in response to stressful or inflammatory states that occur during various insults that include infection, injury, surgery, trauma, tissue necrosis, and the like. Acute phase reactant expression and serum concentration elevations are not specific for the type of insult, but rather as a part of the homeostatic response to the insult.

All acute phase reactants are produced in response to insult, perhaps in order to handle extensive insult, even though some components may not be needed. Examples of classical acute phase proteins include C-reactive protein, ceruloplasmin, fibrinogen, α1-acid glycoprotein, α1-antitrypsin, and haptoglobin. Various cytokines and related molecules such as insulin-like growth factor-1, interleukin-1β, interleukin-1 receptor antagonist, interleukin-6, transforming growth factor β, and tumor necrosis factor β are components of the inflammatory response that are also intimately involved in the acute phase reaction. Such cytokines are released into the bloodstream from the site of insult and are capable of themselves inducing expression of other acute phase proteins. Other acute phase reactants include E-selectin, intercellular adhesion molecule-1, matrix metalloproteinases (e.g., matrix metalloproteinase 9 (MMP-9)), monocyte chemotactic protein-1, vascular cell adhesion molecule, and the like.

The phrase "diagnosis" as used herein refers to methods by which the skilled artisan can estimate and/or determine whether or not a patient is suffering from a given disease or condition. The skilled artisan often makes a diagnosis on the basis of one or more diagnostic indicators, i.e., a marker, the presence, absence, or amount of which is indicative of the presence, severity, or absence of the condition.

Similarly, a prognosis is often determined by examining one or more "prognostic indicators." These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for experiencing a future stroke in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient. Preferred prognostic markers can predict the onset of delayed neurologic deficits in a patient after stroke, or the chance of future stroke.

The term "correlating," as used herein in reference to the use of diagnostic and prognostic indicators, refers to comparing the presence or amount of the indicator in a patient to its presence or amount in persons known to suffer from, or known to be at risk of, a given condition; or in persons known to be free of a given condition. As discussed above, a marker level in a patient sample can be compared to a level known to be associated with a specific type of stroke. The sample's marker level is said to have been correlated with a diagnosis; that is, the skilled artisan can use the marker level to determine whether the patient suffers from a specific type of stroke, and respond accordingly. Alternatively, the sample's marker level can be compared to a marker level known to be associated with a good outcome (e.g., the absence of stroke, etc.). In preferred embodiments, a profile of marker levels are correlated to a global probability or a particular outcome using ROC curves.

In certain embodiments, a diagnostic or prognostic indicator is correlated to a condition or disease by merely its presence or absence. In other embodiments, a threshold level of a diagnostic or prognostic indicator can be established, and the level of the indicator in a patient sample can simply be compared to the threshold level. A preferred threshold level for markers of the present invention is about 25 pg/mL, about 50 pg/mL, about 60 pg/mL, about 75 pg/mL, about 100 pg/mL, about 150 pg/mL, about 200 pg/mL, about 300 pg/mL, about 400 pg/mL, about 500 pg/mL, about 600 pg/mL, about 750 pg/mL, about 1000 pg/mL, and about 2500 pg/mL. The term "about" in this context refers to +/−10%.

In yet other embodiments, multiple determination of one or more diagnostic or prognostic markers can be made, and a temporal change in the marker can be used to determine a diagnosis or prognosis. For example, a diagnostic indicator may be determined at an initial time, and again at a second time. In such embodiments, an increase in the marker from the initial time to the second time may be diagnostic of a particular type of stroke, or a given prognosis. Likewise, a decrease in the marker from the initial time to the second time may be indicative of a particular type of stroke, or a given prognosis.

In yet another embodiment, multiple determinations of one or more diagnostic or prognostic markers can be made, and a temporal change in the marker can be used to monitor the efficacy of neuroprotective, thrombolytic, or other appropriate therapies. In such an embodiment, one might expect to see a decrease or an increase in the marker(s) over time during the course of effective therapy.

The skilled artisan will understand that, while in certain embodiments comparative measurements are made of the same diagnostic marker at multiple time points, one could also measure a given marker at one time point, and a second marker at a second time point, and a comparison of these markers may provide diagnostic information. Similarly, the skilled artisan will understand that serial measurements and changes in markers or the combined result over time may also be of diagnostic and/or prognostic value.

The phrase "determining the prognosis" as used herein refers to methods by which the skilled artisan can predict the course or outcome of a condition in a patient. The term "prognosis" does not refer to the ability to predict the course or outcome of a condition with 100% accuracy, or even that a given course or outcome is more likely to occur than not. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. For example, in individuals not exhibiting the condition, the chance of a given outcome may be about 3%. In preferred embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, and about a 95% chance. The term "about" in this context refers to +/−1%.

The skilled artisan will understand that associating a prognostic indicator with a predisposition to an adverse outcome is a statistical analysis. For example, a marker level of greater than 80 pg/mL may signal that a patient is more likely to suffer from an adverse outcome than patients with a level less than or equal to 80 pg/mL, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001. Exemplary statistical tests for associating a prognostic indicator with a predisposition to an adverse outcome are described hereinafter.

In other embodiments, a threshold degree of change in the level of a prognostic or diagnostic indicator can be established, and the degree of change in the level of the indicator in a patient sample can simply be compared to the threshold degree of change in the level. A preferred threshold change in the level for markers of the invention is about 5%, about 10%, about 15%, about 20%, about 25%, about 30%, about 50%, about 75%, about 100%, and about 150%. The term "about" in this context refers to +/−10%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In yet another aspect, the invention relates to methods for determining a treatment regimen for use in a patient diagnosed with stroke. The methods preferably comprise determining a level of one or more diagnostic or prognostic markers as described herein, and using the markers to determine a diagnosis for a patient. For example, a prognosis might include the development or predisposition to delayed neurologic deficits after stroke onset. One or more treatment regimens that improve the patient's prognosis by reducing the increased disposition for an adverse outcome associated with the diagnosis can then be used to treat the patient. Such methods may also be used to screen pharmacological compounds for agents capable of improving the patient's prognosis as above.

In another aspect, the invention relates to methods of identifying a patient at risk for cerebral vasospasm. Such methods preferably comprise comparing an amount of a marker predictive of a subsequent cerebral vasospasm, said marker selected from the group consisting of von Willebrand's factor (vWF), vascular endothelial growth factor (VEGF), and matrix metalloprotease-9 (MMP-9), in a test sample from a patient diagnosed with a subarachnoid hemorrhage to a predictive level of said marker, wherein said patient is identified as being at risk for cerebral vasospasm by a level of said marker equal to or greater than said predictive level.

In yet another aspect, the invention relates to methods of differentiating ischemic stroke from hemorrhagic stroke using such marker panels.

In a further aspect, the invention relates to kits for determining the diagnosis or prognosis of a patient. These kits preferably comprise devices and reagents for measuring one or more marker levels in a patient sample, and instructions for performing the assay. Optionally, the kits may contain one or more means for converting marker level(s) to a prognosis. Such kits preferably contain sufficient reagents to perform one or more such determinations, and/or Food and Drug Administration (FDA)-approved labeling.

DETAILED DESCRIPTION OF THE INVENTION

In accordance with the present invention, there are provided methods and compositions for the identification and use of markers that are associated with the diagnosis, prognosis, or differentiation of stroke and TIA in a subject. Such markers can be used in diagnosing and treating a subject and/or to monitor the course of a treatment regimen; for screening subjects for the occurrence or risk of a particular disease; and for screening compounds and pharmaceutical compositions that might provide a benefit in treating or preventing such conditions.

Stroke is a pathological condition with acute onset that is caused by the occlusion or rupture of a vessel supplying blood, and thus oxygen and nutrients, to the brain. The immediate area of injury is referred to as the "core," which contains brain cells that have died as a result of ischemia or physical damage. The "penumbra" is composed of brain cells that are neurologically or chemically connected to cells in the core. Cells within the penumbra are injured, but still have the ability to completely recover following removal of the insult caused during stroke. However, as ischemia or bleeding from hemorrhage continues, the core of dead cells can expand from the site of insult, resulting in a concurrent expansion of cells in the penumbra. The initial volume and rate of core expansion is related to the severity of the stroke and, in most cases, neurological outcome.

The brain contains two major types of cells, neurons and glial cells. Neurons are the most important cells in the brain, and are responsible for maintaining communication within the brain via electrical and chemical signaling. Glial cells function mainly as structural components of the brain, and they are approximately 10 times more abundant than neurons. Glial cells of the central nervous system (CNS) are astrocytes and oligodendrocytes. Astrocytes are the major interstitial cells of the brain, and they extend cellular processes that are intertwined with and surround neurons, isolating them from other neurons. Astrocytes can also form "end feet" at the end of their processes that surround capillaries. Oligodendrocytes are cells that form myelin sheathes around axons in the CNS. Each oligodendrocyte has the ability to ensheathe up to 50 axons. Schwann cells are glial cells of the peripheral nervous system (PNS). Schwann cells form myelin sheathes around axons in the periphery, and each Schwann cell ensheathes a single axon.

Cell death during stroke occurs as a result of ischemia or physical damage to the cells of the CNS. During ischemic stroke, an infarct occurs, greatly reducing or stopping blood flow beyond the site of infarction. The zone immediately beyond the infarct soon lacks suitable blood concentrations of the nutrients essential for cell survival. Cells that lack nutrients essential for the maintenance of important functions like metabolism soon perish. Hemorrhagic stroke can induce cell death by direct trauma, elevation in intracranial pressure, and the release of damaging biochemical substances in blood. When cells die, they release their cytosolic contents into the extracellular milieu.

The barrier action of tight junctions between the capillary endothelial cells of the central nervous system is referred to as the "blood-brain barrier". This barrier is normally impermeable to proteins and other molecules, both large and small. In other tissues such as skeletal, cardiac, and smooth muscle, the junctions between endothelial cells are loose enough to allow passage of most molecules, but not proteins.

Substances that are secreted by the neurons and glial cells (intracellular brain compartment) of the central nervous system (CNS) can freely pass into the extracellular milieu (extracellular brain compartment). Likewise, substances from the extracellular brain compartment can pass into the intracellular brain compartment. The passage of substances between the intracellular and extracellular brain compartments are restricted by the normal cellular mechanisms that regulate substance entry and-exit. Substances that are found in the extracellular brain compartment also are able to pass freely into the cerebrospinal fluid, and vice versa. This movement is controlled by diffusion.

The movement of substances between the vasculature and the CNS is restricted by the blood-brain barrier. This restriction can be circumvented by facilitated transport mechanisms in the endothelial cells that transport, among other substances, nutrients like glucose and amino acids across the barrier for consumption by the cells of the CNS. Furthermore, lipid-soluble substances such as molecular oxygen and carbon dioxide, as well as any lipid-soluble drugs or narcotics can freely diffuse across the blood-brain barrier.

Depending upon their size, specific markers of cerebral injury that are released from injured brain cells during stroke or other neuropathies will only be found in peripheral blood when CNS injury is coupled with or followed by an increase in the permeability of the blood-brain barrier. This is particularly true of larger molecules. Smaller molecules may appear in the peripheral blood as a result of passive diffusion, active transport, or an increase in the permeability of the blood-brain barrier. Increases in blood-brain barrier permeability can arise as a result of physical disruption in cases such as tumor invasion and extravasation or vascular rupture, or as a result of endothelial cell death due to ischemia. During stroke, the blood-brain barrier is compromised by endothelial cell death, and any cytosolic components of dead cells that are present within the local extracellular milieu can enter the bloodstream.

Therefore, specific markers of cerebral injury may also be found in the blood or in blood components such as serum and plasma, as well as the CSF of a patient experiencing stroke or TIAs. Furthermore, clearance of the obstructing object in ischemic stroke can cause injury from oxidative insult during reperfusion, and patients with ischemic stroke can sometimes experience hemorrhagic transformation as a result of reperfusion or thrombolytic therapy. Additionally, injury can be caused by vasospasm, which is a focal or diffuse narrowing of the large capacity arteries at the base of the brain following hemorrhage. The increase in blood-brain barrier permeability is related to the insult severity, and its integrity is reestablished following the resolution of insult. Specific markers of cerebral injury will only be present in peripheral blood if there has been a sufficient increase in the permeability of the blood-brain barrier that allows these large molecules to diffuse across. In this regard, most specific markers of cerebral injury can be found in cerebrospinal fluid after stroke or any other neuropathy that affects the CNS. Furthermore, many investigations of coagulation or fibrinolysis markers in stroke are performed using cerebrospinal fluid.

The Coagulation Cascade in Stroke

There are essentially two mechanisms that are used to halt or prevent blood loss following vessel injury. The first mechanism involves the activation of platelets to facilitate adherence to the site of vessel injury. The activated platelets then aggregate to form a platelet plug that reduces or temporarily stops blood loss. The processes of platelet aggregation, plug formation and tissue repair are all accelerated and enhanced by numerous factors secreted by activated platelets. Platelet aggregation and plug formation is mediated by the formation of a fibrinogen bridge between activated platelets. Concurrent activation of the second mechanism, the coagulation cascade, results in the generation of fibrin from fibrinogen and the formation of an insoluble fibrin clot that strengthens the platelet plug.

The coagulation cascade is an enzymatic pathway that involves numerous serine proteinases normally present in an inactive, or zymogen, form. The presence of a foreign surface in the vasculature or vascular injury results in the activation of the intrinsic and extrinsic coagulation pathways, respectively.

A final common pathway is then followed, which results in the generation of fibrin by the serine proteinase thrombin and, ultimately, a crosslinked fibrin clot. In the coagulation cascade, one active enzyme is formed initially, which can activate other enzymes that active others, and this process, if left unregulated, can continue until all coagulation enzymes are activated. Fortunately, there are mechanisms in place, including fibrinolysis and the action of endogenous proteinase inhibitors that can regulate the activity of the coagulation pathway and clot formation.

Fibrinolysis is the process of proteolytic clot dissolution. In a manner analogous to coagulation, fibrinolysis is mediated by serine proteinases that are activated from their zymogen form. The serine proteinase plasmin is responsible for the degradation of fibrin into smaller degradation products that are liberated from the clot, resulting in clot dissolution. Fibrinolysis is activated soon after coagulation in order to regulate clot formation. Endogenous serine proteinase inhibitors also function as regulators of fibrinolysis.

The presence of a coagulation or fibrinolysis marker in cerebrospinal fluid would indicate that activation of coagulation or fibrinolysis, depending upon the marker used, coupled with increased permeability of the blood-brain barrier has occurred. In this regard, more definitive conclusions regarding the presence of coagulation or fibrinolysis markers associated with acute stroke may be obtained using cerebrospinal fluid.

Platelets are round or oval disks with an average diameter of 2-4 µm that are normally found in blood at a concentration of 200,000-300,000/µl. They play an essential role in maintaining hemostasis by maintaining vascular integrity, initially stopping bleeding by forming a platelet plug at the site of vascular injury, and by contributing to the process of fibrin formation to stabilize the platelet plug. When vascular injury occurs, platelets adhere to the site of injury and each other and are stimulated to aggregate by various agents released from adherent platelets and injured endothelial cells. This is followed by the release reaction, in which platelets secrete the contents of their intracellular granules, and formation of the platelet plug. The formation of fibrin by thrombin in the coagulation cascade allows for consolidation of the plug, followed by clot retraction and stabilization of the plug by crosslinked fibrin. Active thrombin, generated in the concurrent coagulation cascade, also has the ability to induce platelet activation and aggregation.

The coagulation cascade can be activated through either the extrinsic or intrinsic pathways. These enzymatic pathways share one final common pathway. The result of coagulation activation is the formation of a crosslinked fibrin clot. Fibrinolysis is the process of proteolytic clot dissolution that is activated soon after coagulation activation, perhaps in an effort to control the rate and amount of clot formation. Urokinase-type plasminogen activator (uPA) and tissue-type plasminogen activator (tPA) proteolytically cleave plasminogen, generating the active serine proteinase plasmin. Plasmin proteolytically digests crosslinked fibrin, resulting in clot dissolution and the production and release of fibrin degradation products.

The first step of the common pathway of the coagulation cascade involves the proteolytic cleavage of prothrombin by the factor Xa/factor Va prothrombinase complex to yield active thrombin. Thrombin is a serine proteinase that proteolytically cleaves fibrinogen to form fibrin, which is ultimately integrated into a crosslinked network during clot formation.

Exemplary Markers (i) Specific Markers for Cerebral Injury

Adenylate kinase (AK) is a ubiquitous 22 kDa cytosolic enzyme that catalyzes the interconversion of ATP and AMP to ADP. Four isoforms of adenylate kinase have been identified in mammalian tissues (Yoneda, T. et al., *Brain Res Mol Brain Res* 62:187-195, 1998). The AK1 isoform is found in brain, skeletal muscle, heart, and aorta. The normal serum mass concentration of AK1 is currently unknown, because a functional assay is typically used to measure total AK concentration. The normal serum AK concentration is <5 units/liter and AK elevations have been performed using CSF (Bollensen, E. et al, *Acta Neurol Scand* 79:53-582, 1989). Serum AK1 appears to have the greatest specificity of the AK isoforms as a marker of cerebral injury. AK may be best suited as a cerebrospinal fluid marker of cerebral ischemia, where its dominant source would be neural tissue.

Neurotrophins are a family of growth factors expressed in the mammalian nervous system. Some examples include nerve growth factor (NGF), brain-derived neurotrophic factor (BDNF), neurotrophin-3 (NT-3) and neurotrophin-4/5 (NT-4/5). Neurotrophins exert their effects primarily as target-derived paracrine or autocrine neurotrophic factors. The role of the neurotrophins in survival, differentiation and maintenance of neurons is well known. They exhibit partially overlapping but distinct patterns of expression and cellular targets. In addition to the effects in the central nervous system, neurotrophins also affect peripheral afferent and efferent neurons.

BDNF is a potent neurotrophic factor which supports the growth and survivability of nerve and/or glial cells. BDNF is expressed as a 32 kDa precursor "pro-BDNF" molecule that is cleaved to a mature BDNF form. Mowla et al., *J. Biol. Chem.* 276: 12660-6 (2001). The most abundant active form of human BDNF is a 27 kDa homodimer, formed by two identical 119 amino acid subunits, which is held together by strong hydrophobic interactions; however, pro-BDNF is also released extracellularly and is biologically active. BDNF is widely distributed throughout the CNS and displays in vitro trophic effects on a wide range of neuronal cells, including hippocampal, cerebellar, and cortical neurons. In vivo, BDNF has been found to rescue neural cells from traumatic and toxic brain injury. For example, studies have shown that after transient middle cerebral artery occlusion, BDNF mRNA is upregulated in cortical neurons (Schabiltz et al., *J. Cereb. Blood Flow Metab.* 14:500-506, 1997). In experimentally induced focal, unilateral thrombotic stroke, BDNF mRNA was increased from 2 to 18 h following the stroke. Such results suggest that BDNF potentially plays a neuroprotective role in focal cerebral ischemia.

NT-3 is also a 27 kDa homodimer consisting of two 119-amino acid subunits. The addition of NT-3 to primary cortical cell cultures has been shown to exacerbate neuronal death caused by oxygen-glucose deprivation, possible via oxygen free radical mechanisms (Bates et al., *Neurobiol. Dis.* 9:24-37, 2002). NT-3 is expressed as an inactive pro-NT-3 molecule, which is cleaved to the mature biologically active form.

Calbindin-D is a 28 kDa cytosolic vitamin D-dependent $Ca^{2+}$-binding protein that may serve a cellular protective function by stabilizing intracellular calcium levels. Calbindin-D is found in the central nervous system, mainly in glial cells, and in cells of the distal renal tubule (Hasegawa, S. et al., *J. Urol.* 149:1414-1418, 1993). The normal serum concentration of calbindin-D is <20 pg/ml (0.7 pM). Serum calbindin-D concentration is reportedly elevated following cardiac arrest, and this elevation is thought to be a result of CNS damage due to cerebral ischemia (Usui, A. et al., *J. Neurol. Sci.* 123:134-139, 1994). Elevations of serum calbindin-D are elevated and plateau soon after reperfusion following ischemia. Maximum serum calbindin-D concentrations can be as much as 700 pg/ml (25 pM).

Creatine kinase (CK) is a cytosolic enzyme that catalyzes the reversible formation of ADP and phosphocreatine from ATP and creatine. The brain-specific CK isoform (CK-BB) is an 85 kDa cytosolic protein that accounts for approximately 95% of the total brain CK activity. It is also present in significant quantities in cardiac tissue, intestine, prostate, rectum, stomach, smooth muscle, thyroid uterus, urinary bladder, and veins (Johnsson, P. J., *Cardiothorac. Vasc. Anesth.* 10: 120-126, 1996). The normal serum concentration of CK-BB is <10 ng/ml (120 pM). Serum CK-BB is elevated after hypoxic and ischemic brain injury, but a further investigation is needed to identify serum elevations in specific stroke types (Laskowitz, D. T. et al., *J. Stroke Cerebrovasc. Dis.* 7:234-241, 1998). Elevations of CK-BB in serum can be attributed to cerebral injury due to ischemia, coupled with increased permeability of the blood brain barrier. No correlation of the serum concentration of CK-BB with the extent of damage (infarct volume) or neurological outcome has been established. CK-BB has a half-life of 1-5 hours in serum and is normally detected in serum at a concentration of <10 ng/ml (120 pM). In severe stroke, serum concentrations CK-BB are elevated and peak soon after the onset of stroke (within 24 hours), gradually returning to normal after 3-7 days (4). CK-BB concentrations in the serum of individuals with head injury peak soon after injury and return to normal between 3.5-12 hours after injury, depending on the injury severity (Skogseid, I. M. et al., *Acta Neurochir. (Wien.)* 115:106-111, 1992). Maximum serum CK-BB concentrations can exceed 250 ng/ml (3 nM). CK-BB may be best suited as a CSF marker of cerebral ischemia, where its dominant source would be neural tissue. CKBB might be more suitable as a serum marker of CNS damage after head injury because it is elevated for a short time in these individuals, with its removal apparently dependent upon the severity of damage.

Glial fibrillary acidic protein (GFAP) is a 55 kDa cytosolic protein that is a major structural component of astroglial filaments and is the major intermediate filament protein in astrocytes. GFAP is specific to astrocytes, which are interstitial cells located in the CNS and can be found near the blood-brain barrier. GFAP is not normally detected in serum. Serum GFAP is elevated following ischemic stroke (Niebroj-Dobosz, I., et al., *Folia Neuropathol.* 32:129-137, 1994). Current reports investigating serum GFAP elevations associated with stroke are severely limited, and much further investigation is needed to establish GFAP as a serum marker for all stroke types. Most studies investigating GFAP as a stroke marker have been performed using cerebrospinal fluid. Elevations of GFAP in serum can be attributed to cerebral injury due to ischemia, coupled with increased permeability of the blood brain barrier. No correlation of the serum concentration of GFAP with the extent of damage (infarct volume) or neurological outcome has been established. GFAP is elevated in cerebrospinal fluid of individuals with various neuropathies affecting the CNS, but there are no reports currently available describing the release of GFAP into the serum of individuals with diseases other than stroke (Albrechtsen, M. and Bock, E. J., *Neuroimmunol.* 8:301-309, 1985). Serum concentrations GFAP appear to be elevated soon after the onset of stroke, continuously increase and persist for an amount of time (weeks) that may correlate with the severity of damage. GFAP appears to a very specific marker for severe CNS injury, specifically, injury to astrocytes due to cell death caused by ischemia or physical damage.

Lactate dehydrogenase (LDH) is a ubiquitous 135 kDa cytosolic enzyme. It is a tetramer of A and B chains that catalyzes the reduction of pyruvate by NADH to lactate. Five isoforms of LDH have been identified in mammalian tissues, and the tissue-specific isoforms are made of different combinations of A and B chains. The normal serum mass concentration of LDH is currently unknown, because a functional assay is typically used to measure total LDH concentration. The normal serum LDH concentration is <600 units/liter (Ray, P. et al., *Cancer Detect. Prev.* 22:293-304, 1998). A great majority of investigations into LDH elevations in the context of stroke have been performed using cerebrospinal fluid, and elevations correlate with the severity of injury. Elevations in serum LDH activity are reported following both ischemic and hemorrhagic stroke, but further studies are needed in serum to confirm this observation and to determine a correlation with the severity of injury and neurological outcome (Aggarwal, S. P. et al., *J. Indian Med. Assoc.* 93:331-332, 1995; Maiuri, F. et al., *Neurol. Res.* 11:6-8, 1989). LDH may be best suited as a cerebrospinal fluid marker of cerebral ischemia, where its dominant source would be neural tissue.

Myelin basic protein (MBP) is actually a 14-21 kDa family of cytosolic proteins generated by alternative splicing of a single MBP gene that is likely involved in myelin compaction around axons during the myelination process. MBP is specific to oligodendrocytes in the CNS and in Schwann cells of the peripheral nervous system (PNS). It accounts for approximately 30% of the total myelin protein in the CNS and approximately 10% of the total myelin protein in the PNS. The normal serum concentration of MBP is <7 ng/ml (400 pM). Serum MBP is elevated after all types of severe stroke, specifically thrombotic stroke, embolic stroke, intracerebral hemorrhage, and subarachnoid hemorrhage, while elevations in MBP concentration are not reported in the serum of individuals with strokes of minor to moderate severity, which would include lacunar infarcts or transient ischemic attacks (Palfreyman, J. W. et al., *Clin. Chim. Acta* 92:403-409, 1979). Elevations of MBP in serum can be attributed to cerebral injury due to physical damage or ischemia caused by infarction or cerebral hemorrhage, coupled with increased permeability of the blood brain barrier. The serum concentration of MBP has been reported to correlate with the extent of damage (infarct volume), and it may also correlate with neurological outcome. The amount of available information regarding serum MBP elevations associated with stroke is limited, because most investigations have been performed using cerebrospinal fluid. MBP is normally detected in serum at an upper limit of 7 ng/ml (400 pM), is elevated after severe stroke and cerebral injury. Serum MBP is thought to be elevated within hours after stroke onset, with concentrations increasing to a maximum level within 2-5 days after onset. After the serum concentration reaches its maximum, which can exceed 120 ng/ml (6.9 nM), it can take over one week to gradually decrease to normal concentrations. Because the severity of damage has a direct effect on the release of MBP, it will affect the release kinetics by influencing the length of time that MBP is elevated in the serum. MBP will be present in the serum for a longer period of time as the severity of injury increases. The release of MBP into the serum of patients with head injury is thought to follow similar kinetics as those described for stroke, except that serum MBP concentrations reportedly correlate with the neurological outcome of individuals with head injury (Thomas, D. G. et al., *Acta Neurochir. Suppl. (Wien)* 28:93-95, 1979). The release of MBP into the serum of patients with intracranial tumors is thought to be persistent, but still needs investigation. Finally, serum MBP concentrations can sometimes be elevated in individuals with demyelinating diseases, but no conclusive investigations have been reported. As reported in individuals with multiple sclerosis, MBP is frequently elevated in the cerebrospinal fluid, but matched elevations in serum are often not present (Jacque, C. et al., *Arch. Neurol.* 39:557-560, 1982). This could indicate that cerebral damage has to be accompanied by an increase in the permeability of the blood-brain barrier to result in elevation of serum MBP concentrations. However, MBP can also be elevated in the population of individuals having intracranial tumors. The presence of these individuals in the larger population of individuals that would be candidates for an assay using this marker for stroke is rare. These individuals, in combination with individuals undergoing neurosurgical procedures or with demyelinating diseases, would nonetheless have an impact on determining the specificity of MBP for cerebral injury. Additionally, serum MBP may be useful as a marker of severe stroke, potentially identifying individuals that would not benefit from stroke therapies and treatments, such as tPA administration.

Neural cell adhesion molecule (NCAM), also called CD56, is a 170 kDa cell surface-bound immunoglobulin-like integrin ligand that is involved in the maintenance of neuronal and glial cell interactions in the nervous system, where it is expressed on the surface of astrocytes, oligodendrocytes, Schwann cells, neurons, and axons. NCAM is also localized to developing skeletal muscle myotubes, and its expression is upregulated in skeletal muscle during development, denervation and renervation. The normal serum mass concentration of NCAM has not been reported. NCAM is commonly measured by a functional enzyme immunoassay and is reported to have a normal serum concentration of <20 units/ml. Changes in serum NCAM concentrations specifically related to stroke have not been reported. NCAM may be best suited as a CSF marker of cerebral ischemia, where its dominant source would be neural tissue.

Enolase is a 78 kDa homo- or heterodimeric cytosolic protein produced from $\alpha$, $\beta$, and $\gamma$ subunits. It catalyzes the interconversion of 2-phosphoglycerate and phosphoenolpyruvate in the glycolytic pathway. Enolase can be present as $\alpha\alpha$, $\beta\beta$, $\alpha\gamma$, and $\gamma\gamma$ isoforms. The $\alpha$ subunit is found in glial cells and most other tissues, the $\beta$ subunit is found in muscle tissue, and the $\gamma$ subunit if found mainly in neuronal and neuroendocrine cells (Quinn, G. B. et al., *Clin. Chem.* 40:790-795, 1994). The $\gamma\gamma$ enolase isoform is most specific for neurons, and is referred to as neuron-specific enolase (NSE). NSE, found predominantly in neurons and neuroendocrine cells, is also present in platelets and erythrocytes. The normal serum concentration of NSE is <12.5 ng/ml (160 pM). NSE is made up of two subunits; thus, the most feasible immunological assay used to detect NSE concentrations would be one that is directed against one of the subunits. In this case, the $\gamma$ subunit would be the ideal choice. However, the $\gamma$ subunit alone is not as specific for cerebral tissue as the $\gamma\gamma$ isoform, since a measurement of the $\gamma$ subunit alone would detect both the $\alpha\gamma$ and $\gamma\gamma$ isoforms. In this regard, the best immunoassay for NSE would be a two-site assay that could specifically detect the $\gamma\gamma$ isoform. Serum NSE is reportedly elevated after all stroke types, including TIAs, which are cerebral in origin and are thought to predispose an individual to having a more severe stroke at a later date (Isgro, F. et al., *Eur. J. Cardiothorac. Surg.* 11:640-644, 1997). Elevations of NSE in serum can be attributed to cerebral injury due to physical damage or ischemia caused by infarction or cerebral hemorrhage, coupled with increased permeability of the blood brain barrier, and the serum concentration of NSE has been reported to correlate with the extent of damage (infarct volume) and neurological outcome (Martens, P. et al., *Stroke* 29:2363-2366, 1998). Additionally, a secondary elevation of serum NSE concentration may be an indicator of delayed neuronal injury resulting from cerebral vasospasm (Laskowitz, D. T. et al., *J. Stroke Cerebrovasc. Dis.* 7, 234-241, 1998). NSE, which has a biological half-life of 48 hours and is normally detected in serum at an upper limit of 12.5 ng/ml (160 pM), is elevated after stroke and cerebral injury. Serum NSE is elevated after 4 hours from stroke onset, with concentrations reaching a maximum 1-3 days after onset (Missler, U. et al., *Stroke* 28:1956-1960, 1997). After the serum concentration reaches its maximum, which can exceed 300 ng/ml (3.9 nM), it gradually decreases to normal concentrations over approximately one week. Because the severity of damage has a direct effect on the release of NSE, it will affect the release kinetics by influencing the length of time that NSE is elevated in the serum. NSE will be present in the serum for a longer period of time as the severity of injury increases. The release of NSE into the serum of patients with head injury follows different kinetics as seen with stroke, with the maximum serum concentration being reached within 1-6 hours after injury, often returning to baseline within 24 hours (Skogseid, I. M. et al., *Acta Neurochir. (Wien.)* 115:106-111, 1992). NSE is a specific marker for cerebral injury, specifically, injury to neuronal cells due to cell death caused by ischemia or physical damage. Neurons are about 10-fold less abundant in the brain than glial cells, so any cerebral injury coupled with increased permeability of the blood-brain barrier will have to occur in a region that has a significant regional population of neurons to significantly increase the serum NSE concentration. In addition, elevated serum concentrations of NSE can also indicate complications related to cerebral injury after AMI and cardiac surgery. Elevations in the serum concentration of NSE correlate with the severity of damage and the neurological outcome of the individual. NSE can be used as a marker of all stroke types, including TIAs. However, NSE cannot be used to differentiate ischemic and hemorrhagic stroke, and it is elevated in the population of individuals having tumors with neuroendocrine features.

Proteolipid protein (PLP) is a 30 kDa integral membrane protein that is a major structural component of CNS myelin. PLP is specific to oligodendrocytes in the CNS and accounts for approximately 50% of the total CNS myelin protein in the central sheath, although extremely low levels of PLP have been found (<1%) in peripheral nervous system (PNS) myelin. The normal serum concentration of PLP is <9 ng/ml (300 pM). Serum PLP is elevated after cerebral infarction, but not after transient ischemic attack (Trotter, J. L. et al., *Ann. Neurol.* 14:554-558, 1983). Current reports investigating serum PLP elevations associated with stroke are severely limited. Elevations of PLP in serum can be attributed to cerebral injury due to physical damage or ischemia caused by infarction or cerebral hemorrhage, coupled with increased permeability of the blood brain barrier. Correlation of the serum concentration of PLP with the extent of damage (infarct volume) or neurological outcome has not been established. No investigations examining the release kinetics of PLP into serum and its subsequent removal have been reported, but maximum concentrations approaching 60 ng/ml (2 nM) have been reported in encephalitis patients, which nearly doubles the concentrations found following stroke. PLP appears to a very specific marker for severe CNS injury, specifically, injury to oligodendrocytes. The available information relating PLP serum elevations and stroke is severely limited. PLP is also elevated in the serum of individuals with various neuropathies affecting the CNS. The undiagnosed presence of these individuals in the larger population of individuals that would be candidates for an assay using this marker for stroke is rare.

S-100 is a 21 kDa homo- or heterodimeric cytosolic $Ca^{2+}$-binding protein produced from α and β subunits. It is thought to participate in the activation of cellular processes along the Ca2+-dependent signal transduction pathway (Bonfrer, J. M. et al., *Br. J. Cancer* 77:2210-2214, 1998). S-100ao (αα isoform) is found in striated muscles, heart and kidney, S-100a (αβ isoform) is found in glial cells, but not in Schwann cells, and S-100b (ββ isoform) is found in high concentrations in glial cells and Schwann cells, where it is a major cytosolic component. The β subunit is specific to the nervous system, predominantly the CNS, under normal physiological conditions and, in fact, accounts for approximately 96% of the total S-100 protein found in the brain (Jensen, R. et al., *J. Neurochem.* 45:700-705, 1985). In addition, S-100β can be found in tumors of neuroendocrine origin, such as gliomas, melanomas, Schwannomas, neurofibromas, and highly differentiated neuroblastomas, like ganglioneuroblastoma and ganglioneuroma (Persson, L. et al., *Stroke* 18:911-918, 1987). The normal serum concentration of S-100β is <0.2 ng/ml (19 pM), which is the detection limit of the immunological detection assays used. Serum S-100β is elevated after all stroke types, including TIAs. Elevations of S-100β in serum can be attributed to cerebral injury due to physical damage or ischemia caused by infarction or cerebral hemorrhage, coupled with increased permeability of the blood-brain barrier, and the serum concentration of S-100β has been shown to correlate with the extent of damage (infarct volume) and neurological outcome (Martens, P. et al., *Stroke* 29:2363-2366, 1998; Missler, U. et al., *Stroke* 28:1956-1960, 1997). S-100β has a biological half-life of 2 hours and is not normally detected in serum, but is elevated after stroke and cerebral injury. Serum S-100β is elevated after 4 hours from stroke onset, with concentrations reaching a maximum 2-3 days after onset. After the serum concentration reaches its maximum, which can approach 20 ng/ml (1.9 mM), it gradually decreases to normal over approximately one week. Because the severity of damage has a direct effect on the release of S-100β, it will affect the release kinetics by influencing the length of time that S-100β is elevated in the serum. S-100β will be present in the serum for a longer period of time as the severity of injury increases. The release of S-100β into the serum of patients with head injury seems to follow somewhat similar kinetics as reported with stroke, with the only exception being that serum S-100β can be detected within 2.5 hours of onset and the maximum serum concentration is reached approximately 1 day after onset (Woertgen, C. et al., *Acta Neurochir. (Wien)* 139:1161-1164, 1997). S-100β is a specific marker for cerebral injury, specifically, injury to glial cells due to cell death caused by ischemia or physical damage. Glial cells are about 10 times more abundant in the brain than neurons, so any cerebral injury coupled with increased permeability of the blood-brain barrier will likely produce elevations of serum S-100β. Furthermore, elevated serum concentrations of S-100β can indicate complications related to cerebral injury after AMI and cardiac surgery. S-100β has been virtually undetectable in normal individuals, and elevations in its serum concentration correlate with the severity of damage and the neurological outcome of the individual. S-100β can be used as a marker of all stroke types, including TIAs. However, S-100β cannot be used to differentiate ischemic and hemorrhagic stroke, and it is elevated in the population of individuals having neuroendocrine tumors, usually in advanced stages.

Thrombomodulin (TM) is a 70 kDa single chain integral membrane glycoprotein found on the surface of vascular endothelial cells. TM demonstrates anticoagulant activity by changing the substrate specificity of thrombin. The formation of a 1:1 stoichiometric complex between thrombin and TM changes thrombin function from procoagulant to anticoagulant. This change is facilitated by a change in thrombin substrate specificity that causes thrombin to activate protein C (an inactivator of factor Va and factor VIIIa), but not cleave fibrinogen or activate other coagulation factors (Davie, E. W. et al., *Biochem.* 30:10363-10370, 1991). The normal serum concentration of TM is 25-60 ng/ml (350-850 pM). Current reports describing serum TM concentration alterations following ischemic stroke are mixed, reporting no changes or significant increases (Seki, Y. et al., *Blood Coagul. Fibrinolysis* 8:391-396, 1997). Serum elevations of TM concentration reflect endothelial cell injury and would not indicate coagulation or fibrinolysis activation.

The gamma isoform of protein kinase C (PKCg) is specific for CNS tissue and is not normally found in the circulation. PKCg is activated during cerebral ischemia and is present in the ischemic penumbra at levels 2-24-fold higher than in contralateral tissue, but is not elevated in infarcted tissue (Krupinski, J. et al., *Acta Neurobiol. Exp. (Warz)* 58:13-21, 1998). In addition, animal models have identified increased levels of PKCg in the peripheral circulation of rats following middle cerebral artery occlusion (Cornell-Bell, A. et al., Patent No. WO 01/16599 A1). Additional isoforms of PKC, beta I and beta II were found in increased levels in the infarcted core of brain tissue from patients with cerebral ischemia (Krupinski, J. et al., *Acta Neurobiol. Exp. (Warz)* 58:13-21, 1998). Furthermore, the alpha and delta isoforms of PKC (PKCa and PKCd, respectively) have been implicated in the development of vasospasm following subarachnoid hemorrhage using a canine model of hemorrhage. PKCd expression was significantly elevated in the basilar artery during the early stages of vasospasm, and PKCa was significantly elevated as vasospasm progressed (Nishizawa, S. et al., *Eur. J. Pharmacol.* 398:113-119, 2000). Therefore, it may be of benefit to measure various isoforms of PKC, either individually or in various combinations thereof, for the identification of cerebral damage, the presence of the ischemic penumbra, as well as the development and progression of cerebral vasospasm following subarachnoid hemorrhage. Ratios of PKC isoforms such as PKCg and either PKCbI, PKCbII, or both also may be of benefit in identifying a progressing stroke, where the ischemic penumbra is converted to irreversibly damaged infarcted tissue. In this regard, PKCg may be used to identify the presence and volume of the ischemic penumbra, and either PKCbI, PKCbII, or both may be used to identify the presence and volume of the infarcted core of irreversibly damaged tissue during stroke. PKCd, PKCa, and ratios of PKCd and PKCa may be useful in identifying the presence and progression of cerebral vasospasm following subarachnoid hemorrhage.

(ii) Non-specific Markers for Cerebral Injury Related to Coagulation

Plasmin is a 78 kDa serine proteinase that proteolytically digests crosslinked fibrin, resulting in clot dissolution. The 70 kDa serine proteinase inhibitor α2-antiplasmin (α2AP) regulates plasmin activity by forming a covalent 1:1 stoichiometric complex with plasmin. The resulting ~150 kDa plasmin-α2AP complex (PAP), also called plasmin inhibitory complex (PIC) is formed immediately after α2AP comes in contact with plasmin that is activated during fibrinolysis. The normal serum concentration of PAP is <1 µg/ml (6.9 nM).

Serum PAP concentration is significantly elevated following embolic and hemorrhagic stroke, but not thrombotic or lacunar stroke, and the magnitude of elevation correlates with the severity of injury and neurological outcome (Seki, Y. et al., *Am. J. Hematol.* 50:155-160, 1995; Yamazaki, M. et al., *Blood Coagul. Fibrinolysis* 4:707-712, 1993; Uchiyama, S. et al., *Semin. Thromb. Hemost.* 23:535-541, 1997; Fujii, Y. et al., *Neurosurgery* 37:226-234, 1995). There are no reports that identify elevations in serum PAP concentration following cerebral transient ischemic attacks. Elevations in the serum concentration of PAP can be attributed to the activation of fibrinolysis. Elevations in the serum concentration of PAP may be associated with clot presence, or any condition that causes or is a result of fibrinolysis activation. These conditions can include atherosclerosis, disseminated intravascular coagulation, AMI, surgery, trauma, unstable angina, and thrombotic thrombocytopenic purpura. PAP is formed immediately following proteolytic activation of plasmin. Serum PAP is increased in embolic and hemorrhagic stroke. Serum concentrations are elevated soon after stroke onset and may persist for over 2 weeks (Fujii, Y. et al., *J. Neurosurg.* 86:594-602, 1997). In addition, serum PAP concentration may be higher in hemorrhagic stroke than in ischemic stroke. This could reflect the increased magnitude of coagulation activation associated with hemorrhage. Serum concentrations of PAP associated with stroke can approach 6 μg/ml (41 nM). PAP is a specific marker for fibrinolysis activation and the presence of a recent or continual hypercoagulable state. It is not specific for stroke or cerebral injury and can be elevated in many other disease states. However, it may be possible to use PAP to differentiate hemorrhagic stroke from ischemic stroke, which would be beneficial in ruling out patients for thrombolytic therapy, and to identify embolic vs. non-embolic ischemic strokes.

β-thromboglobulin (βTG) is a 36 kDa platelet α granule component that is released upon platelet activation. The normal serum concentration of βTG is <40 ng/ml (1.1 nM). Serum βTG concentration is elevated following ischemic and hemorrhagic stroke (Landi, G. et al, *Neurol.* 37:1667-1671, 1987). Serum elevations were not found to correlate with injury severity or neurological outcome. Investigations regarding βTG serum elevations in stroke are severely limited. Elevations in the serum βTG concentration can be attributed to platelet activation, which could indirectly indicate the presence of vascular injury. Elevations in the serum concentration of βTG may be associated with clot presence, or any condition that causes platelet activation. These conditions can include atherosclerosis, disseminated intravascular coagulation, AMI, surgery, trauma, unstable angina, and thrombotic thrombocytopenic purpura. βTG is released into the circulation immediately after platelet activation and aggregation. It has a biphasic half-life of 10 minutes, followed by an extended 1 hour half-life in serum (Switaiska, H. I. et al., *J. Lab. Clin. Med.* 106:690-700, 1985). Serum βTG concentration is reported to be elevated in various stroke types, but these studies may not be completely reliable. Special precautions must be taken to avoid platelet activation during the blood sampling process. Platelet activation is common during regular blood sampling, and could lead to artificial elevations of serum βTG concentration. In addition, the amount of βTG released into the bloodstream is dependent on the platelet count of the individual, which can be quite variable. Serum concentrations of βTG associated with stroke can approach 70 ng/ml (2 nM). βTG is a specific marker of platelet activation, but it is not specific for stroke or cerebral injury and can be elevated in many other disease states.

Platelet factor 4 (PF4) is a 40 kDa platelet α granule component that is released upon platelet activation. PF4 is a marker of platelet activation and has the ability to bind and neutralize heparin. The normal serum concentration of PF4 is <7 ng/ml (175 pM). Serum PF4 concentration is marginally elevated following intracerebral infarction, but not in individuals with intracerebral hemorrhage (Carter, A. M. et al., *Arterioscler. Thromb. Vasc. Biol.* 18:1124-1131, 1998). Additionally, serum PF4 concentrations are increased 5-9 days following subarachnoid hemorrhage, which may be related to the onset of cerebral vasospasm (Hirashima, Y. et al., *Neurochem. Res.* 22:1249-1255, 1997). Investigations regarding PF4 serum elevations in stroke are severely limited. Elevations in the serum PF4 concentration can be attributed to platelet activation, which could indirectly indicate the presence of vascular injury. Elevations in the serum concentration of PF4 may be associated with clot presence, or any condition that causes platelet activation. These conditions can include atherosclerosis, disseminated intravascular coagulation, AMI, surgery, trauma, unstable angina, and thrombotic thrombocytopenic purpura. PF4 is released into the circulation immediately after platelet activation and aggregation. It has a biphasic half-life of 1 minute, followed by an extended 20 minute half-life in serum. The half-life of PF4 in serum can be extended to 20-40 minutes by the presence of heparin (Rucinski, B. et al., *Am. J. Physiol.* 251:H800-H807, 1986). Special precautions must be taken to avoid platelet activation during the blood sampling process. Serum concentrations of PF4 associated with stroke can exceed 200 ng/ml (5 nM), but it is likely that this value may be influenced by platelet activation during the sampling procedure. Furthermore, the serum PF4 concentration would be dependent on platelet count, requiring a second variable to be determined along with the concentration estimates. Finally, patients taking aspirin or other platelet activation inhibitors would compromise the clinical usefulness of PF4 as a marker of platelet activation.

Fibrinopeptide A (FPA) is a 16 amino acid, 1.5 kDa peptide that is liberated from amino terminus of fibrinogen by the action of thrombin. Fibrinogen is synthesized and secreted by the liver. The normal serum concentration of FPA is <4 ng/ml (2.7 nM). Serum FPA is elevated after all stroke types, including cerebral transient ischemic attacks (TIAs) (Fon, E. A. et al., *Stroke* 25:282-286, 1994; Tohgi, H.et al., *Stroke* 21:1663-1667, 1990; Landi, G. et al., *Neurol.* 37:1667-1671, 1987). Elevations of FPA in serum can be attributed to coagulation activation, and the serum concentration of FPA has been reported to correlate with the neurological outcome, but not the severity or extent of damage (infarct volume) (Feinberg, W. M. et al., *Stroke* 27:1296-1300, 1996). Elevations in the serum concentration of FPA are associated with any condition that causes or is a result of coagulation activation. These conditions can include AMI, surgery, cancer, disseminated intravascular coagulation, nephrosis, thrombotic thrombocytopenic purpura, and unstable angina. FPA is released into the bloodstream immediately upon clot formation and it can remain elevated for more than 1 month. Maximum serum FPA concentrations following stroke can exceed 50 ng/ml (34 nM).

Prothrombin fragment 1+2 is a 32 kDa polypeptide that is liberated from the amino terminus of thrombin during thrombin activation. The normal serum concentration of F1+2 is <32 ng/ml (1 mM). Serum F1+2 concentration is significantly elevated following lacunar stroke and hemorrhagic stroke (Kario, K. et al., *Arterioscler. Thromb. Vasc. Biol* 16:734-741, 1996; Fujii, Y. et al., *J. Neurosurg.* 86:594-602, 1997). No information is available regarding elevations in serum F1+2 concentration associated with other types of ischemic stroke or cerebral transient ischemic attacks. Serum elevations of F1+2 concentration reflect a state of coagulation activation, specifically, thrombin generation. Elevations in the serum concentration of F1+2 are associated with any condition that causes or is a result of coagulation activation. These conditions can include disseminated intravascular coagulation, AMI, surgery, trauma, unstable angina, and thrombotic thrombocytopenic purpura. F1+2 is released into the bloodstream immediately following thrombin activation. Serum F1+2 concentration is increased in lacunar and hemorrhagic stroke, but no information is available regarding the kinetics of release into the bloodstream and subsequent removal. F1+2 is a specific marker for coagulation activation and the presence of a general hypercoagulable state. It is not specific for stroke or cerebral injury, can be elevated in many disease states, and may even be artificially elevated by the blood sampling procedure. However, it may be possible to use F1+2 to differentiate hemorrhagic stroke from ischemic stroke, as it is possible that hemorrhagic stroke results in a greater activation of coagulation. Furthermore, patients with vascular injury, who may have a greatly elevated serum F1+2 concentration, should be ruled out for thrombolytic therapy that is commonly used in the early hours following embolic stroke. The infusion of tissue-type plasminogen activator (tPA) during thrombolytic therapy results in an activation of fibrinolysis, and the patient is unable to maintain blood clots. The administration of tPA an individual with vascular injury could ultimately result in hemorrhage.

Thrombin is a 37 kDa serine proteinase that proteolytically cleaves fibrinogen to form fibrin, which is ultimately integrated into a crosslinked network during clot formation. Antithrombin III (ATIII) is a 65 kDa serine proteinase inhibitor that is a physiological regulator of thrombin, factor XIa, factor XIIa, and factor IXa proteolytic activity. The inhibitory activity of ATIII is dependent upon the binding of heparin. Heparin enhances the inhibitory activity of ATIII by 2-3 orders of magnitude, resulting in almost instantaneous inactivation of proteinases inhibited by ATIII. ATIII inhibits its target proteinases through the formation of a covalent 1:1 stoichiometric complex. The normal serum concentration of the approximately 100 kDa thrombin-ATIII complex (TAT) is <5 ng/ml (50 pM). Serum TAT concentration is significantly elevated following embolic and hemorrhagic stroke, but not thrombotic or lacunar stroke, and the magnitude of elevation correlates with the severity of injury and neurological outcome (Takano, K. et al., *Stroke* 23:194-198, 1992; Fujii, Y. et al., *J. Neurosurg.* 86:594-602, 1997). Serum TAT concentrations may also be elevated following TIAs (Fon, E. A. et al., *Stroke* 25:282-286, 1994). Serum elevations of TAT concentration reflect a state of coagulation activation, specifically, thrombin generation. Elevations in the serum concentration of TAT are associated with any condition that causes or is a result of coagulation activation. These conditions can include disseminated intravascular coagulation, AMI, surgery, trauma, unstable angina, and thrombotic thrombocytopenic purpura. TAT is formed immediately following thrombin activation in the presence of heparin, which is the limiting factor in this interaction. Serum TAT, which has a half-life of 5 minutes, is increased in various stroke types. In hemorrhagic stroke, serum concentrations peak within 2 hours of onset, followed by a gradual decrease that reaches baseline 2-3 days after onset. (Fujii, Y. J., *Neurosurg.* 88:614-615, 1998). In addition, serum TAT concentration is frequently higher in hemorrhagic stroke than in ischemic stroke. This could reflect the increased magnitude of coagulation activation associated with hemorrhage. Serum TAT concentration associated with stroke can exceed 250 ng/ml (2.5 nM) (Fujii, Y. et al., *Neurosurgery* 37:226-234, 1995). TAT is a specific marker for coagulation activation and the presence of a general hypercoagulable state. It is not specific for stroke or cerebral injury, can be elevated in many disease states, and may even be artificially elevated by the blood sampling procedure. However, it may be possible to use TAT to differentiate hemorrhagic stroke from ischemic stroke within 12 hours of onset, and to identify embolic vs. non-embolic-ischemic strokes. Furthermore, patients with vascular injury, who may have a greatly elevated serum TAT concentration, should be ruled out for thrombolytic therapy that is commonly used in the early hours following embolic stroke. Finally, if a defined release pattern could be identified, measurement of TAT could be used to estimate the time elapsed since stroke onset.

D-dimer is a crosslinked fibrin degradation product with an approximate molecular mass of 200 kDa. The normal serum concentration of D-dimer is <150 ng/ml (750 pM). Serum D-dimer concentration is significantly elevated following embolic and hemorrhagic stroke, but not thrombotic or lacunar stroke, and the magnitude of elevation correlates with the severity of injury and neurological outcome (Feinberg, W. M. et al., *Stroke* 27:1296-1300, 1996; Takano, K. et al., *Stroke* 23:194-198, 1992; Fujii, Y. et al., *J. Neurosurg.* 86:594-602, 1997). Furthermore, serum D-dimer concentration is elevated following cerebral transient ischemic attacks (TIAs) (Fon, E. A. et al., *Stroke* 25:282-286, 1994). There is a major increase of serum D-dimer concentration 3 days after hemorrhagic stroke onset in individuals that experience vasospasm (Fujii, Y. et al., supra). Serum elevations of D-dimer concentration reflect a state of fibrinolysis activation, specifically, clot dissolution. Elevations in the serum concentration of D-dimer are associated with clot presence, or any condition that causes or is a result of fibrinolysis activation. These conditions can include atherosclerosis, disseminated intravascular coagulation, AMI, surgery, trauma, unstable angina, and thrombotic thrombocytopenic purpura (Heinrich, J. et al., *Thromb. Haemost.* 73:374-379, 1995; Wada, H. et al., *Am. J. Hematol.* 58:189-194, 1998). Serum concentrations are elevated soon after stroke onset and peak within 3 days, followed by a gradual decrease that reaches baseline>1 month after onset. In addition, serum concentration may be higher in hemorrhagic stroke than in ischemic stroke. This could reflect the increased magnitude of coagulation activation associated with hemorrhage. Serum concentrations of D-dimer associated with stroke can approach 3 µg/ml (15 nM). Because D-dimer is a specific marker for fibrinolysis activation and may indicate the presence of a recent or continual hypercoagulable state, it is not specific for stroke or cerebral injury and can be elevated in many other disease states. However, it may be possible to use D-dimer to differentiate hemorrhagic stroke from ischemic stroke, which would be beneficial in ruling out patients for thrombolytic therapy, and to identify embolic vs. non-embolic ischemic strokes. Furthermore, D-dimer may be used to detect delayed neurological deficits like hemorrhagic transformation of ischemic stroke and cerebral vasospasm following hemorrhagic stroke.

von Willebrand factor (vWF) is a plasma protein produced by platelets, megakaryocytes, and endothelial cells composed of 220 kDa monomers that associate to form a series of high molecular weight multimers. These multimers normally range in molecular weight from 600-20,000 kDa. vWF participates in the coagulation process by stabilizing circulating coagulation factor VIII and by mediating platelet adhesion to exposed subendothelium, as well as to other platelets. The A1 domain of vWF binds to binds to the platelet glycoprotein Ib-IX-V complex and non-fibrillar collagen type VI, and the A3 domain binds fibrillar collagen types I and III (Emsley, J. et al., *J. Biol. Chem.* 273:10396-10401, 1998). Other domains present in the vWF molecule include the integrin binding domain, which mediates platelet-platelet interactions, the protease cleavage domain, which appears to be relevant to the pathogenesis of type 11A von Willebrand disease. The interaction of vWF with platelets is tightly regulated to avoid interactions between vWF and platelets in normal physiologic conditions. vWF normally exists in a globular state, and it undergoes a conformation transition to an extended chain structure under conditions of high sheer stress, commonly found at sites of vascular injury. This conformational change exposes intramolecular domains of the molecule and allows vWF to interact with platelets. Furthermore, shear stress may cause vWF release from endothelial cells, making a larger number of vWF molecules available for interactions with platelets. The conformational change in vWF can be induced in vitro by the addition of non-physiological modulators like ristocetin and botrocetin (Miyata, S. et al., *J. Biol. Chem.* 271:9046-9053, 1996). At sites of vascular injury, vWF rapidly associates with collagen in the subendothelial matrix, and virtually irreversibly binds platelets, effectively forming a bridge between platelets and the vascular subendothelium at the site of injury. Evidence also suggests that a conformational change in vWF may not be required for its interaction with the subendothelial matrix (Sixma, J. J. and de Groot, P. G., *Mayo Clin. Proc.* 66:628-633, 1991). This suggests that vWF may bind to the exposed subendothelial matrix at sites of vascular injury, undergo a conformational change because of the high localized shear stress, and rapidly bind circulating platelets, which will be integrated into the newly formed thrombus. Measurement of the total amount of vWF would allow one who is skilled in the art to identify changes in total vWF concentration associated with stroke or cardiovascular disease. This measurement could be performed through the measurement of various forms of the vWF molecule. Measurement of the A1 domain would allow the measurement of active vWF in the circulation, indicating that a pro-coagulant state exists because the A1 domain is accessible for platelet binding. In this regard, an assay that specifically measures vWF molecules with both the exposed A1 domain and either the integrin binding domain or the A3 domain would also allow for the identification of active vWF that would be available for mediating platelet-platelet interactions or mediate crosslinking of platelets to vascular subendothelium, respectively. Measurement of any of these vWF forms, when used in an assay that employs antibodies specific for the protease cleavage domain may allow assays to be used to determine the circulating concentration of various vWF forms in any individual, regardless of the presence of von Willebrand disease. The normal plasma concentration of vWF is 5-10 µg/ml, or 60-110% activity, as measured by platelet aggregation. The measurement of specific forms of vWF may be of importance in any type of vascular disease, including stroke and cardiovascular disease. vWF concentrations have been demonstrated to be elevated in patients with stroke and subarachnoid hemorrhage, and also appear to be useful in assessing risk of mortality following stroke (Blann, A. et al., *Blood Coagul. Fibrinolysis* 10:277-284, 1999; Hirashima, Y. et al., *Neurochem. Res.* 22:1249-1255, 1997; Catto, A. J. et al., *Thromb. Hemost.* 77:1104-1108, 1997). The plasma vWF concentration also is reportedly elevated in individuals with AMI and unstable angina, but not stable angina (Goto, S. et al., *Circulation* 99:608-613, 1999; Tousoulis, D. et al., *Int. J. Cardiol.* 56:259-262, 1996; Yazdani, S. et al., *J. Am. Coll. Cardiol.* 30:1284-1287, 1997; Montalescot, G. et al., *Circulation* 98:294-299). Furthermore, elevations of the plasma vWF concentration may be a predictor of adverse clinical outcome in patients with unstable angina (Montalescot, G. et al., supra). The plasma concentration of vWF may be elevated in conjunction with any event that is associated with endothelial cell damage or platelet activation. vWF is present at high concentration in the bloodstream, and it is released from platelets and endothelial cells upon activation. vWF would likely have the greatest utility as a marker of platelet activation or, specifically, conditions that favor platelet activation and adhesion to sites of vascular injury. The conformation of vWF is also known to be altered by high shear stress, as would be associated with a partially stenosed blood vessel. As the blood flows past a stenosed vessel, it is subjected to shear stress considerably higher than what it encounters in the circulation of an undiseased individual. Another aspect of this invention measures the forms of vWF that arise from shear stress and the correlation of the forms to the presence of stroke.

Tissue factor is a 45 kDa cell surface protein expressed in brain, kidney, and heart, and in a transcriptionally regulated manner on perivascular cells and monocytes. TF forms a complex with factor VIIa in the presence of $Ca^{2+}$ ions, and it is physiologically active when it is membrane bound. This complex proteolytically cleaves factor X to form factor Xa. It is normally sequestered from the bloodstream. Tissue factor can be detected in the bloodstream in a soluble form, bound to factor VIIa, or in a complex with factor VIIa, and tissue factor pathway inhibitor that can also include factor Xa. The normal serum concentration of TF is <0.2 ng/ml (4.5 pM) (Albrecht, S. et al., *Thromb. Haemost.* 75:772-777, 1996). Serum TF concentration alterations following stroke have not been described. However, TF has been found in CSF following subarachnoid hemorrhage (Hirashima, Y. et al., *Stroke* 28:1666-1670, 1997). Elevations of TF in serum could be attributed to activation of the extrinsic coagulation pathway, and may indicate vascular injury. Elevations in the serum concentration of TF are associated with any condition that causes or is a result of coagulation activation through the extrinsic pathway. These conditions can include disseminated intravascular coagulation, ischemic heart disease, renal failure, vasculitis, and sickle cell disease (Takahashi, H. et al., *Am. J. Hematol.* 46:333-337, 1994; Koyama, T. et al., *Br. J. Haematol.* 87:343-347, 1994). TF is released immediately when vascular injury is coupled with extravascular cell injury. Further investigation is needed to determine the release kinetics of TF into serum and its subsequent removal associated with stroke.

(iii) Other Non-Specific Markers for Cerebral Injury

The appearance of non-specific serum markers of cellular injury related to stroke follow a pattern similar to those seen following acute myocardial infarction (AMI). Creatine kinase MB isoenzyme (CK-MB) is a cytosolic enzyme that is found in high concentrations in cardiac tissue, and is used as a serum marker for cardiac tissue damage from ischemia related to AMI following release from dying muscle cells into the bloodstream. Cardiac troponins I and T are cytoskeletal proteins in cardiac tissue myofibrils that are also released from damaged heart muscle related to cases of unstable angina and AMI. In addition, stroke and severe head trauma can cause life threatening arrhythmias and pulmonary edema which also cause cardiac troponin serum levels to increase. Finally, myoglobin is a heme protein found in muscle cells that is not specific for cardiac tissue, but is also elevated in the early stages of AMI.

Human vascular endothelial growth factor (VEGF) is a dimeric protein, the reported activities of which include stimulation of endothelial cell growth, angiogenesis, and capillary permeability. VEGF is secreted by a variety of vascularized tissues. In an oxygen-deficient environment, vascular endothelial cells may be damaged and may not ultimately survive. However, such endothelial damage stimulates VEGF production by vascular smooth muscle cells. Vascular endothelial cells may exhibit increased survival in the presence of VEGF, an effect that is believed to be mediated by expression of Bcl-2. VEGF can exist as a variety of splice variants known as VEGF(189), VEGF(165), VEGF(164), VEGFB(155), VEGF(148), VEGF(145), and VEGF(121).

Insulin-like growth factor-1 (IGF-1) is a ubiquitous 7.5 kDa secreted protein that mediates the anabolic and somatogenic effects of growth hormone during development (1, 2). In the circulation, IGF-1 is normally bound to an IGF-binding protein that regulates IGF activity. The normal serum concentration of IGF-1 is approximately 160 ng/ml (21.3 nM). Serum IGF-1 concentrations are reported to be significantly decreased in individuals with ischemic stroke, and the magnitude of reduction appears to correlate with the severity of injury (Schwab, S. et al., *Stroke* 28:1744-1748, 1997). Decreased IGF-1 serum concentrations have been reported in individuals with trauma and massive activation of the immune system. Due to its ubiquitous expression, serum IGF-1 concentrations could also be decreased in cases of non-cerebral ischemia. Interestingly, IGF-1 serum concentrations are decreased following ischemic stroke, even though its cellular expression is upregulated in the infarct zone (Lee, W. H. and Bondy, C., *Ann. N. Y. Acad. Sci.* 679:418-422, 1993). The decrease in serum concentration could reflect an increased demand for growth factors or an increased metabolic clearance rate. Serum levels were significantly decreased 24 hours after stroke onset, and remained decreased for over 10 days (Schwab, S. et al., *Stroke* 28:1744-1748, 1997). Serum IGF-1 may be a sensitive indicator of cerebral injury. However, the ubiquitous expression pattern of IGF-1 indicates that all tissues can potentially affect serum concentrations of IGF-1, compromising the specificity of any assay using IGF-1 as a marker for stroke. In this regard, IGF-1 may be best suited as a cerebrospinal fluid marker of cerebral ischemia, where its dominant source would be neural tissue.

Interleukin-1β (IL-1β) is a 17 kDa secreted proinflammatory cytokine that is involved in the acute phase response and is a pathogenic mediator of many diseases. IL-1β is normally produced by macrophages and epithelial cells. IL-1β is also released from cells undergoing apoptosis. The normal serum concentration of IL-1β is <30 pg/ml (1.8 pM). Serum IL-1β concentrations are found to only transiently increase after hemorrhagic stroke, and some reports indicate that serum concentrations of IL-1β are not elevated following ischemic stroke (Hirashima, Y. et al., *Neurochem. Res.* 22:1249-1255, 1997; Kim, J. S., *J. Neurol. Sci.* 137:69-78, 1996; Fassbender, K. et al., *J. Neurol. Sci.* 122:135-139, 1994; McKeating, E. G. et al., *Br. J. Anaesth.* 78:520-523, 1997). IL-1β is elevated in CSF after stroke. Elevations in serum IL-1β concentration would indicate activation of the immune system and cell death. Serum elevations of IL-1β are associated with any nonspecific proinflammatory condition such as trauma, infection, or other acute phase disease. Serum IL-1β has a biphasic half-life of 5 minutes followed by a prolonged 4 hour half-life (Kudo, S. et al., *Cancer Res.* 50:5751-5755, 1990). IL-1β protein expression is increased in neurons and glial cells within 1 hour of ischemia, remaining elevated for days (Kim, J. S., supra). It is possible that IL-1β is elevated only for a short time following stroke, and serum samples were not obtained within this time from onset. IL-1β may prove to be a useful marker of cell death as a result of cerebral injury in the early stages following stroke onset.

Interleukin-1 receptor antagonist (IL-1ra) is a 17 kDa member of the IL-1 family predominantly expressed in hepatocytes, epithelial cells, monocytes, macrophages, and neutrophils. IL-1ra has both intracellular and extracellular forms produced through alternative splicing. IL-1ra is thought to participate in the regulation of physiological IL-1 activity. IL-1ra has no IL-1-like physiological activity, but is able to bind the IL-1 receptor on T-cells and fibroblasts with an affinity similar to that of IL-1β, blocking the binding of IL-1α and IL-1β and inhibiting their bioactivity (Stockman, B. J. et al., *Biochemistry* 31:5237-5245, 1992; Eisenberg, S. P. et al., *Proc. Natl. Acad. Sci. U.S.A.* 88:5232-5236, 1991; Carter, D. B. et al., *Nature* 344:633-638, 1990). IL-1ra is normally present in higher concentrations than IL-1 in plasma, and it has been suggested that IL-1ra levels are a better correlate of disease severity than IL-1 (Biasucci, L. M. et al., *Circulation* 99:2079-2084, 1999). Furthermore, there is evidence that IL-1ra is an acute phase protein (Gabay, C. et al., *J. Clin. Invest.* 99:2930-2940, 1997). The normal plasma concentration of IL-1ra is <200 pg/ml (12 pM) (Biasucci, L. M. et al., supra). Earlier investigations using animal models have demonstrated that IL-1ra concentrations are elevated following cerebral ischemia, and there is evidence for elevations of IL-1ra in the cerebrospinal fluid of patients with subarachnoid hemorrhage (Legos, J. J. et al., *Neurosci. Lett.* 282:189-192, 2000; Mathiesen, T. et al., *J. Neurosurg.* 87:215-220, 1997). In addition, there is evidence that IL-1ra has a role in neuroprotection following cerebral ischemia (Yang, G. Y. et al., *Brain Res.* 751:181-188, 1997; Stroemer, R. P. and Rothwell, N. J., *J. Cereb. Blood Flow Metab.* 17:597-604, 1997). The plasma concentration of IL-1ra also is elevated in patients with AMI and unstable angina that proceeded to AMI, death, or refractory angina (Biasucci, L. M. et al., supra; Latini, R. et al., *J. Cardiovasc. Pharmacol.* 23:1-6, 1994). Furthermore, IL-1ra was significantly elevated in severe AMI as compared to uncomplicated AMI (Latini, R. et al., supra). Elevations in the plasma concentration of IL-1ra also are associated with any condition that involves activation of the inflammatory or acute phase response, including infection, trauma, and arthritis. IL-1ra is released into the bloodstream in pro-inflammatory conditions, and it may also be released as a participant in the acute phase response. The major sources of clearance of IL-1ra from the bloodstream appear to be kidney and liver (Kim, D. C. et al., *J. Pharm. Sci.* 84:575-580, 1995). Furthermore, it is likely released in conjunction with or soon after IL-1 release in pro-inflammatory conditions, and it is found at higher concentrations than IL-1. This indicates that IL-1ra may be a useful indirect marker of IL-1 activity, which elicits the production of IL-6. Thus, IL-1ra may be useful not only as a diagnostic marker for stroke, but also in the identification of the early stages of the acute phase response, before IL-6 concentrations are significantly elevated.

Interleukin-6 (IL-6) is a 20 kDa secreted protein that is a hematopoietin family proinflammatory cytokine. IL-6 is an acute-phase reactant and stimulates the synthesis of a variety of proteins, including adhesion molecules. Its major function is to mediate the acute phase production of hepatic proteins. IL-6 is normally produced by macrophages and T lymphocytes. The normal serum concentration of IL-6 is <10 pg/ml (0.5 pM). Serum IL-6 concentrations are elevated after both ischemic and hemorrhagic stroke (Fassbender, K. et al., *J. Neurol. Sci.* 122:135-139, 1994; Hirashima, Y. et al., *Neurochem. Res.* 22:1249-1255, 1997; Kim, J. S., *J. Neurol. Sci.* 137:69-78, 1996). It is not known if IL-6 concentrations are increased following TIAs. Interestingly, IL-6 is more significantly elevated in CSF following stroke, which may reflect IL-6 production in brain tissue, where it may have a neuroprotective role (Kim, J. S. J., supra). Serum elevations of IL-6 would indicate immune system activation of the acute phase response, and are reported to correlate with the severity of injury and neurological outcome. Serum elevations of IL-6 are associated with any nonspecific proinflammatory condition such as trauma, infection, or other acute phase diseases. Serum IL-6 has a half-life of approximately 2 hours and is elevated after stroke. Serum IL-6 concentrations are significantly elevated within 1 hour of stroke onset, reaching a plateau after 10 hours. This plateau is continued for 2.5 days, followed by a gradual return to basal levels over the next 4-5 days (Fassbender, K. et al., supra). Serum IL-6 concentration may be elevated for a longer period of time in individuals with hemorrhagic stroke. Maximum serum concentrations of IL-6 can exceed 300 pg/ml (15 pM). Serum IL-6 appears to be a sensitive marker of cerebral injury. Furthermore, the duration of serum IL-6 elevations may provide a means for distinguishing ischemic and hemorrhagic stroke.

Interleukin-8 (IL-8) is a 6.5 kDa chemokine produced by monocytes, endothelial cells, alveolar macrophages and fibroblasts. IL-8 induces chemotaxis and activation of neutrophils and T cells.

Transforming growth factor β (TGFβ) is a 25 kDa secreted homo- or heterotrimeric protein that is a TNFα antagonist and anti-inflammatory mediator. It also has both stimulatory and inhibitory effects on cellular proliferation and differentiation. TGFβ is normally produced by glial cells and neurons in the central nervous system, chondrocytes, monocytes, macrophages, and platelets. The normal serum concentration of TGFβ is approximately 120 ng/ml (4.8 nM). Serum TGFβ concentrations are reported to be decreased in individuals with ischemic and hemorrhagic stroke, and the magnitude did not significantly correlate with the severity of injury or neurological outcome (Kim, J. S. et al., Stroke 27:1553-1557, 1996). Decreased TGFβ serum concentrations could result from any nonspecific proinflammatory condition like trauma or infection, which would result in the consumption of TGFβ as a TNFα antagonist and anti-inflammatory agent. The serum concentration of TGFβ is decreased following stroke. The decrease in serum concentration could reflect an increased demand for TGFβ and other anti-inflammatory mediators in proinflammatory conditions. Serum levels were significantly decreased 24 hours and 3 days after stroke onset, and approached control values 7 days after onset. Further studies are needed to investigate changes in serum TGFβ concentration in the context of stroke. Serum TGFβ may be a sensitive marker of cerebral injury. However, the presence of a nonspecific proinflammatory condition can potentially affect serum concentrations of TGFβ. In this regard, TGFβ may be best suited as a CSF marker of cerebral ischemia, where its dominant source would be neural tissue. Furthermore, the serum TGFβ concentration appears to be only marginally decreased in stroke patients, and many factors that vary among individuals, including platelet count, can influence the serum TGFβ concentration.

Tumor necrosis factor α (TNFα) is a 17 kDa secreted proinflammatory cytokine that is involved in the acute phase response and is a pathogenic mediator of many diseases. TNFα is normally produced by macrophages and natural killer cells. The normal serum concentration of TNFα is <40 pg/ml (2 pM). Investigations into changes in serum TNFα concentrations following stroke have yielded mixed results (Carlstedt, F. et al., J. Intern. Med. 242:361-365, 1997; Fassbender, K. et al., J. Neurol. Sci. 122:135-139, 1994; Hirashinia, Y. et al., Neurochem. Res. 22:1249-1255, 1997; Kim, J. S., J. Neurol. Sci. 137:69-78, 1996; McKeating, E. G. et al., Br. J. Anaesth. 78:520-523, 1997). TNFα protein expression is increased in neurons and glial cells within 1 hour of ischemia, remaining elevated for days. It is possible that TNFα is elevated only for a short time following stroke, and serum samples were not obtained within this time from onset. Serum elevations of TNFα are associated with any nonspecific proinflammatory condition such as trauma, infection, or other acute phase disease. Serum TNFα has a half-life of approximately 1 hour, and maximum serum concentrations can exceed 7.5 ng/ml (375 pM). Elevations of the serum concentration of TNFα likely indicate activation of the immune system acute phase response.

C-reactive protein is a (CRP) is a homopentameric $Ca^{2+}$-binding acute phase protein with 21 kDa subunits that is involved in host defense. CRP preferentially binds to phosphorylcholine, a common constituent of microbial membranes. Phosphorylcholine is also found in mammalian cell membranes, but it is not present in a form that is reactive with CRP. The interaction of CRP with phosphorylcholine promotes agglutination and opsonization of bacteria, as well as activation of the complement cascade, all of which are involved in bacterial clearance. Furthermore, CRP can interact with DNA and histones, and it has been suggested that CRP is a scavenger of nuclear material released from damaged cells into the circulation (Robey, F. A. et al., J. Biol. Chem. 259:7311-7316, 1984). CRP synthesis is induced by Il-6, and indirectly by IL-1, since IL-1 can trigger the synthesis of IL-6 by Kupffer cells in the hepatic sinusoids. The normal plasma concentration of CRP is <3 µg/ml (30 nM) in 90% of the healthy population, and <10 µg/ml (100 nM) in 99% of healthy individuals. Plasma CRP concentrations can be measured by rate nephelometry or ELISA. The plasma concentration of CRP is significantly elevated in patients with AMI and unstable angina, but not stable angina (Biasucci, L. M. et al., Circulation 94:874-877, 1996; Biasucci, L. M. et al., Am. J. Cardiol. 77:85-87, 1996; Benamer, H. et al., Am. J. Cardiol. 82:845-850, 1998; Caligiuri, G. et al., J. Am. Coll. Cardiol. 32:1295-1304, 1998; Curzen, N. P. et al., Heart 80:23-27, 1998; Dangas, G. et al., Am. J. Cardiol. 83:583-5, A7, 1999). CRP may also be elevated in the plasma of individuals with variant or resolving unstable angina, but mixed results have been reported (Benamer, H. et al., supra; Caligiuri, G. et al., J. Am. Coll. Cardiol. 32:1295-1304, 1998). CRP may not be useful in predicting the outcome of patients with AMI or unstable angina (Curzen, N. P. et al., Heart 80:23-27, 1998; Rebuzzi, A. G. et al., Am. J. Cardiol. 82:715-719, 1998; Oltrona, L. et al., Am. J. Cardiol. 80:1002-1006, 1997). The concentration of CRP will be elevated in the plasma from individuals with any condition that may elicit an acute phase response, such,as infection, surgery, trauma, and stroke. CRP is a secreted protein that is released into the bloodstream soon after synthesis. CRP synthesis is upregulated by IL-6, and the plasma CRP concentration is significantly elevated within 6 hours of stimulation (Biasucci, L. M. et al., supra). The plasma CRP concentration peaks approximately 50 hours after stimulation, and begins to decrease with a half-life of approximately 19 hours in the bloodstream (Biasucci, L. M. et al., Am. J. Cardiol., supra). Other investigations have confirmed that the plasma CRP concentration in individuals with unstable angina (Biasucci, L. M. et al., supra). The plasma concentration of CRP can approach 100 µg/ml (1 µM) in individuals with ACS (Biasucci, L. M. et al., supra; Liuzzo, G. et al., Circulation 94:2373-2380, 1996). CRP is a specific marker of the acute phase response. Elevations of CRP have been identified in the plasma of individuals with AMI and unstable angina, most likely as a result of activation of the acute phase response associated with atherosclerotic plaque rupture or cardiac tissue injury. CRP is a highly nonspecific marker for ACS, and elevations of the CRP concentration in plasma may occur from unrelated conditions involving activation of the immune system. Despite its high degree of non-specificity for ACS, CRP may be useful in the identification of unstable angina and AMI when used with another marker that is specific for cardiac tissue injury. Plasma has a high concentration of CRP and there is much variability in the reported concentration of CRP in the blood of healthy individuals. Further investigation using a uniform assay, most likely a competitive immunoassay, on a range of plasma samples is necessary to determine the upper limits of the concentration of CRP in the plasma of apparently healthy individuals.

Adhesion molecules are involved in the inflammatory response can also be considered as acute phase reactants, as their expression levels are altered as a result of insult. Examples of such adhesion molecules include E-selectin, intercellular adhesion molecule-1, vascular cell adhesion molecule, and the like.

E-selectin, also called ELAM-1 and CD62E, is a 140 kDa cell surface C-type lectin expressed on endothelial cells in response to IL-1 and TNFα that mediates the "rolling" interaction of neutrophils with endothelial cells during neutrophil recruitment. The normal serum concentration of E-selectin is approximately 50 ng/ml (2.9 nM). Investigations into the changes on serum E-selectin concentrations following stroke have reported mixed results. Some investigations report increases in serum E-selectin concentration following ischemic stroke, while others find it unchanged (Bitsch, A. et al., *Stroke* 29:2129-2135, 1998; Kim, J. S., *J. Neurol. Sci.* 137:69-78, 1996; Shyu, K. G. et al., *J. Neurol.* 244:90-93, 1997). E-selectin concentrations are elevated in the CSF of individuals with subarachnoid hemorrhage and may predict vasospasm (Polin, R. S. et al., *J. Neurosurg.* 89:559-567, 1998). Elevations in the serum concentration of E-selectin would indicate immune system activation. Serum E-selectin concentrations are elevated in individuals with, atherosclerosis, various forms of cancer, preeclampsia, diabetes, cystic fibrosis, AMI, and other nonspecific inflammatory states (Hwang, S. J. et al., *Circulation* 96:4219-4225, 1997; Banks, R. E. et al., *Br. J. Cancer* 68:122-124, 1993; Austgulen, R. et al., *Eur. J. Obstet. Gynecol. Reprod. Biol.* 71:53-58, 1997; Steiner, M. et al., *Thromb. Haemost.* 72:979-984, 1994; De Rose, V. et al., *Am. J. Respir. Crit. Care Med.* 157:1234-1239, 1998). The serum concentration of E-selectin may be elevated following ischemic stroke, but it is not clear if these changes are transient or regulated by an as yet unidentified mechanism. Serum E-selectin may be a specific marker of endothelial cell injury. It is not, however, a specific marker for stroke or cerebral injury, since it is elevated in the serum of individuals with various conditions causing the generation of an inflammatory state. Furthermore, elevation of serum E-selectin concentration is associated with some of the risk factors associated with stroke.

Intercellular adhesion molecule (ICAM-1), also called CD54, is a 85-110 kDa cell surface-bound immunoglobulin-like integrin ligand that facilitates binding of leukocytes to antigen-presenting cells and endothelial cells during leukocyte recruitment and migration. ICAM-1 is normally produced by vascular endothelium, hematopoictic stem cells and non-hematopoietic stem cells, which can be found in intestine and epidermis. The normal serum concentration of ICAM-1 is approximately 250 ng/ml (2.9 nM). Investigations into the changes on serum ICAM-1 concentrations following stroke have reported mixed results (Kim, J. S., *J. Neurol. Sci.* 137:69-78, 1996; Laskowitz, D. T. et al., *J. Stroke Cerebrovasc. Dis.* 7:234-241, 1998). Most reports indicate that serum ICAM-1 concentration is elevated following ischemic stroke, but not cerebral transient ischemic attacks, and no correlation between serum concentrations and the severity of injury or neurological outcome has been established (Bitsch, A. et al., *Stroke* 29:2129-2135, 1998; Shyu, K. G. et al., *J. Neurol.* 244:90-93, 1997). ICAM-1 concentrations are also elevated in the CSF of patients with subarachnoid hemorrhage (Polin, R. S. et al., *J. Neurosurg.* 89:559-567, 1998). Increases in the serum concentration of ICAM-1 would indicate activation of the immune system. Serum ICAM-1 concentrations are elevated in individuals with head trauma, atherosclerosis, various forms of cancer, preeclampsia, multiple sclerosis, cystic fibrosis, AMI, and other nonspecific inflammatory states (McKeating, E. G. et al., *Acta Neurochir. Suppl.* (*Wien*) 71:200-202, 1998; Hwang, S. J. et al.. *Circulation* 96:4219-4225, 1997; Banks, R. E. et al., *Br. J. Cancer* 68:122-124, 1993; Austgulen, R. et al., *Eur. J. Obstet. Gynecol. Reprod. Biol.* 71:53-58, 1997; De Rose, V. et al., *Am. J. Respir. Crit. Care Med.* 157:1234-1239, 1998). The serum concentration of ICAM-1 is elevated following ischemic stroke. Serum concentrations peak within 24 hours of onset and gradually return to normal values within 5 days (Bitsch, A. et al., supra). Serum ICAM-1 concentrations can exceed 400 ng/ml (4.6 nM) in individuals with stroke (Polin, R. S. et al., supra). Further studies are needed to investigate changes in serum ICAM-1 concentration in the context of stroke. Serum ICAM-1 is a very nonspecific marker of cerebral injury, since it is elevated in the serum of individuals with various conditions causing the generation of an inflammatory state. Furthermore, elevation of serum ICAM-1 concentration is associated with some of the risk factors associated with stroke.

Vascular cell adhesion molecule (VCAM), also called CD106, is a 100-110 kDa cell surface-bound immunoglobulin-like integrin ligand that facilitates binding of B lymphocytes and developing T lymphocytes to antigen-presenting cells during lymphocyte recruitment. VCAM is normally produced by endothelial cells, which line blood and lymph vessels, the heart, and other body cavities. The normal serum concentration of VCAM is approximately 650 ng/ml (6.5 nM). Serum VCAM concentrations are reported to be elevated in individuals following ischemic stroke, but not TIAs, and no correlation between serum concentrations and the severity of injury or neurological outcome has been established (Bitsch, A. et al., *Stroke* 29:2129-2135, 1998). VCAM concentration is also elevated in the cerebrospinal fluid of patients with subarachnoid hemorrhage (Polin, R. S. et al., *J. Neurosurg.* 89:559-567, 1998). Elevations in the serum VCAM concentration likely indicate activation of the immune system and the presence of an inflammatory response. Serum VCAM concentrations are elevated in individuals with atherosclerosis, various forms of cancer, diabetes, preeclampsia, vascular injury, and other nonspecific inflammatory states (Otsuki, M. et al., *Diabetes* 46:2096-2101, 1997; Banks, R. E. et al., *Br. J. Cancer* 68:122-124, 1993; Steiner, M. et al., *Thromb. Haemost.* 72:979-984, 1994; Austgulen, R. et al., *Eur. J. Obstet. Gynecol. Reprod. Biol.* 71:53-58, 1997). The serum concentration of VCAM is elevated following ischemic stroke. Serum concentrations are elevated 5 days after onset and return to normal values 14 days after onset. Serum VCAM concentrations can approach 900 ng/ml (9 nM) in stroke patients. Further studies are needed to investigate changes in serum VCAM concentration in the context of stroke. Serum VCAM concentrations are likely related to the extent of endothelial cell damage. Serum VCAM may be a sensitive marker of endothelial cell injury. However, VCAM serum elevations are not specific to stroke or cerebral injury. In addition, current information indicates that VCAM serum concentrations are not significantly elevated until 5 days after stroke. This time point is well beyond the therapeutic window, indicating that VCAM would not be a suitable marker for stroke.

Monocyte chemotactic protein-1 (MCP-1), also called monocyte chemoattractant protein-1, is a 10 kDa chemotactic factor that attracts monocytes and basophils, but not neutrophils or eosiniphils. MCP-1 is normally found in equilibrium between a monomeric and homodimeric form, and it is normally produced in and secreted by monocytes and vascular endothelial cells (Yoshimura, T. et al., *FEBS Lett.* 244:487-493, 1989; Li, Y. S. et al., *Mol. Cell. Biochem.* 126:61-68, 1993). MCP-1 has been implicated in the pathogenesis of a variety of diseases that involve monocyte infiltration, including psoriasis, rheumatoid arthritis, and atherosclerosis. The normal concentration of MCP-1 in plasma is <0.1 ng/ml. Investigations using animal models have demonstrated that both MCP-1 mRNA and protein are expressed in increased amounts in ischemic brain tissue (Wang, X. et al., *Stroke* 26:661-665, 1995; Yamagami, S. et al., *J. Leukoc. Biol.* 65:744-749, 1999). Elevations of the serum concentration of MCP-1 are associated with various conditions associated with inflammation, including alcoholic liver disease, interstitial lung disease, sepsis, systemic lupus erythematosus, and acute coronary syndromes (Fisher, N. C. et al., *Gut* 45:416-420, 1999; Suga, M. et al., *Eur. Respir. J.* 14:376-382, 1999; Bossnik, A. W. et al., *Blood* 86:3841-3847, 1995; Kaneko, H. et al., *J. Rheumatol.* 26:568-573, 1999; Nishiyama, K. et al., *Jpn. Circ. J.* 62:710-712, 1998; Matsumori, A. et al., *J. Mol. Cell. Cardiol.* 29:419-423, 1997). MCP-1 is released into the bloodstream upon activation of monocytes and endothelial cells. The kinetics of MCP-1 release into and clearance from the bloodstream in the context of stroke are currently unknown.

Any protein whose expression is altered specifically as a result of the insult, directly by acute phase proteins, or concurrent with acute phase proteins can be considered acute phase reactants. In the context of stroke, proteins whose serum concentrations are elevated as a direct result of cell death are not considered to be acute phase reactants, but proteins whose gene expression and resulting secretion and serum concentration is altered in response to cerebral injury or ischemia are considered acute phase reactants. Examples of such proteins include matrix metalloproteinase-3 and matrix metalloproteinase-9.

Matrix metalloproteinase-3 (MMP-3), also called stromelysin-1, is a 45 kDa zinc- and calcium-binding proteinase that is synthesized as an inactive 60 kDa precursor. Mature MMP-3 cleaves proteoglycan, fibrinectin, laminin, and type IV collagen, but not type I collagen. MMP-3 is synthesized by a variety of cells, including smooth muscle cells, mast cells, macrophage-derived foam cells, T lymphocytes, and endothelial cells (Johnson, J. L., et al., *Arterioscler. Thromb. Vasc. Biol.* 18:1707-1715, 1998). MMP-3, like other MMPs, is involved in extracellular matrix remodeling, which can occur following injury or during intervascular cell migration. MMP-3 is normally found at a concentration of <125 ng/ml in plasma (Zucker, S. et al., *J. Rheumatol.* 26:78-80, 1999). The serum MMP-3 concentration also has been shown to increase with age, and the concentration in males is approximately 2 times higher in males than in females (Manicourt, D. H. et al., *Arthritis Rheum.* 37:1774-1783, 1994). MMP-3 is found in the shoulder region of atherosclerotic plaques, which is the region most prone to rupture, and may be involved in atherosclerotic plaque destabilization (Johnson, J. L. et al., *Arterioscler. Thromb. Vasc. Biol.* 18:1707-1715, 1998). Therefore, the circulating MMP-3 concentration may be elevated as a result of atherosclerotic plaque rupture. Serum MMP-3 also may be elevated inflammatory conditions that induce mast cell degranulation. Serum MMP-3 concentrations are elevated in patients with arthritis and systemic lupus erythematosus (Zucker, S. et al., *J. Rheumatol.* 26:78-80, 1999; Keyszer, G. et al., *J. Rheumatol.* 57:392-398, 1998; Keyszer, G. et al., *J. Rheumatol.* 26:251-258, 1999). Serum MMP-3 also is elevated in patients with prostate and urothelial cancer, and also glomerulonephritis (Lein, M. et al., *Urologe A* 37:377-381, 1998; Gohji, K. et al., *Cancer* 78:2379-2387, 1996; Akiyama, K. et al., *Res. Commun. Mol. Pathol. Pharmacol.* 95:115-128, 1997). The serum concentration of MMP-3 may also be elevated in patients with other types of cancer. Serum MMP-3 is decreased in patients with hemochromatosis (George, D. K. et al., *Gut* 42:715-720, 1998). MMP-3 is released during mast cell degranulation, and is presumably released during atherosclerotic plaque rupture. In this regard, MMP-3 may be useful as a marker of stroke associated with plaque rupture.

Matrix metalloproteinase 9 (MMP-9) is a secreted 92 kDa serine proteinase produced by neutrophils and various tissues, whose substrates include components of the extracellular matrix. MMPs are synthesized as inactive zymogens that are proteolytically cleaved to produce active MMPs. They have the ability to bind divalent cations, most commonly $Zn^{2+}$, and this binding is essential for proteinase activity. Cancer cells sometimes produce MMPs to facilitate extracellular matrix degradation during invasion and metastasis. MMP is normally found in brain, and its expression is induced by various cytokines (Mun-Bryce, S. and Rosenberg, G A., *J. Cereb. Blood Flow Metab.* 18:1163-1172, 1998). The normal serum concentration of MMP-9 is <35 ng/ml (380 pM). Serum MMP-9 concentration is marginally elevated following cerebral ischemia in a rat model, but no human studies have been reported (Romanic, A. M. et al., *Stroke* 29:1020-1030, 1998). MMP-9 gene expression is maximally elevated 16-24 hours following cerebral hemorrhage or intracerebral injection of proinflammatory cytokines in rats (Rosenberg, G. A., *J. Neurotrauma* 12:833-842, 1995). Furthermore, MMP-9 may be partially responsible for the development of delayed neurological deficits, particularly following hemorrhagic transformation of ischemic stroke and vasospasm following hemorrhagic stroke. In this regard, elevation of the serum MMP-9 concentration may indicate the potential for occurrence of delayed neurological deficit. Elevations in the serum concentration of MMP-9 may be associated with various carcinomas and giant cell arteritis (Blankaert, D. et al., *J. Acquir. Immune Defic. Syndr. Hum. Retrovirol.* 18:203-209, 1998; Endo, K. et al., *Anticancer Res.* 17:2253-2258, 1997; Hayasaka, A. et al., *Hepatology* 24:1058-1062, 1996; Moore, D. H. et al., *Gynecol. Oncol.* 65:78-82, 1997; Sorbi, D. et al., *Arthritis Rheum.* 39:1747-1753, 1996). MMP-9 is produced and released into the circulation following various stroke types, but these studies have not been performed using human samples. Serum concentrations of MMP-9 have been demonstrated to exceed 600 ng/ml (6.5 nM) in humans. MMP-9 is a specific marker of extracellular matrix degradation, but it is not specific for stroke or cerebral injury and can be elevated in other disease states such as cancer. However, the measurement of increased serum MMP-9 concentration may indicate that the individual is at high risk for the development of hemorrhagic transformation following ischemic stroke or vasospasm following hemorrhagic stroke. This determination is based on the hypothesis that MMP-9 is a pathogenic mediator of these delayed neurological deficits.

Other non-specific markers of cerebral injury include caspase-3, B-type natriuretic peptide, cardiac troponin I, head activator and the hemoglobin $\alpha_2$ chain. In addition, the present invention provides methods for identifying novel markers for the diagnosis of stroke and TIAs.

Caspase-3, also called CPP-32, YAMA, and apopain, is an interleukin-1β converting enzyme (ICE)-like intracellular cysteine proteinase that is activated during cellular apoptosis. Caspase-3 is present as an inactive 32 kDa precursor that is proteolytically activated during apoptosis induction into a heterodimer of 20 kDa and 11 kDa subunits (Fernandes-Alnemri, T. et al., *J. Biol. Chem.* 269:30761-30764, 1994). Its cellular substrates include poly(ADP-ribose) polymerase (PARP) and sterol regulatory element binding proteins (SREBPs) (Liu, X. et al., *J. Biol. Chem.* 271:13371-13376, 1996). The normal plasma concentration of caspase-3 is unknown. Studies in animal models have demonstrated that caspase-3 expression is elevated following cerebral ischemia (Phanithi, P. B. et al., *Neuropathol.* 20:273-282, 2000; Kim, G. W. et al., *J. Cereb. Blood Flow Metab.* 20:1690-1701, 2000). In addition, brain ischemia cause activation of caspase-3 in patients with permanent and transient brain ischemia (Love, S. et al., *Neuroreport* 11:2495-2499, 2000). Furthermore, there are increasing amounts of evidence supporting the hypothesis of apoptosis induction in cardiac myocytes associated with ischemia and hypoxia (Saraste, A., *Herz.* 24:189-195, 1999; Ohtsuka, T. et al., *Coron. Artery Dis.* 10:221-225, 1999; James, T. N., *Coron. Artery Dis.* 9:291-307, 1998; Bialik, S. et al., *J. Clin. Invest.* 100:1363-1372, 1997; Long, X. et al., *J. Clin. Invest.* 99:2635-2643, 1997). Elevations in the plasma caspase-3 concentration may be associated with any physiological event that involves apoptosis. The kinetics of caspase-3 release into and removal from the bloodstream are currently unknown. Interestingly, ischemia-induced apoptosis may have characteristics that distinguish it from other forms of apoptosis, but the induction of caspase-3 is common to all apoptotic pathways.

Troponin I (TnI) is a 25 kDa inhibitory element of the troponin TIC complex, found in all striated muscle tissue. TnI binds to actin in the absence of Ca2+, inhibiting the ATPase activity of actomyosin. A TnI isoform that is found in cardiac tissue (cTnI) is 40% divergent from skeletal muscle TnI, allowing both isoforms to be immunologically distinguished. The normal plasma concentration of cTnI is <0.1 ng/ml (4 pM). The plasma cTnI concentration is elevated in patients with acute coronary syndromes, including AMI. Because of its cardiac specificity, cTnI may be useful in ruling out cardiac causes of elevations of various markers also associated with stroke. In this regard, the measurement of the cardiac troponin TIC complex, as well as its ratio with total cTnI, may be of importance in identifying a cardiac cause of elevations of markers used to diagnose stroke.

Head activator (HA) is an 11 amino acid, 1.1 kDa neuropeptide that is found in the hypothalamus and intestine. It was originally found in the freshwater coelenterate hydra, where it acts as a head-specific growth and differentiation factor. In humans, it is thought to be a growth regulating agent during brain development. The normal serum HA concentration is <0.1 ng/ml (100 pM) Serum HA concentration is persistently elevated in individuals with tumors of neural or neuroendocrine origin (Schaller, H. C. et al., *J Neurooncol.* 6:251-258, 1988; Winnikes, M. et al., *Eur. J. Cancer* 28:421-424, 1992). No studies have been reported regarding HA serum elevations associated with stroke. HA is presumed to be continually secreted by tumors of neural or neuroendocrine origin, and serum concentration returns to normal following tumor removal. Serum HA concentration can exceed 6.8 ng/ml (6.8 nM) in individuals with neuroendocrine-derived tumors. The usefulness of HA as part of a stroke panel would be to identify individuals with tumors of neural or neuroendocrine origin. These individuals may have serum elevations of markers associated with cerebral injury as a result of cancer, not cerebral injury related to stroke. Although these individuals may be a small subset of the group of individuals that would benefit from a rapid diagnostic of cerebral injury, the use of HA as a marker would aid in their identification. Finally, angiotensin converting enzyme, a serum enzyme, has the ability to degrade HA, and blood samples would have to be drawn using EDTA as an anticoagulant to inhibit this activity.

Hemoglobin (Hb) is an oxygen-carrying iron-containing globular protein found in erythrocytes. It is a heterodimer of two globin subunits. $\alpha_2\gamma_2$ is referred to as fetal Hb, $\alpha_2\beta_2$ is called adult HbA, and $\alpha_2\delta_2$ is called adult $HbA_2$. 90-95% of hemoglobin is HbA, and the $\alpha_2$ globin chain is found in all Hb types, even sickle cell hemoglobin. Hb is responsible for carrying oxygen to cells throughout the body. $Hb\alpha_2$ is not normally detected in serum. The usefulness of $Hb\alpha_2$ on a stroke panel would be to determine the extent of hemolysis and the resulting contribution of erythrocyte-originated(?) proteins to the measured serum concentration. An accepted level of hemolysis would have to be established for the measurement of serum markers that are present in erythrocytes. In certain cases, stroke or other cerebral injuries may cause local changes in blood pressure, and markers associated with these changes in blood pressure may provide important diagnostic and/or prognostic information into the pathologic condition of a subject. For example, in ischemic stroke, the blockage can cause an increase in blood pressure in the involved arteries, while in hemorrhagic stroke, bleeding can result in a decrease in the blood pressure in the involved arteries. Moreover, during vasospasm, such as often occurs after hemorrhagic stroke, an increase in blood pressure may be observed in the involved spastic artery.

Peptides that may affect blood pressure, either locally or systemically, can act by a variety of mechanisms, such as by changing the diameter of the arteries (vasoconstriction or vasodilation) or by increasing or decreasing the amount of renal output which will increase or decrease total blood volume. Of particular interest are the regulators that cause vasoconstriction or vasodilation at or near the site of injury without more widespread systemic affects. Regulators of blood pressure may become elevated or suppressed depending upon the type of stroke and whether the regulator causes an increase or a decrease in blood pressure. As a result, changes in the levels of various blood pressure-related marker(s) may permit the differentiation between ischemic and hemorrhagic stroke.

For example, the level of one or more vasodilators may increase, and/or the level of one or more vasoconstrictors may decrease or remain unchanged during ischemic stroke; conversely, the opposite may occur during hemorrhagic stroke. Additionally, once a subject has been diagnosed with a hemorrhagic stroke, the subject could be monitored for a predilection to, or an onset of, vasospasm by looking for changes in various pressure regulators. Finally, one or more agents that might offset these local blood pressure changes can provide important defenses against the affects of an unabated rise or fall of local blood pressure.

Blood pressure regulators that may be useful markers of stroke include those that have paracrine actions, i.e., they are secreted and act at or near the site of injury. The natriuretic peptides ANP, BNP, and CNP are known to have vasodilatory actions. CNP is particularly interesting because it is widely believed to have paracrine effects, it is found in the vascular endothelium of the brain, its receptors are also found in the vascular endothelium of the brain, and it has been shown to cause dose-dependent vasodilation of isolated rat cerebral arteries (Mori, Y., et al., *Eur J Pharmacol* 320:183, 1997).

A-type natriuretic peptide (ANP) (also referred to as atrial natriuretic peptide) is a 28 amino acid peptide that is synthesized, stored, and released atrial myocytes in response to atrial distension, angiotensin II stimulation, endothelin, and sympathetic stimulation (beta-adrenoceptor mediated). ANP is synthesized as a precursor molecule (pro-ANP) that is converted to an active form by proteolytic cleavage. In addition to atrial natriuretic peptide (ANP99-126) itself, linear peptide fragments from its N-terminal prohormone segment have also been reported to have biological activity.

Elevated levels of ANP are found during hypervolemia and congestive heart failure. ANP is involved in the long-term regulation of sodium and water balance, blood volume and arterial pressure. This hormone decreases aldosterone release by the adrenal cortex, increases glomerular filtration rate (GFR), produces natriuresis and diuresis (potassium sparing), and decreases renin release thereby decreasing angiotensin II. These actions contribute to reductions in blood volume and therefore central venous pressure (CVP), cardiac output, and arterial blood pressure. Several isoforms of ANP have been identified, and their relationship to stroke incidence studied. See, e.g., Rubatu et al., *Circulation* 100:1722-6, 1999; Estrada et al., *Am. J. Hypertens.* 7:1085-9, 1994.

Chronic elevations of ANP appear to decrease arterial blood pressure primarily by decreasing systemic vascular resistance. The mechanism of systemic vasodilation may involve ANP receptor-mediated elevations in vascular smooth muscle cGMP as well as by attenuating sympathetic vascular tone. This latter mechanism may involve ANP acting upon sites within the central nervous system as well as through inhibition of norepinephrine release by sympathetic nerve terminals. ANP may be viewed as a counter-regulatory system for the renin-angiotensin system. A new class of drugs that are neutral endopeptidase (NEP) inhibitors have demonstrated efficacy in heart failure. These drugs inhibit neutral endopeptidase, the enzyme responsible for the degradation of ANP, and thereby elevate plasma levels of ANP. NEP inhibition is particularly effective in heart failure when the drug has a combination of both NEP and ACE inhibitor properties.

B-type natriuretic peptide (BNP), also called brain-type natriuretic peptide is a 32 amino acid, 4 kDa peptide that is involved in the natriuresis system to regulate blood pressure and fluid balance (Bonow, R. O., *Circulation* 93:1946-1950, 1996). The precursor to BNP is synthesized as a 108-amino acid molecule, referred to as "pre pro BNP," that is proteolytically processed into a 76-amino acid N-terminal peptide (amino acids 1-76), referred to as "NT pro BNP" and the 32-amino acid mature hormone, referred to as BNP or BNP 32 (amino acids 77-108). It has been suggested that each of these species—NT pro-BNP, BNP-32, and the pre pro BNP—can circulate in human plasma (Tateyama et al., *Biochem. Biophys. Res. Commun.* 185:760-7, 1992; Hunt et al., *Biochem. Biophys. Res. Commun.* 214:1175-83, 1995). The 2 forms, pre pro BNP and NT pro BNP, and peptides which are derived from BNP, pre pro BNP and NT pro BNP and which are present in the blood as a result of proteolyses of BNP, NT pro BNP and pre pro BNP, are collectively described as markers related to or associated with BNP. Proteolytic degradation of BNP and of peptides related to BNP have also been described in the literature and these proteolytic fragments are also encompassed it the term "BNP related peptides". BNP and BNP-related peptides are predominantly found in the secretory granules of the cardiac ventricles, and are released from the heart in response to both ventricular volume expansion and pressure overload (Wilkins, M. et al., *Lancet* 349: 1307-1310, 1997).

BNP has been demonstrated to be elevated in the plasma of patients with subarachnoid hemorrhage (Sviri, G. E., et al., *Stroke* 31:118-122, 2000; Tomida, M. et al., *Stroke* 29:1584-1587, 1998; Berendes, E. et al., Lancet 349:245-249, 1997; Wijdicks, E. F., et al., *J. Neurosurg.* 87:275-280, 1997). Furthermore, there are numerous reports of elevated BNP concentration associated with congestive heart failure and renal failure. While BNP and BNP-related peptides are likely not specific for stroke, they may be sensitive markers of stroke because they may indicate a perturbation of the natriuretic system associated with stroke. The term "BNP" as used herein refers to the mature 32-amino acid BNP molecule itself. As the skilled artisan will recognize, however, other markers related to BNP may also serve as diagnostic or prognostic indicators in patients with stroke. For example, BNP is synthesized as a 108-amino acid pre pro-BNP molecule that is proteolytically processed into a 76-amino acid "NT pro BNP" and the 32-amino acid BNP molecule. Because of its relationship to BNP, the concentration of NT pro-BNP molecule can also provide diagnostic or prognostic information in patients.

The phrase "marker related to BNP or BNP related peptide" refers to any polypeptide that originates from the pre pro-BNP molecule, other than the 32-amino acid BNP molecule itself. Thus, a marker related to or associated with BNP includes the NT pro-BNP molecule, the pro domain, a fragment of BNP that is smaller than the entire 32-amino acid sequence, a fragment of pre pro-BNP other than BNP, and a fragment of the pro domain. One skilled in the art will also recognize that the circulation contains proteases which can proteolyze BNP and BNP related molecules and that these proteolyzed molecules (peptides) are also considered to be "BNP related" and are additionally subjects of this invention.

C-type natriuretic peptide (CNP) a 22-amino acid peptide that is the primary active natriuretic peptide in the human brain; CNP is also considered to be an endothelium-derived relaxant factor, which acts in the same way as nitric oxide (NO) (Davidson et al., *Circulation* 93:1155-9, 1996). CNP is structurally related to A-type natriuretic peptide (ANP) and B-type natriuretic peptide (BNP); however, while ANP and BNP are synthesized predominantly in the myocardium, CNP is synthesized in the vascular endothelium as a precursor (pro-CNP) (Prickett et al., *Biochem. Biophys. Res. Commun.* 286:513-7, 2001). CNP is thought to possess vasodilator effects on both arteries and veins and has been reported to act mainly on the vein by increasing the intracellular cGMP concentration in vascular smooth muscle cells.

Other peptides of endothelial origin that have actions in the brain include adrenomedullin (ADM), another potent vasodilator (Jougasaki, M. and Burnett, J. C. Jr., *Life Sci* 66:855, 2000), and the endothelins (Guimaraes et al., *Hypertension* 19, 2 Suppl.: 1179-86, 1992; Ortega Mateo, A. and de Artinano, A. A., *Pharmacol Res* 36:339, 1997). The endothelins are three related peptides (endothelin-1, endothelin-2, and endothelin-3) encoded by separate genes that are produced by vascular endothelium, each of which exhibit potent vasoconstricting activity.

Adrenomedullin (AM) is a 52-amino acid peptide which is produced in many tissues, including adrenal medulla, lung, kidney and heart (Yoshitomi et al., *Clin. Sci.* (*Colch*) 94:135-9, 1998). Intravenous administration of AM causes a longlasting hypotensive effect, accompanied with an increase in the cardiac output in experimental animals. AM has been reported to enhance the stretch-induced release of ANP from the right atrium, but not to affect ventricular BNP expression. AM is synthesized as a precursor molecule (pro-AM). The N-terminal peptide processed from the AM precursor has also been reported to act as a hypotensive peptide (Kuwasako et al., Ann. Clin. Biochem. 36:622-8, 1999).

Endothelin-1 (ET-1) is a 21 amino acid residue peptide, synthesized as a 212 residue precursor (preproET-1), which contains a 17 residue signal sequence that is removed to provide a peptide known as big ET-1. This molecule is further processed by hydrolysis between trp21 and val22 by endothelin converting enzyme. Both big ET-1 and ET-1 exhibit biological activity; however the mature ET-1 form exhibits greater vasoconstricting activity (Brooks and Ergul, J. Mol. Endocrinol. 21:307-15, 1998). Similarly, endothelin-2 and endothelin-3 are also 21 amino acid residues in length, and are produced by hydrolysis of big endothelin-2 and big endothelin-3, respectively (Yap et al., Br. J. Pharmacol. 129:170-6, 2000; Lee et al., Blood 94:1440-50, 1999).

Assay Measurement Strategies

Numerous methods and devices are well known to the skilled artisan for the detection and analysis of the markers of the instant invention. With regard to polypeptides or proteins in patient test samples, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the markers is also contemplated by the present invention. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room setting.

The analysis of a plurality of markers may be carried out separately or simultaneously with one test sample. Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvageable tissue, the appropriateness of neuroprotectant or thrombolytic drug therapies, the effectiveness of various stroke therapies as indicated by reperfusion or resolution of symptoms, differentiation of ischemic from hemorrhagic stroke, identification of transient ischemic attacks, identification of the severity of the event, identification of the disease severity, and identification of the patient's outcome, including risk of future events.

A panel consisting of the markers referenced above may be constructed to provide relevant information related to the diagnosis of stroke and management of patients with stroke. Such a panel may be constructed using 1, 2, 3, 4, 5, 6, 7, 8, 9, 10, 11, 12, 13, 14, 15, 16, 17, 18, 19 or 20 individual markers. The analysis of a single marker or subsets of markers comprising a larger panel of markers could be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay corrects predicts (Tietz Textbook of Clinical Chemistry, $2^{nd}$ edition, Carl Burtis and Edward Ashwood eds., W. B. Saunders and Company, p. 496).

In a preferred embodiment, one or more specific marker of cerebral injury is combined with one or more non-specific marker of cerebral injury to create a diagnostic panel for stroke or TIAs. In addition, the present invention provides methods for determining the components of such a plurality of markers. Once such a panel is assembled, the presence or level of each of the various markers is determined in one or more patient samples, and optionally compared to the diagnostic levels or normal levels of each marker.

Individual results obtained from several markers may be combined in various combinations for further information on diagnosis and/or prognosis of an individual. For example, using ROC curves, threshold values for each of a set of markers may be determined, and values from a sample compared to these threshold values.

In a preferred alternative, combined result of a variety of panels could be interpreted as a probability, expressed either as a numerical score or a percentage that an individual has stroke, and, furthermore, a probability that it is an ischemic stroke based on a particular selection of panel(s), and a probability that it is a hemorrhagic stroke based on a particular selection of panel(s). ROC curves are prepared by plotting ROC curves for the sensitivity of a particular panel of markers versus 1-(specificity) for the panel at various cutoffs. The results provide an empirical description of the decision threshold effect. "ROC area" refers to the area under the ROC curve. The area under the ROC curve is a measure of the probability that the perceived measurement will allow correct identification of a condition. The greater the area under the curve (AUC), the greater the discriminatory ability. A test with no discriminatory ability has an AUC of 0.5. A test with perfect discriminatory ability has an AUC of 1.0. In such a way, combined information can be used to improve the value of individual marker assays.

To achieve rapid manipulation of data obtained from a multitude of markers, it may be appropriate to employ a computer algorithm for calculating the ROC curves described above, and for analysis of patient probability scores. Such a program may be used to factor or weigh several subsets of the marker assays performed simultaneously based on preset panels and combinations of markers.

In another embodiment, the present invention provides a kit for the analysis of markers. Such a kit preferably comprises devises and reagents for the analysis of at least one test sample and instructions for performing the assay. Optionally the kits may contain one or more means for converting a marker level to a diagnosis of the patient, such as a nomogram, standard table, or computer program for calculating probabilities.

EXAMPLES

The following examples serve to illustrate the present invention. These examples are in no way intended to limit the scope of the invention.

Example 1

Blood Sampling

Blood specimens were collected by trained study personnel using EDTA as the anticoagulant and centrifuged for greater than or equal to 10 minutes. The plasma component was transferred into a sterile cryovial and frozen at −20° C. or colder. Specimens from the following population of patients and normal healthy donors were collected (Table 1). Clinical histories were available for each of the patients to aid in the statistical analysis of the assay data.

TABLE 1

| | Blood Specimens Collected | | | | | | | |
|---|---|---|---|---|---|---|---|---|
| | Ischemic | | Hemorrhagic | | | Closed Head Injury | Post-CPR | Un-known | Normal Healthy Donors |
| | All | TIA | All | Sub-arachnoid | Intra-cerebral | | | | |
| # Patients | 82 | 25 | 62 | 38 | 24 | 19 | 3 | 7 | 157 |
| # Samples | 222 | 47 | 343 | 283 | 60 | 44 | 4 | 12 | 157 |
| Time from Onset | | | | | | | | | |
| ≦6 h | 28 | 9 | 10 | 5 | 5 | 0 | 0 | 3 | |
| 6-12 h | 24 | 7 | 2 | 1 | 1 | 2 | 0 | 0 | |
| 12-24 h | 34 | 10 | 14 | 7 | 8 | 9 | 1 | 2 | |
| 24-48 h | 47 | 12 | 30 | 16 | 12 | 10 | 1 | 0 | |
| 48-72 h | 31 | 6 | 28 | 17 | 11 | 12 | 1 | 1 | |
| 72-96 h | 22 | 3 | 25 | 19 | 8 | 4 | 1 | 1 | |
| 96-120 h | 2 | 0 | 18 | 15 | 3 | 0 | 0 | 0 | |
| 120-144 h | 2 | 0 | 20 | 18 | 1 | 1 | 0 | 1 | |
| >144 h | 32 | 0 | 203 | 185 | 11 | 6 | 0 | 4 | |
| Vasospasm | | | 19 | 19 | 0 | | | | |
| Transformed | 5 | 0 | | | | | | | |

Example 2

Biochemical Analyses

Markers were measured using standard immunoassay techniques. These techniques involved the use of antibodies to specifically bind the protein targets. A monoclonal antibody directed against a selected marker was biotinylated using N-hydroxysuccinimide biotin (NHS-biotin) at a ratio of about 5 NHS-biotin moieties per antibody. The antibody-biotin conjugate was then added to wells of a standard avidin 384 well microtiter plate, and antibody conjugate not bound to the plate was removed. This formed the "anti-marker" in the microtiter plate. Another monoclonal antibody directed against the same marker was conjugated to alkaline phosphatase using succinimidyl 4-[N-maleimidomethyl]-cyclohexane-1-carboxylate (SMCC) and N-succinimidyl 3-[2-pyridyldithio]propionate (SPDP) (Pierce, Rockford, Ill.).

Assays for BNP were performed using murine anti-BNP monoclonal antibody 106.3 obtained from Scios Incorporated (Sunnyvale, Calif.). The hybridoma cell line secreting mAb 106.3 was generated from a fusion between FOX-NY cells and spleen cells from a Balb/c mouse immunized with human BNP 1-32 conjugated to BSA. A second murine anti-BNP antibody was produced by Biosite Incorporated (San Diego, Calif.) by antibody phage display as described previously (U.S. Pat. No. 6,057,098), using human BNP antigen (Scios Incorporated, Sunnyvale, Calif.; U.S. Pat. No. 5,114,923) conjugated to KLH by standard techniques. Human BNP antigen was also used for assay standardization.

Assays for IL-6 were performed using commercially available murine anti-human IL-6 monoclonal antibody (clone #6708.111) and a goat anti-human IL-6 polyclonal antibody (R&D Systems, Minneapolis, Minn.). Human IL-6 used for assay standardization was expressed and purified by Biosite Incorporated. IL-6 cDNA was prepared from a human spleen cDNA library by PCR and subcloned into the bacterial expression vector pBRnco H3. The expression and purification of recombinant IL-6 was performed using methods previously described in U.S. Pat. No, 6,057,098.

Assays for MMP-9 were performed using murine anti-MMP-9 antibodies generated by Biosite Incorporated using phage display and recombinant protein expression as described previously (U.S. Pat. No. 6,057,098). Commercially available MMP-9 antigen was used for assay standardization (Calbiochem-Novabiochem Corporation, San Diego, Calif.). The immunogen used for antibody production was prepared by Biosite Incorporated. PCR primers were made corresponding to sequence at the 5'-end of human MMP-9 and the coding sequence at the 3'-end of human MMP-9 (Genbank accession number J05070), including six histidine codons inserted between the end of the coding sequence and the stop codon to assist in purification of the recombinant protein by metal-chelate affinity chromatography, primers A (5'(AGGTGTCGTAAGCTTGAATTCAGACAC-CTCTGCCGCCACCATGAG) SEQ ID NO:1) and B (5' (GGGCTGGCTTACCTGCGGCCTTAGT-GATGGTGATGGTGATGGTCCTCAGGGCACT GCAGGATG) SEQ ID NO:2), respectively. The 5' primer also contains 21 base pairs of pEAK12 vector sequence (Edge BioSystems, Gaithersburg, Md.) at its 5'-end corresponding to the EcoRI site and sequence immediately upstream. The 3' primer contains an additional 20 base-pairs of vector sequence, including 6 bases of the NotI site and the sequence immediately downstream, at its 5' end. The vector sequence at the 5'-ends of these primers will form, upon treatment with T4 DNA polymerase, single-stranded overhangs that are specific and complementary to those on the pEAK12 vector. The PCR amplification of the MMP-9 gene insert was done on a 2×100 µl reaction scale containing 100 pmol of 5' primer (A), 100 pmol of 3' primer (B), 2.5 units of Expand polymerase, 10 µl 2 mM dNTPs, 10 µl 10× Expand reaction buffer, 1 µl of Clontech Quick-clone human spleen cDNA (Clontech Laboratories, Palo Alto, Calif.) as template, and water to 100 µl. The reaction was carried out in a Perkin-Elmer thermal cycler as described in Example 18 (U.S. Pat. No. 6,057,098). The PCR products were precipitated and fractionated by agarose gel electrophoresis and full-length products excised from the gel, purified, and resuspended in water (Example 17, U.S. Pat. No. 6,057,098). The pEAK12 vector was prepared to receive insert by digestion with NotI and EcoRI (New England BioLabs, Beverly, Mass.). The insert and EcoRl/NotI digested pEAK12 vector were prepared for T4 exonuclease digestion by adding 1.0 µl of 10× Buffer A to 1.0 µg of DNA and bringing the final volume to 9 µl with water. The samples were digested for 4 minutes at 30° C. with 1 µl (1U/µl) of T4 DNA polymerase. The T4 DNA polymerase was heat inactivated by incubation at 70° C. for 10 minutes. The samples were cooled, briefly centrifuged, and 45 ng of the digested insert added to 100 ng of digested pEAK12 vector in a fresh microfuge tube. After the addition of 1.0 µl of 10× annealing buffer, the volume was brought to 10 µl with water. The mixture was heated to 70° C. for 2 minutes and cooled over 20 minutes to room temperature, allowing the insert and vector to anneal. The annealed DNA was diluted one to four with distilled water and electroporated (Example 8, U.S. Pat. No. 6,057,098) into 30 µl of electrocompetent $E.$ $coli$ strain, DH10B (Invitrogen, Carlsbad, Calif.). The transformed cells were diluted to 1.0 ml with 2×YT broth and 10 µl, 100 µl, 300 µl plated on LB agar plates supplemented with ampicillin (75 µg/ml) and grown overnight at 37° C. Colonies were picked and grown overnight in 2×YT (75 µg/ml ampicillin at 37° C. The following day glycerol freezer stocks were made for long term storage at −80° C. The sequence of these clones (MMP9peak12) was verified at MacConnell Research (San Diego, Calif.) by the dideoxy chain termination method using a Sequatherm sequencing kit (Epicenter Technologies, Madison, Wis.), oligonucleotide primers C 5'(TTCTCAAGCCT-CAGACAGTG) SEQ ID NO:3) and D (5'(CCTGGATG-CAGGCTACTCTAG) SEQ ID NO:4) that bind on the 5' and 3' side of the insert in the pEAK12 vector, respectively, and a LI-COR 4000L automated sequencer (LI-COR, Lincoln, Nebr.). Plasmid suitable for transfection and the subsequent expression and purification of human MMP-9 was prepared from clone MMP9peak12.2 using an EndoFree Plasmid Mega Kit as per manufacturer's recommendations (Qiagen, Valencia, Calif.). HEK 293 ("Peak") cells were expanded into a T-75 flask from a 1 ml frozen vial stock (5×10$^6$ cells/ml) in IS 293 medium (Irvine Scientific, Santa Ana, Calif.) with 5% fetal bovine serum (FBS) (JRH Biosciences, Lenexa, Kans.), 20 units/ml Heparin, 0.1% Pluronic F-68 (JRH Biosciences, Lenexa, Kans.), and 50 µg/ml Gentamicin (Sigmna, St. Louis, Mo.). After incubating at 37° C., 85% humidity, and 5% $CO_2$ for 2-3 days, the cells were expanded into a T-175 flask while reducing the FBS to 2% in the medium. The cells were then continuously expanded 1:2 over a period of 2-3 weeks, establishing a consistent mono-layer of attached cells. Peak cells grown with the above method were centrifuged at 1000 rpm for 6 minutes, and the supernatant was discarded. After counting the cells to establish the density and checking for at least 90% viability with a standard dye test, the cells were resuspended at 5×10$^5$ cells/ml in 400 ml IS 293 with 2% FBS and 50 µg/ml Gentamicin and added to a 1 L spinner flask. Then, to a conical tube 5 ml IS 293 and 320 µg MMP-9 DNA were added per 400 ml spinner flask. This was mixed and incubated at room temperature for 2 minutes. 400 µl X-tremeGENE RO-1539 transfection reagent (Roche Diagnostics, Indianapolis, Ind.) per spinner was added to the tube that was then mixed and incubated at room temperature for 20 minutes. The mixture was added to the spinner flask, and incubated at 37° C., 85% humidity, and 5% $CO_2$ for 4 days at 100 rpm. The cell broth from the above spinner flask was spun down at 3500 rpm for 20 minutes, and the supernatant was saved for purification of the MMP-9. A column containing 20 ml Chelating Fast Flow resin (Amersham Pharmacia Biotech, Piscataway, N.J.) charged with $NiCl_2$ was equilibrated with BBS. Then the supernatant from the spinner flask was loaded on the column, washed with BBS+10 mM imidazole, and eluted with 200 mM imidazole. The elution was used for the load of the next purification step after adding $CaCl_2$ to 10 mM. A column with 5 ml gelatin sepharose 4B resin (Amersham Pharmacia Biotech, Piscataway, N.J.) was equilibrated with BBS+10 mM $CaCl_2$. After loading the antigen, the column was washed with equilibration buffer, and the MMP-9 was eluted using equilibration buffer+2% dimethyl sulfoxide (DMSO). Polyoxyethyleneglycol dodecyl ether (BRIJ-35)

(0.005%) and EDTA (10 mM) were added to the elution, which was then dialyzed into the final buffer (50 mM Tris, 400 mM NaCl, 10 mM $CaCl_2$, 0.01% $NaN_3$, pH 7.5, 0.005% BRIJ-35, 10 mM EDTA). Finally, the protein was concentrated to approximately 0.25 mg/ml for storage at 4° C. Zymogram gels were used to check for production and purification of MMP-9. Western blots were also used to check for activity of the protein. MMP-9 (Oncogene Research Products, Cambridge, Mass.) was used for comparison of the purified antigen made using the PEAK cell system to known standards.

Assays for TAT complex were performed using a commercially available murine anti-human TAT complex-specific monoclonal antibody, clone EST1, (American Diagnostica Inc., Greenwich, Conn.) and murine anti-human TAT complex antibodies produced by Biosite Incorporated using phage display and recombinant protein expression as described previously (U.S. Pat. No. 6,057,098). Human TAT complex used for immunization and standardization of the assay was prepared by incubating human antithrombin III with human thrombin (Haematologic Technologies Inc., Essex Junction, Vt.) in borate-buffered saline for 15 minutes at room temperature. TAT complex was purified by gel filtration using a 1.5 cm×100 cm SUPERDEX 75 (Pharmacia, Piscataway, N.J.) column that was equilibrated with borate-buffered saline at a flow rate of 1 ml/minute.

Assays for S-100β were performed using commercially available murine anti-human S-100β monoclonal antibodies (Fitzgerald Industries International, Inc., Concord, Mass.). Commercially available human S-100β antigen was used for assay standardization (Advanced Immunochemical Inc., Long Beach, Calif.).

Assays for vWF A1-integrin were performed using murine monoclonal antibodies specific for the vWF A1 (clone RG46-1-1) and integrin (clone 152B) domains and standardized using vWF antigen, all obtained from Dr. Zaverio Ruggeri (Scripps Research Institute, La Jolla, Calif.).

Assays for VEGF were performed using two murine anti-human VEGF antibodies produced using phage display and recombinant protein expression as described previously (U.S. Pat. No. 6,057,098). Recombinant human VEGF was used for immunization and standardization of the assay. Recombinant human VEGF(165) is available from Research Diagnostics, Inc. (Cat# RDI-1020), Panvera (Cat# P2654), and Biosource International (Cat# PHG0145).

Immunoassays were performed on a TECAN Genesis RSP 200/8 Workstation. Biotinylated antibodies were pipetted into microtiter plate wells previously coated with avidin and incubated for 60 min. The solution containing unbound antibody was removed, and the cells were washed with a wash buffer, consisting of 20 mM borate (pH 7.42) containing 150 mM NaCl, 0.1% sodium azide, and 0.02% Tween-20. The plasma samples (10 μL) were pipeted into the microtiter plate wells, and incubated for 60 min. The sample was then removed and the wells were washed with a wash buffer. The antibody-alkaline phosphatase conjugate was then added to the wells and incubated for an additional 60 min, after which time, the antibody conjugate was removed and the wells were washed with a wash buffer. A substrate, (AttoPhos®, Promega, Madison, Wis.) was added to the wells, and the rate of formation of the fluorescent product was related to the concentration of the marker in the patient samples.

Example 3

Statistical Analyses

A panel that includes any combination of the above-referenced markers may be constructed to provide relevant information regarding the diagnosis of stroke and management of patients with stroke and TIAs. In addition, a subset of markers from this larger panel may be used to optimize sensitivity and specificity for stroke and various aspects of the disease. The example presented here describes the statistical analysis of data generated from immunoassays specific for BNP, IL-6, S-100β, MMP-9, TAT complex, and the A1 and integrin domains of vWF (vWF A1-integrin) used as a 6-marker panel. The thresholds used for these assays are 55 pg/ml for BNP, 27 pg/ml for IL-6, 12 pg/ml for S-100β, 200 ng/ml for MMP-9, 63 ng/ml for TAT complex, and 1200 ng/ml for vWF A1-integrin. A statistical analysis of clinical sensitivity and specificity was performed using these thresholds in order to determine efficacy of the marker panel in identifying patients with ischemic stroke, subarachnoid hemorrhage, intracerebral hemorrhage, all hemorrhagic strokes (intracranial hemorrhage), all stroke types, and TIAs. Furthermore, the effectiveness of the marker panel was compared to a current diagnostic method, computed tomography (CT) scan, through an analysis of clinical sensitivity and specificity.

The computed tomography (CT) scan is often used in the diagnosis of stroke. Because imaging is performed on the brain, CT scan is highly specific for stroke. The sensitivity of CT scan is very high in patients with hemorrhagic stroke early after onset. In contrast, the sensitivity of CT scan in the early hours following ischemic stroke is low, with approximately one-third of patients having negative CT scans on admission. Furthermore, 50% patients may have negative CT scans within the first 24 hours after onset. The data presented here indicates that the sensitivity of CT scan at admission for 24 patients was consistent with the expectation that only one-third of patients with ischemic stroke have positive CT scans. Use of the 6-marker panel, where a patient is positively identified as having a stroke if at least two markers are elevated, yielded a sensitivity of 79%, nearly 2.5 times higher than CT scan, with high specificity (92%). The specificity of CT scan in the study population is assumed to be close to 100%. One limitation of this assumption is that CT scans were not obtained from individuals comprising the normal population. Therefore, the specificity of CT scan in this analysis is calculated by taking into consideration other diseases or conditions that may yield positive CT scans. CT scans may be positive for individuals with non-stroke conditions including intracranial tumors, arteriovenous malformations, multiple sclerosis, or encephalitis. Each of these non-stroke conditions has an estimated incidence rate of 1% of the entire U.S. population. Because positive CT scans attributed to multiple sclerosis and encephalitis can commonly be distinguished from stroke, the specificity of CT scan for the diagnosis of stroke is considered to be greater than 98%. The data presented in Table 2 indicates that use of a panel of markers would allow the early identification of patients experiencing ischemic stroke with high specificity and higher sensitivity than CT scan.

TABLE 2

Marker panel vs. CT scan (n = 24)

| | Sensitivity | Specificity |
| --- | --- | --- |
| CT Scan | 33% | >98% |
| Markers | 92% | 92% |

The sensitivity and specificity of the 6-marker panel was evaluated in the context of ischemic stroke, subarachnoid hemorrhage, intracerebral hemorrhage, all hemorrhagic stroke (intracranial hemorrhage), and all stroke types combined at various times from onset. The specificity of the 6-marker panel was set to 92%, and patients were classified as having the disease if two markers were elevated. In addition, a 4-marker panel, consisting of BNP, S-100β, MMP-9 and vWF A1-integrin was evaluated in the same context as the 6-marker panel, with specificity set to 97% using the same threshold levels. The 4-marker panel is used as a model for selecting a subset of markers from a larger panel of markers in order to improve sensitivity or specificity for the disease, as described earlier. The data presented in Tables 3-7 indicate that both panels are useful in the diagnosis of all stroke types, especially at early times form onset. Use of the 4-marker panel provides higher specificity than the 6-marker panel, with equivalent sensitivities for hemorrhagic strokes within the first 48 hours from onset. The 6-marker panel demonstrates higher sensitivity for ischemic stroke at all time points than the 4-marker panel, indicating that the 6-marker approach is useful to attain high sensitivity (i.e. less false negatives), and the 4-marker panel is useful to attain high specificity (i.e. less false positives).

TABLE 3

Sensitivity Analysis - Ischemic Stroke

| Time from Onset of Symptoms (hr) | Number of Samples | SENSITIVITY with Specificity at 92% | SENSITIVITY with Specificity at 97% |
|---|---|---|---|
| 3 | 6 | 100 | 83.3 |
| 6 | 19 | 100 | 94.7 |
| 12 | 36 | 91.7 | 88.9 |
| 24 | 60 | 88.3 | 86.4 |
| 48 | 96 | 88.5 | 84.4 |
| All | 175 | 89.7 | 84.0 |

TABLE 4

Sensitivity Analysis - Subarachnoid Hemorrhage

| Time from Onset of Symptoms (hr) | Number of Samples | SENSITIVITY with Specificity at 92% | SENSITIVITY with Specificity at 97% |
|---|---|---|---|
| 3 | 3 | 100.0 | 100.0 |
| 6 | 5 | 100.0 | 100.0 |
| 12 | 6 | 100.0 | 100.0 |
| 24 | 14 | 96.3 | 92.0 |
| 48 | 32 | 95.2 | 86.8 |
| All | 283 | 91.3 | 83.0 |

TABLE 5

Sensitivity Analysis - Intracerebral Hemorrhage

| Time from Onset of Symptoms (hr) | Number of Samples | SENSITIVITY with Specificity at 92% | SENSITIVITY with Specificity at 97% |
|---|---|---|---|
| 3 | 3 | 100.0 | 100.0 |
| 6 | 5 | 100.0 | 100.0 |
| 12 | 6 | 100.0 | 100.0 |
| 24 | 13 | 96.3 | 92.0 |
| 48 | 24 | 89.9 | 78.3 |
| All | 60 | 87.2 | 86.4 |

TABLE 6

Sensitivity Analysis - All Hemorrhagic Stroke

| Time from Onset of Symptoms (hr) | Number of Samples | SENSITIVITY with Specificity at 92% | SENSITIVITY with Specificity at 97% |
|---|---|---|---|
| 3 | 6 | 100.0 | 100.0 |
| 6 | 10 | 100.0 | 100.0 |
| 12 | 12 | 100.0 | 100.0 |
| 24 | 27 | 96.3 | 92.0 |
| 48 | 56 | 92.9 | 84.6 |
| All | 343 | 90.7 | 83.6 |

TABLE 7

Sensitivity Analysis - All Stroke

| Time from Onset of Symptoms (hr) | Number of Samples | SENSITIVITY with Specificity at 92% | SENSITIVITY with Specificity at 97% |
|---|---|---|---|
| 3 | 12 | 100.0 | 91.7 |
| 6 | 29 | 100.0 | 96.6 |
| 12 | 48 | 93.8 | 91.7 |
| 24 | 87 | 90.8 | 88.5 |
| 48 | 152 | 90.1 | 84.2 |
| All | 518 | 90.4 | 83.8 |

The 6-marker and 4-marker panels were also evaluated for their ability to identify patients with transient ischemic attacks (TIAs). By nature, TIAs are ischemic events with short duration that do not cause permanent neurological damage. TIAs may be characterized by the localized release of markers into the bloodstream that is interrupted with the resolution of the event. Therefore, it is expected that the sensitivity of the panel of markers would decrease over time. Both the 6-marker panel, with specificity set to 92%, and the 4-marker panel, with specificity set to 97%, exhibit significant decreases in sensitivity within the first 24 hours of the event, as described in Table 8. These decreases are not observed in any of the stroke populations described in Tables 3-7. The data indicate that the collection of data from patients at successive time points may allow the differentiation of patients with TIAs from patients with other stroke types. The identification of patients with TIAs is beneficial because these patients are at increased risk for a future stroke.

TABLE 8

Sensitivity Analysis - TIA

| Time from Onset of Symptoms (hr) | Number of Samples | SENSITIVITY with Specificity at 92% | SENSITIVITY with Specificity at 97% |
|---|---|---|---|
| 0-6 | 9 | 100.0 | 88.9 |
| 6-12 | 7 | 57.1 | 57.1 |
| 12-24 | 8 | 37.5 | 37.5 |

Example 4

Markers for Cerebral Vasospasm in Patients Presenting with Subarachnoid Hemorrhage 45 consecutive patients, 38 admitted to a hospital with aneurysmal subarachnoid hemorrhage (SAH), and 7 control patients admitted for elective aneurysm clipping, were included in this study. In all patients with SAH, venous blood samples were taken by venipuncture at time of hospital admission and daily thereafter for 12 consecutive days or until the onset of vasospasm. Development of cerebral vasospasm was defined as the onset of focal neurological deficits 4-12 days after SAH or transcranial doppler (TCD) velocities >190 cm/s. In patients undergoing elective aneurysm clipping, 3±1 venous blood samples were taken per patient over the course of a median of 13 days after surgery. Collected blood was centrifuged (10,000 g), and the resulting supernatant was immediately frozen at −70° C. until analysis was completed. Measurements of vWF, VEGF, and MMP-9 were performed using immunometric enzyme immunoassays.

To determine if any changes in plasma vWF, VEGF, and MMP-9 observed in a pre-vasospasm cohort were a result of pre-clinical ischemia or specific to the development of cerebral vasospasm, these markers were also measured in the setting of embolic or thrombotic focal cerebral ischemia. A single venous blood sample was taken by venipuncture at the time of admission from a consecutive series of 59 patients admitted within 24 hours of the onset of symptomatic focal ischemia. Forty-two patients admitted with symptomatic focal ischemia subsequently demonstrated MRI evidence of cerebral infarction. Seventeen patients did not demonstrate radiological evidence of cerebral infarction, experienced symptomatic resolution, were classified as transient ischemic attack, and therefore were not included in analysis.

Statistical Analysis

Three cohorts were classified as non-vasospasm (patients admitted with SAH and not developing cerebral vasospasm), pre-vasospasm (patients admitted with SAH and subsequently developing cerebral vasospasm), and focal ischemia (patients admitted with symptomatic focal ischemia subsequently defined as cerebral infarction on MRI). Mean peak plasma vWF, VEGF, and MMP-9 levels were compared between cohorts by two-way ANOVA. The alpha error was set at 0.05. When the distribution had kurtosis, significant skewing, or the variances were significantly different, the non-parametric Mann Whitney U statistic for inter-group comparison was used. Correlations between Fisher grade and plasma markers were assessed by the Spearman Rank correlation coefficient. Logistic regression analysis adjusting for patient age, gender, race, Hunt and Hess, and Fisher grade was used to calculate the odds ratio of developing vasospasm per threshold of plasma marker.

Results

Thirty eight patients were admitted and yielded their first blood sample 1±1 days after SAH. Of these, 22 (57%) developed cerebral vasospasm a median seven days (range, 4-11 days) after SAH. Eighteen (47%) developed focal neurological deficits and four (10%) demonstrated TCD evidence of vasospasm only. Three patients in the SAH, non-vasospasm cohort were Fisher grade 1 and were not included in inter-cohort plasma marker comparison. Patient demographics, clinical characteristics, and Fisher grades for the non-vasospasm and pre-vasospasm cohorts are given in Table 9.

TABLE 9

Demographics, clinical presentation, and radiographical characteristics of 38 patients admitted with SAH.

|  | SAH, Non-Vasospasm (n = 16) | SAH, Pre-Vasospasm (n = 22) |
|---|---|---|
| Age† | 56 ± 10 years | 54 ± 13 years |
| Female | 12 (75%) | 18 (82%) |
| Admission GCS† | 14 (11-15) | 12 (9-14) |
| Admission HH‡ | 2 (1-3) | 3 (2-4) |
| Fisher Grade‡ | 3 (2-3) | 3 (2-4) |

†Values given as Mean ± SD, GCS, Glasgow Coma Scale

‡Values given as Median (interquartile range) HH, Hunt and Hess Scale

In the non-vasospasm cohort, mean peak plasma vWF (p=0.974), VEGF (p=0.357), and MMP-9 (p=0.763) were unchanged versus controls (Table 10). Plasma vWF, VEGF, and MMP-9 were increased in the pre-vasospasm versus non-vasospasm cohort (Table 10). Increasing Fisher grade correlated to greater peak plasma vWF (p<0.05), VEGF (p<0.01) and MMP-9 (p<0.05).

Additionally, twenty males and 22 females (age: 59±15 years) presented within 24 hours of symptomatic focal ischemia with a mean NIH stroke scale score of 6.7±6.6. In the focal ischemia cohort, mean peak plasma vWF (p=0.864), VEGF (p=0.469), and MMP-9 (p=0.623) were unchanged versus controls (Table 10). Plasma vWF, VEGF, and MMP-9 were markedly increased in the pre-vasospasm versus focal ischemia cohort (Table 10).

TABLE 10

Mean peak plasma markers in the non-vasospasm, pre-vasospasm, and focal ischemia cohorts. Control group given as reference.

|  | Focal Ischemia (n = 87) | p Value Versus SAH pre | SAH, no Vasospasm (n = 16) | p Value Versus SAH pre | SAH, pre-Vasospasm (n = 22) | Controls (n = 7) |
|---|---|---|---|---|---|---|
| vWF | 4645 ± 875 | 0.010 | 4934 ± 599 | 0.025 | 5526 ± 929 | 4865 ± 868 |
| VEGF | 0.03 ± 0.04 | 0.001 | 0.06 ± 0.06 | 0.023 | 0.12 ± 0.06 | 0.04 ± 0.06 |
| MMP-9 | 250 ± 308 | 0.001 | 438 ± 154 | 0.006 | 705 ± 338 | 408 ± 348 |

Following SAH, elevated plasma vWF, VEGF, and MMP-9 independently increased the odds of subsequent vasospasm 17 to 25 fold with positive predictive values ranging from 75% to 92% (Table 11).

TABLE 11

Positive/negative predictive values and odds ratio for subsequent onset of vasospasm associated with various levels of plasma vWF, VEGF, and MMP-9 by logistic regression analysis.

| Plasma Marker | p Value | Odds Ratio | PPV | NPV |
|---|---|---|---|---|
| vWF (ng/ml) | | | | |
| >5800 | 0.101 | 9.2 | 88% | 57% |
| >5500 | 0.033 | 17.6 | 92% | 67% |
| >5200 | 0.144 | 4.2 | 71% | 63% |
| VEGF (ng/ml) | | | | |
| >0.12 | 0.050 | 20.7 | 75% | 58% |
| >0.08 | 0.023 | 16.8 | 60% | 75% |
| >0.06 | 0.064 | 7.3 | 64% | 73% |
| MMP-9 (ng/ml) | | | | |
| >700 | 0.045 | 25.4 | 91% | 64% |
| >600 | 0.105 | 5.7 | 77% | 61% |
| >500 | 0.111 | 4.9 | 68% | 65% |

Example 5

Exemplary Panels for Diagnosing Stroke

The following tables demonstrate the use of methods of the present invention for the diagnosis of stroke. The "analytes panel" represents the combination of markers used to analyze test samples obtained from stroke patients and from non-stroke donors (NHD indicates normal healthy donor; NSD indicates non-specific disease donor). The time (if indicated) represents the interval between onset of symptoms and sample collection. ROC curves were calculated for the sensitivity of a particular panel of markers versus 1-(specificity) for the panel at various cutoffs, and the area under the curves determined. Sensitivity of the diagnosis (Sens) was determined at 92.5% specificity (Spec); and specificity of the diagnosis was also determined at 92.5% sensitivity.

TABLE 12

3-Marker Analyte Panel - Analytes: Caspase-3, MMP-9, GFAP.

| Specimens | Stroke vs NHD + NSD | | | Stroke vs NHD | | | Stroke vs NSD | | |
|---|---|---|---|---|---|---|---|---|---|
| Time Interval | All Times | | | All Times | | | All Times | | |
| Stroke (n) | 448 | | | 448 | | | 448 | | |
| non-Stroke (n) | 338 | | | 236 | | | 102 | | |
| Parameter | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens |
| Value | .944 | 85.7% | 85.2% | .955 | 86.6% | 89.0% | .919 | 75.0% | 76.5% |
| Specimens | Stroke vs NHD | | | Stroke vs NSD | | | Stroke vs NHD | | | Stroke vs NSD | | |
| Time Interval | 0-6 h | | | 0-6 h | | | 6-48 h | | | 6-48 h | | |
| Stroke (n) | 16 | | | 16 | | | 89 | | | 89 | | |
| non-Stroke (n) | 236 | | | 102 | | | 236 | | | 102 | | |
| Parameter | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens |
| Value | .958 | 93.8% | 95.8% | .931 | 87.5% | 92.2% | .963 | 86.5% | 90.3% | .920 | 71.9% | 76.5% |

TABLE 13

4-Marker Panel - Analytes: Caspase-3, MMP-9, vWF-A1 and BNP.

| Specimens | Stroke vs NHD + NSD | | | Stroke vs NHD | | | Stroke vs NSD | | |
|---|---|---|---|---|---|---|---|---|---|
| Time Interval | All Times | | | All Times | | | All Times | | |
| Stroke (n) | 482 | | | 482 | | | 482 | | |
| non-Stroke (n) | 331 | | | 234 | | | 97 | | |
| Parameter | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens |
| Value | .963 | 92.9% | 92.7% | .980 | 94.6% | 96.6% | .923 | 74.7% | 83.5% |
| Specimens | Stroke vs NHD | | Stroke vs NSD | | Stroke vs NHD | | Stroke vs NSD | |
| Time Interval | 0-6 h | | 0-6 h | | 6-48 h | | 6-48 h | |
| Stroke (n) | 18 | | 18 | | 101 | | 101 | |
| non-Stroke (n) | 234 | | 97 | | 234 | | 97 | |

TABLE 13-continued

4-Marker Panel - Analytes: Caspase-3, MMP-9, vWF-A1 and BNP.

| Parameter | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens |
|---|---|---|---|---|---|---|---|---|---|---|---|---|
| Value | .968 | 94.4% | 96.6% | .912 | 77.8% | 83.5% | .987 | 98.0% | 97.0% | .937 | 76.2% | 85.6% |

TABLE 14

6-Marker Panels: Analytes as indicated.

|  | Panel 1 | Panel 2 | Panel 3 | Panel 4 |
|---|---|---|---|---|
| NCAM | ✓ | ✓ | ✓ | ✓ |
| BDNF | ✓ | ✓ | ✓ | ✓ |
| Caspase-3 | ✓ | ✓ | ✓ | ✓ |
| MMP-9 | ✓ | ✓ | ✓ | ✓ |
| vWF-A1 | ✓ | ✓ | ✓ |  |
| VEGF | ✓ |  |  | ✓ |
| S100 |  | ✓ |  |  |
| vWF-Integrin |  |  |  | ✓ |
| MCP1 |  |  | ✓ |  |
| GFAP |  |  |  |  |

|  | Panel 1 Time | | | Panel 2 Time | | | Panel 3 Time | | | Panel 4 Time | | |
|---|---|---|---|---|---|---|---|---|---|---|---|---|
|  | all | 0-6 | 6-48 | all | 0-6 | 6-48 | all | 0-6 | 6-48 | all | 0-6 | 6-48 |
| Stroke (n) | 372 | 25 | 106 | 372 | 25 | 106 | 372 | 25 | 106 | 362 | 25 | 106 |
| non-Stroke (n) | 109 | 109 | 109 | 109 | 109 | 109 | 109 | 109 | 109 | 109 | 109 | 109 |
| ROC Area | 0.940 | 0.985 | 0.946 | 0.955 | 0.988 | 0.952 | 0.948 | 0.986 | 0.944 | 0.952 | 0.985 | 0.948 |
| Sens @ 92.5% Spec | 94.6% | 100.0% | 90.6% | 95.2% | 100.0% | 96.2% | 95.3% | 100.0% | 93.4% | 93.6% | 100.0% | 95.3% |
| Spec @ 92.5% Sens | 92.7% | 98.2% | 90.8% | 93.6% | 98.2% | 92.7% | 92.7% | 98.2% | 93.6% | 92.7% | 97.2% | 92.7% |

|  | Panel 5 | Panel 6 | Panel 8 | Panel 10 |
|---|---|---|---|---|
| NCAM |  |  | ✓ | ✓ |
| BDNF | ✓ | ✓ | ✓ | ✓ |
| Caspase-3 |  | ✓ |  | ✓ |
| MMP-9 | ✓ | ✓ | ✓ | ✓ |
| vWF-A1 |  | ✓ | ✓ |  |
| VEGF |  |  |  |  |
| S100 | ✓ | ✓ | ✓ | ✓ |
| vWF-Integrin | ✓ |  |  |  |
| MCP1 | ✓ |  |  |  |
| GFAP | ✓ | ✓ | ✓ | ✓ |

|  | Panel 5 Time | | | Panel 6 Time | | | Panel 8 Time | | | Panel 10 Time | | |
|---|---|---|---|---|---|---|---|---|---|---|---|---|
|  | all | 0-6 | 6-48 | all | 0-6 | 6-48 | all | 0-6 | 6-48 | all | 0-6 | 6-48 |
| Stroke (n) | 109 | 109 | 109 | 109 | 109 | 109 | 109 | 109 | 109 | 109 | 109 | 109 |
| non-Stroke (n) | 360 | 25 | 105 | 367 | 25 | 106 | 367 | 25 | 106 | 367 | 25 | 106 |
| ROC Area | 0.940 | 0.984 | 0.944 | 0.937 | 0.963 | 0.937 | 0.953 | 0.982 | 0.941 | 0.947 | 0.979 | 0.948 |
| Sens @ 92.5% Spec | 94.6% | 100.0% | 86.7% | 94.6% | 100.0% | 94.3% | 92.9% | 100.0% | 94.3% | 94.0% | 100.0% | 93.4% |
| Spec @ 92.5% Sens | 92.7% | 97.2% | 90.8% | 92.7% | 93.6% | 92.7% | 92.7% | 96.3% | 92.7% | 92.7% | 95.4% | 92.7% |

TABLE 15

7-Marker Panel - Analytes: Caspase-3, NCAM, MCP-1, S100-β, MMP-9, vWF-integrin and BNP.

| Specimens | Stroke vs NHD + NSD | Stroke vs NHD | Stroke vs NSD |
|---|---|---|---|
| Time Interval | All Times | All Times | All Times |
| Stroke (n) | 419 | 419 | 419 |
| non-Stroke (n) | 324 | 207 | 117 |

TABLE 15-continued

7-Marker Panel - Analytes: Caspase-3, NCAM, MCP-1, S100-β, MMP-9, vWF-integrin and BNP.

| Parameter | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens |
|---|---|---|---|---|---|---|---|---|---|
| Value | .953 | 88.3% | 89.5% | .962 | 92.6% | 92.8% | .937 | 79.5% | 83.8% |
| Specimens | Stroke vs NHD | | | Stroke vs NSD | | | Stroke vs NHD | | Stroke vs NSD |
| Time Interval | 0-6 h | | | 0-6 h | | | 6-48 h | | 6-48 h |
| Stroke (n) | 21 | | | 21 | | | 86 | | 86 |
| non-Stroke (n) | 207 | | | 117 | | | 207 | | 117 |

| Parameter | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens |
|---|---|---|---|---|---|---|---|---|---|---|---|---|
| Value | .930 | 85.7% | 77.8% | .900 | 81.0% | 62.4% | .972 | 96.5% | 92.8% | .948 | 82.6% | 83.8% |

TABLE 16

Table 15. 7-Marker Panel - Analytes: Caspase-3, NCAM, MCP-1, S100-β, MMP-9, vWF-integrin and BNP.

| | Analyte | Stroke vs NHD | Stroke vs NHD + NSD | Stroke vs NHD | Stroke vs NHD | Stroke vs NHD | Stroke vs NHD | Stroke vs NHD |
|---|---|---|---|---|---|---|---|---|
| | Caspase | x | x | x | x | x | x | x |
| | NCAM | x | x | x | x | x | x | x |
| | MCP-1 | x | x | x | x | x | x | x |
| | S-100b | x | x | x | x | x | x | x |
| | MMP-9 (omni)* | | | x | | | | |
| | MMP-9 (18/16)** | x | x | | | | | |
| | MMP-9 (18/17)*** | | | | x | | | |
| | MMP-9 (omni + 18/16) | | | | | x | | |
| | MMP-9 (omni + 18/17) | | | | | | x | |
| | MMP-9 (18/16 + 18/17) | | | | | | | x |
| | vWF-Integrin | x | x | x | x | x | x | x |
| | BNP | x | x | x | x | x | x | x |
| All Times | Stroke (n) | 419 | 419 | 500 | 427 | 417 | 425 | 418 |
| | non-Stroke (n) | 207 | 324 | 248 | 208 | 207 | 208 | 207 |
| | ROC Area | 0.991 | 0.953 | 0.987 | 0.990 | 0.993 | 0.995 | 0.990 |
| | Sens @ 92.5% Spec | 97.4% | 88.3% | 97.2% | 97.9% | 99.0% | 98.4% | 97.4% |
| | Spec @ 92.5% Sens | 99.9% | 89.5% | 97.6% | 99.0% | 99.5% | 99.5% | 99.0% |
| 0-6 hours | Stroke (n) | 21 | 21 | 24 | 21 | 21 | 21 | 21 |
| | non-Stroke (n) | 207 | 324 | 248 | 208 | 207 | 208 | 207 |
| | ROC Area | 1.000 | 0.939 | 1.000 | 1.000 | 1.000 | 1.000 | 1.000 |
| | Sens @ 92.5% Spec | 100.0% | 95.2% | 100.0% | 100.0% | 100.0% | 100.0% | 100.0% |
| | Spec @ 92.5% Sens | 100.0% | 96.0% | 100.0% | 100.0% | 100.0% | 100.0% | 100.0% |
| 6-48 hours | Stroke (n) | 86 | 86 | 102 | 90 | 85 | 89 | 86 |
| | non-Stroke (n) | 207 | 324 | 248 | 208 | 207 | 208 | 207 |
| | ROC Area | 0.996 | 0.969 | 0.986 | 0.998 | 0.999 | 0.999 | 0.999 |
| | Sens @ 92.5% Spec | 100.0% | 96.5% | 98.0% | 100.0% | 100.0% | 100.0% | 100.0% |
| | Spec @ 92.5% Sens | 98.1% | 94.1% | 98.4% | 99.5% | 100.0% | 100.0% | 99.0% |

*Recognizes all forms of MMP-9
*Recognizes all forms of MMP-9 except active MMP-9
*Recognizes all forms of MMP-9 except MMP-9/TIMP complexes

TABLE 17

8-Marker Panel - Analytes: Caspase-3, NCAM, MCP-1, S100-β, MMP-9, vWF-Al, BNP and GFAP.

| Specimens | Stroke vs NHD + NSD | Stroke vs NHD | Stroke vs NSD |
|---|---|---|---|
| Time Interval | All Times | All Times | All Times |
| Stroke (n) | 368 | 380 | 380 |
| non-Stroke (n) | 298 | 214 | 93 |

TABLE 17-continued

8-Marker Panel - Analytes: Caspase-3, NCAM, MCP-1, S100-β, MMP-9, vWF-A1, BNP and GFAP.

| Parameter | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens |
|---|---|---|---|---|---|---|---|---|---|
| Value | .970 | 93.9% | 94.5% | .980 | 94.2% | 96.3% | .947 | 80.3% | 90.3% |

| Specimens | Stroke vs NHD | Stroke vs NSD | Stroke vs NHD | Stroke vs NSD |
|---|---|---|---|---|
| Time Interval | 0-6 h | 0-6 h | 6-48 h | 6-48 h |
| Stroke (n) | 15 | 15 | 76 | 76 |
| non-Stroke (n) | 214 | 93 | 214 | 93 |

| Parameter | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens | Area | Sens @ 92.5% Spec | Spec @ 92.5% Sens |
|---|---|---|---|---|---|---|---|---|---|---|---|---|
| Value | .961 | 93.3% | 96.7% | .927 | 86.7% | 92.5% | .989 | 98.7% | 96.3% | .960 | 80.3% | 90.3% |

Example 6

Exemplary Panels for Differentiating Ischemic Stroke Versus Hemorrhagic Stroke The following table demonstrates the use of methods of the present invention for the differentiation of different types of stroke, in this example ischemic stroke versus hemorrhagic stroke. The "analyte panel" represents the combination of markers used to analyze test samples obtained from ischemic stroke patients and from hemorrhagic stroke patients. Sensitivity of the diagnosis, (Sens) was determined at 92.5% specificity (Spec); and specificity of the diagnosis was also determined at 92.5% sensitivity.

| | | | Ischemic vs. Hemorrhagic stroke | | | |
|---|---|---|---|---|---|---|
| | | | Run set 1 | Run set 2 | Run set 3 | Run set 4 |
| Analyte panel: | | CRP | x | x | x | x |
| | | NT-3 | x | | | x |
| | | vWF-total | x | | | |
| | | MMP-9 | x | x | x | x |
| | | VEGF | x | x | x | x |
| | | CKBB | x | x | x | x |
| | | MCP-1 | | x | x | x |
| | | Calbindin | | | x | |
| | | vWF-VP1 | | | x | |
| | | vWF A3 | | | x | |
| | | vWF A1-A3 | | | x | |
| | | Thrombin-antithrombin III complex | | | x | |
| | | Proteolipid protein | | | x | |
| | | IL-6 | | | x | |
| | | IL-8 | | | x | |
| | | Myelin Basic Protein | | | x | |
| | | S-100b | | | x | |
| | | Tissue factor | | | x | |
| | | GFAP | | | x | |
| | | vWF A1-integrin | | | x | |
| | | CNP | | | x | |
| | | NCAM | | | x | |
| All Times | N | Hemorrhagic stroke | 209 | 196 | 182 | 197 |
| | | Ischemic stroke | 114 | 110 | 122 | 109 |
| | | ROC Area | 0.898 | 0.867 | 0.920 | 0.882 |
| | | Sens @ 92.5% Spec | 75.1% | 62.2% | 77.9% | 64.0% |
| | | Spec @ 92.5% Sens | 77.2% | 71.8% | 85.7% | 72.5% |

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of determining a diagnosis of stroke or cerebral injury in a subject, said method comprising:
   analyzing a test sample obtained from a subject for the presence or amount of one or more markers selected from the group consisting of adenylate kinase, brain-derived neurotrophic factor, calbindin-D, creatine kinase-BB, glial fibrillary acidic protein, lactate dehydrogenase, myelin basic protein, neural cell adhesion molecule, neuron-specific enolase, neurotrophin-3, one or more isoforms of protein kinase C, proteolipid protein, S-100β, thrombomodulin, and marker(s) related thereto, wherein said test sample is blood, serum, or plasma;
   analyzing said test sample for the presence or amount of caspase-3 or marker(s) related thereto; and
   correlating the presence or amount of the analyzed markers to the occurrence or nonoccurrence of a stroke or cerebral injury in said subject.

2. A method according to claim 1, wherein said analyzed markers further comprise one or more acute phase reactant(s) selected from the group consisting of C-reactive protein, E-selectin, insulin-like growth factor-1, intercellular adhesion molecule-1, interleukin-1β, interleukin-1 receptor antagonist, interleukin-6, matrix metalloproteinase-3, matrix metalloproteinase-9, monocyte chemotactic protein-1, transforming growth factor β, tumor necrosis factor α, vascular cell adhesion molecule, and marker(s) related thereto.

3. A method according to claim 1, wherein said analyzed markers further comprise matrix metalloproteinase-9 or marker(s) related thereto.

4. A method according to claim 1, wherein said analyzed markers further comprise C-reactive protein or marker(s) related thereto.

5. A method according to claim 1, wherein said analyzed markers comprise S-100 β or marker(s) related thereto.

6. A method according to claim 1, wherein said analyzed markers further comprise D-dimer or marker(s) related thereto.

7. A method according to claim 1, wherein said analyzed markers further comprise B-type natriuretic peptide or marker(s) related thereto.

8. A method according to claim 1, wherein said analyzed markers comprise brain-derived neurotrophic factor, caspase-3, matrix metalloproteinase-9, neural cell adhesion molecule, vascular endothelial growth factor and the A1 domain of von Willebrand factor, optionally substituting one or more of said markers with marker(s) related thereto.

9. A method according to claim 1, wherein said analyzed markers comprise brain-derived neurotrophic factor, caspase-3, matrix metalloproteinase-9, neural cell adhesion molecule, S-100β and the A1 domain of von Willebrand factor, optionally substituting one or more of said markers with marker(s) related thereto.

10. A method according to claim 1, wherein said analyzed markers comprise brain-derived neurotrophic factor, caspase-3, matrix metalloproteinase-9, monocyte chemotactic protein-1, neural cell adhesion molecule, and the A1 domain of von Willebrand factor, optionally substituting one or more of said markers with marker(s) related thereto.

11. A method according to claim 1, wherein said analyzed markers comprise brain-derived neurotrophic factor, caspase-3, matrix metalloproteinase-9, neural cell adhesion molecule, vascular endothelial growth factor, and the integrin domain of von Willebrand factor, optionally substituting one or more of said markers with marker(s) related thereto.

12. A method according to claim 1, wherein said analyzed markers comprise brain-derived neurotrophic factor, caspase-3, glial fibrillary acidic protein, matrix metalloproteinase-9, S-100β, and the A1 domain of von Willebrand factor, optionally substituting one or more of said markers with marker(s) related thereto.

13. A method according to claim 1, wherein said analyzed markers comprise brain-derived neurotrophic factor, caspase-3, glial fibrillary acidic protein, matrix metalloproteinase-9, neural cell adhesion molecule, and S-100β, optionally substituting one or more of said markers with marker(s) related thereto.

14. A method according to claim 1, wherein said analyzed markers comprise B-type natriuretic peptide, caspase-3, matrix metalloproteinase-9, monocyte chemotactic protein-1, neural cell adhesion molecule, S-100β, and the integrin domain of von Willebrand factor, optionally substituting one or more of said markers with marker(s) related thereto.

15. A method according to claim 1, wherein said analyzed markers comprise B-type natriuretic peptide, caspase-3, glial fibrillary acidic protein, matrix metalloproteinase-9, monocyte chemotactic protein-1, neural cell adhesion molecule, S-100β, and the A1 domain of von Willebrand factor, optionally substituting one or more of said markers with marker(s) related thereto.

16. A method according to claim 1, further comprising comparing the amount of said analyzed markers to the amount of said analyzed markers in normal individuals, wherein changes in said amounts in said test sample as compared to normal individuals is indicative of the occurrence of a stroke or cerebral injury in said subject.

17. A method according to claim 1, wherein the method rules out the occurrence of a stroke or cerebral injury in said subject.

18. A method of determining a diagnosis of stroke or cerebral injury in a subject, said method comprising:
    analyzing a test sample obtained from a subject by performing an assay that detects one or more markers selected from the group consisting of adenylate kinase, brain-derived neurotrophic factor, calbindin-D, creatine kinase-BB, glial fibrillary acidic protein, lactate dehydrogenase, myelin basic protein, neural cell adhesion molecule, neuron-specific enolase, neurotrophin-3, one or more isoforms of protein kinase C, proteolipid protein, S-100β, and thrombomodulin, wherein said test sample is blood, serum, or plasma;
    analyzing said test sample by performing an assay that detects caspase-3; and correlating the results of said assays to the occurrence or nonoccurrence of a stroke or cerebral injury in said subject.

19. A method according to claim 18, wherein said method further comprises performing one or more assays that detect one or more acute phase reactant(s) selected from the group consisting of C-reactive protein, E-selectin, insulin-like growth factor-1, intercellular adhesion molecule-1, interleukin-1β, interleukin-1 receptor antagonist, interleukin-6, matrix metalloproteinase-3, matrix metalloproteinase-9, monocyte chemotactic protein-1, transforming growth factor β, tumor necrosis factor α, vascular cell adhesion molecule, and marker(s) related thereto.

20. A method according to claim 18, wherein said method further comprises performing an assay that detects metalloproteinase-9.

21. A method according to claim 18, wherein said method further comprises performing an assay that detects C-reactive protein.

22. A method according to claim 18, wherein said method comprises performing an assay that detects S-100 β.

23. A method according to claim 18, wherein said method further comprises performing an assay that detects D-dimer.

24. A method according to claim 18, wherein said method further comprises performing an assay that detects B-type natriuretic peptide, NT-proBNP, or proBNP.

25. A method according to claim 18, wherein said method comprises performing assays that detect brain-derived neurotrophic factor, caspase-3, matrix metalloproteinase-9, neural cell adhesion molecule, vascular endothelial growth factor and the A1 domain of von Willebrand factor.

26. A method according to claim 18, wherein said method comprises performing assays that detect brain-derived neurotrophic factor, caspase-3, matrix metalloproteinase-9, neural cell adhesion molecule, S-100β and the A1 domain of von Willebrand factor.

27. A method according to claim 18, wherein said method comprises performing assays that detect brain-derived neurotrophic factor, caspase-3, matrix metalloproteinase- 9, monocyte chemotactic protein-1, neural cell adhesion molecule, and the A1 domain of von Willebrand factor.

28. A method according to claim 18, wherein said method comprises performing assays that detect brain-derived neurotrophic factor, caspase-3, matrix metalloproteinase-9, neural cell adhesion molecule, vascular endothelial growth factor, and the integrin domain of von Willebrand factor.

29. A method according to claim 18, wherein said method comprises performing assays that detect brain-derived neurotrophic factor, caspase-3, glial fibrillary acidic protein, matrix metalloproteinase-9, S-100β, and the A1 domain of von Willebrand factor.

30. A method according to claim 18, wherein said method comprises performing assays that detect brain-derived neurotrophic factor, caspase-3, glial fibrillary acidic protein, matrix metalloproteinase-9, neural cell adhesion molecule, and S-100β.

31. A method according to claim 18, wherein said method comprises performing assays that detect B-type natriuretic peptide, caspase-3, matrix metalloproteinase-9, monocyte chemotactic protein-1, neural cell adhesion molecule, S-100β, and the integrin domain of von Willebrand factor.

32. A method according to claim 18, wherein said method comprises performing assays that detect B-type natriuretic peptide, caspase-3, glial fibrillary acidic protein, matrix metalloproteinase-9, monocyte chemotactic protein-1 neural cell adhesion molecule, S-100β, and the A1 domain of von Willebrand factor.

33. A method according to claim 18, further comprising comparing the amount of said analyzed markers to the amount of said analyzed markers in normal individuals, wherein changes in said amounts in said test sample as compared to normal individuals is indicative of the occurrence of a stroke or cerebral injury in said subject.

34. A method according to claim 18, wherein the method rules out the occurrence of a stroke or cerebral injury in said subject.

* * * * *

UNITED STATES PATENT AND TRADEMARK OFFICE
CERTIFICATE OF CORRECTION

| | |
|---|---|
| PATENT NO. | : 7,427,490 B2 |
| APPLICATION NO. | : 10/225082 |
| DATED | : September 23, 2008 |
| INVENTOR(S) | : Valkirs et al. |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 769 days Delete the phrase "by 769 days" and insert -- by 1000 days --

Signed and Sealed this

Eleventh Day of May, 2010

David J. Kappos
*Director of the United States Patent and Trademark Office*